US012781194B2

(12) United States Patent
Okano et al.

(10) Patent No.: US 12,781,194 B2
(45) Date of Patent: Nov. 3, 2026

(54) PRODUCTION METHOD AND KIT OF INDUCED PLURIPOTENT STEM CELLS

(71) Applicants: Keio University, Tokyo (JP); Nihon University, Tokyo (JP)

(72) Inventors: Hideyuki Okano, Tokyo (JP); Seiji Shiozawa, Tokyo (JP); Sho Yoshimatsu, Tokyo (JP); Kazuya Edamura, Tokyo (JP); Aozora Iguchi, Tokyo (JP)

(73) Assignees: Keio University, Tokyo (JP); Nihon University, Tokyo (JP)

( * ) Notice: Subject to any disclaimer, the term of this patent is extended or adjusted under 35 U.S.C. 154(b) by 939 days.

(21) Appl. No.: 17/603,645

(22) PCT Filed: Apr. 17, 2020

(86) PCT No.: PCT/JP2020/016924

§ 371 (c)(1),
(2) Date: Oct. 14, 2021

(87) PCT Pub. No.: WO2020/213725

PCT Pub. Date: Oct. 22, 2020

(65) Prior Publication Data

US 2022/0235331 A1 Jul. 28, 2022

(30) Foreign Application Priority Data

Apr. 17, 2019 (JP) ................................ 2019-078907

(51) Int. Cl.
*C12N 5/074* (2010.01)

(52) U.S. Cl.
CPC ...... *C12N 5/0696* (2013.01); *C12N 2501/115* (2013.01); *C12N 2501/15* (2013.01); *C12N 2501/602* (2013.01); *C12N 2501/603* (2013.01); *C12N 2501/604* (2013.01); *C12N 2501/605* (2013.01); *C12N 2501/606* (2013.01); *C12N 2501/608* (2013.01); *C12N 2501/727* (2013.01); *C12N 2506/08* (2013.01); *C12N 2506/1307* (2013.01); *C12N 2510/00* (2013.01)

(58) Field of Classification Search
CPC .. C12N 5/0684; C12N 5/0686; C12N 5/0696; C12N 5/068; A61K 35/22
See application file for complete search history.

(56) References Cited

U.S. PATENT DOCUMENTS

| | | | | |
|---|---|---|---|---|
| 10,738,280 | B2 * | 8/2020 | Okano | C12N 15/09 |
| 2012/0214236 | A1 | 8/2012 | Bhatia et al. | |
| 2015/0175973 | A1 | 6/2015 | Yamanaka et al. | |
| 2016/0208218 | A1 | 7/2016 | Tezuka et al. | |
| 2018/0010094 | A1 | 1/2018 | Hong et al. | |
| 2018/0080009 | A1 | 3/2018 | Okano et al. | |

FOREIGN PATENT DOCUMENTS

| | | | |
|---|---|---|---|
| JP | 2011-525793 | A | 9/2011 |
| JP | 5098028 | B2 | 12/2012 |
| JP | 2013-507932 | A | 3/2013 |
| JP | 6218229 | B2 | 10/2017 |
| JP | 2018-508216 | A | 3/2018 |
| JP | 2018-514220 | A | 6/2018 |
| JP | 2018-516064 | A | 6/2018 |
| JP | 6381442 | B2 | 8/2018 |
| WO | WO 2009/157593 | A1 | 12/2009 |
| WO | WO 2011/047300 | A1 | 4/2011 |
| WO | WO 2013/159103 | A1 | 10/2013 |
| WO | WO 2013-176233 | A1 | 11/2013 |
| WO | WO 2014/065435 | A1 | 5/2014 |
| WO | WO 2015/030111 | A1 | 3/2015 |
| WO | WO 2015/056804 | A1 | 4/2015 |
| WO | WO 2016/141162 | A1 | 9/2016 |
| WO | WO 2016/148253 | A1 | 9/2016 |
| WO | WO 2016/179243 | A1 | 11/2016 |

OTHER PUBLICATIONS

Si-Tayeb, K., Noto, F. K., Nagaoka, M., Li, J., Battle, M. A., Duris, C., North, P. E., Dalton, S., & Duncan, S. A. (2010). Highly efficient generation of human hepatocyte-like cells from induced pluripotent stem cells. Hepatology (Baltimore, Md.), 51(1), 297-305 . https://doi.org/10.1002/hep.23354 (Year: 2010).*

Kim JB, Zaehres H, Wu G, et al. Pluripotent stem cells induced from adult neural stem cells by reprogramming with two factors. Nature. 2008;454(7204):646-650. doi:10.1038/nature07061 (Year: 2008).*

Ye L, Swingen C, Zhang J. Induced pluripotent stem cells and their potential for basic and clinical sciences. Curr Cardiol Rev. 2013; 9(1):63-72. doi: 10.2174/157340313805076278 (Year: 2013).*

Nakajima-Koyama M, Lee J, Ohta S, Yamamoto T, Nishida E. Induction of Pluripotency in Astrocytes through a Neural Stem Cell-like State. J Biol Chem. 2015;290(52):31173-31188. doi: 10.1074/jbc. M115.683466 (Year: 2015).*

Quang, Tara et al. "Dosage and cell line dependent inhibitory effect of bFGF supplement in human pluripotent stem cell culture on inactivated human mesenchymal stem cells." PloS one vol. 9,1 e86031. Jan. 17, 2014, doi: 10.1371/journal.pone.0086031 (Year: 2014).*

(Continued)

*Primary Examiner* — Maria G Leavitt
*Assistant Examiner* — Kodye Lee Abbott
(74) *Attorney, Agent, or Firm* — Blank Rome LLP

(57) ABSTRACT

A method of producing induced pluripotent stem cells including a step for introducing an initialization factor into somatic cells of a mammal, and culturing in a neural stem cell culture medium to obtain induced neural stem cell-like cells, and a step for cultivating said induced neural stem cell-like cells in a growth medium to obtain induced pluripotent stem cells, wherein the initialization factor contains an OCT family, a SOX family, a KLF family, a MYC family, a LIN28 family and a P53 function inhibitor.

14 Claims, 38 Drawing Sheets

(56) References Cited

OTHER PUBLICATIONS

Chow L, Johnson V, Regan D, et al. Safety and immune regulatory properties of canine induced pluripotent stem cell-derived mesenchymal stem cells. Stem Cell Res. 2017;25:221-232. doi:10.1016/j.scr.2017.11.010 (Year: 2017).*

Montserrat N, De Oñate L, Garreta E, et al. Generation of Feeder-Free Pig Induced Pluripotent Stem Cells without Pou5f1. Cell Transplantation. 2012;21(5):815-825. doi: 10.3727/096368911X601019 (Year: 2012).*

T. Nishimura et al. "Feeder-Independent Canine Induced Pluripotent Stem Cells Maintained Under Serum-Free Conditions." Mol. Reprod. Dev., vol. 84, pp. 329-339, 2017.

M. Tsukamoto et al., "Generation of Footprint-Free Canine Induced Pluripotent Stem Cells Using Auto-Erasable Sendai Virus Vector." Stem Cells Development, vol. 27, No. 22, pp. 1577-1586, 2018.

X. Du et al., "Barriers for Deriving Transgene-Free Pig iPS Cells with Episomal Vectors." Stem Cells. vol. 33(11), pp. 3228-3238, 2015.

J. Yu et al., "Induced Pluripotent Stem Cell Lines Derived from Human Somatic Cells." Science, vol. 318, pp. 1917-1920, 2007.

T. Bowman et al., "Tissue-Specific Inactivation of p53 Tumor Suppression in the Mouse." Genes & Development, vol. 10, pp. 826-835, 1996.

S. Matoba et al., "Privileged Communication Embryonic Development Following Somatic Cell Nuclear Transfer Impeded by Persisting Histone Methylation." Cell, vol. 159(4), pp. 884-895, 2014.

Y.G. Chung et al., "Histone Demethylase Expression Enhances Human Somatic Cell Nuclear Transfer Efficiency and Promotes Derivation of Pluripotent Stem Cells." Cell Stem Cell, vol. 17, pp. 758-766, 2015.

M. Maekawa et al., "Direct Reprogramming of Somatic Cells is Promoted by Maternal Transcription Factor Glis1." Nature, vol. 474, pp. 225-229, 2011.

D.W. Scoville et al., "GLIS1-3: Emerging Roles in Reprogramming, Stem and Progenitor Cell Differentiation and Maintenance." Stem Cell Investig., vol. 4:80, 2017.

K. Okita et al., "An Efficient Nonviral Method to Generate Integration-Free Human-Induced Pluripotent Stem Cells from Cord Blood and Peripheral Blood Cells." Stem Cells, vol. 31, pp. 458-466, 2013.

S. C. Vermilyea et al., "Induced Pluripotent Stem Cell-Derived Dopaminergic Neurons from Adult Common Marmoset Fibroblasts." Stem Cells and Development, vol. 26, No. 17, pp. 1225-1235, 2017.

Z. Liu et al., "Elevated p53 Activities Restrict Differentiation Potential of MicroRNA-Deficient Pluripotent Stem Cells." Stem Cell Reports, vol. 9, pp. 1604-1617, 2017.

S. Yamasaki et al., "Development of Marmoset iPS Cell Induction Method using RNA and Chemical Substances, Programs and Abstracts of the 41st Annual Meeting of the Molecular Biology Society of Japan." 2-P-0445, 2018.

M. Nakajima et al., "Establishment of Induced Pluripotent Stem Cells from Common Marmoset Fibroblasts by RNA-Based Reprogramming." Biochemical and Biophysical Research Communications, vol. 515, pp. 593-599, 2019.

J. Yu et al., "Human Induced Pluripotent Stem Cells Free of Vector and Transgene Sequences." Science, vol. 324, pp. 797-801, 2009.

Int'l Search Report for Int'l Application No. PCT/JP2020/016924, dated Jul. 21, 2020.

Int'l Prelim Report on Patentability for Int'l App. No. PCT/JP2020/016924, dated Jul. 20, 2021.

First Office Action dated Sep. 22, 2023 issued in corresponding Chinese Patent Application No. 202080028932.0.

Extended European Search Report from corresponding EP Application No. 20792193.3 dated Dec. 20, 2022.

* cited by examiner

PRODUCTION METHOD AND KIT OF INDUCED PLURIPOTENT STEM CELLS

TECHNICAL FIELD

The present invention relates to a production method and a kit of induced pluripotent stem cells. Priority is claimed on Japanese Patent Application No. 2019-078907, filed Apr. 17, 2019, the content of which is incorporated herein by reference.

BACKGROUND ART

The technique for establishing iPS cells from human and mouse somatic cells has been improved and simplified, and the efficiency for establishing iPS cells has been increased as compared with that of the conventional techniques. Meanwhile, animals (pluripotency induction-resistant animals) for which establishing iPS cells from adult somatic cells is particularly difficult are present. As the pluripotency induction-resistant animals, dogs, pigs, marmosets, cats, cows, horses, and the like are known.

For example, canine iPS cells can be established by persistently expressing a reprogramming factor in canine fetus-derived fibroblasts (refer to, for example, Non Patent Document 1). In addition, canine iPS cells can be established from canine fetus-derived fibroblasts by using Sendai virus (refer to, for example, Non Patent Document 2). In addition, porcine iPS cells can be established by persistently expressing a reprogramming factor in porcine fetus-derived fibroblasts (refer to, for example, Non Patent Document 3).

CITATION LIST

Non Patent Document 1: Nishimura T et al., Feeder-independent canine induced pluripotent stem cells maintained under serum-free conditions. Mol. Reprod. Dev., Vol. 84, 329-339, 2017.

Non Patent Document 2: Tsukamoto M et al., Generation of Footprint-Free Canine Induced Pluripotent Stem Cells Using Auto-Erasable Sendai Virus Vector. Stem Cells Dev., 27, 1577-1586, 2018.

Non Patent Document 3: Du X et al., Barriers for Deriving Transgene-Free Pig iPS Cells with Episomal Vectors. Stem Cells, Vol. 33, 3228-3238, 2015.

SUMMARY OF INVENTION

An object of the present invention is to provide a new technique for establishing iPS cells from mammalian somatic cells.

The present invention includes the following aspects:

[1] A production method of induced pluripotent stem cells, the method including: a step of introducing a reprogramming factor into mammalian somatic cells and culturing the mammalian somatic cells in a neural stem cell culture medium to obtain induced neural stem cell-like cells; and a step of culturing the induced neural stem cell-like cells in a growth medium to obtain induced pluripotent stem cells, in which the reprogramming factor includes an OCT family, a SOX family, a KLF family, a MYC family, a LIN28 family, and a P53 function-inhibiting substance.

[2] The production method of induced pluripotent stem cells according to [1], in which the reprogramming factor further includes one or more selected from the group consisting of a KDM family, a GLIS family, and NANOG.

[3] The production method according to [1] or [2], in which the somatic cells are derived from an adult.

[4] The production method according to any one of [1] to [3], in which the neural stem cell culture medium contains a MAP kinase inhibitor, a GSK3β inhibitor, and a TGFβ inhibitor.

[5] The production method according to any one of [1] to [4], in which the growth medium contains bFGF.

[6] Induced pluripotent stem cells produced by the production method according to any one of [1] to [5].

[7] A kit for producing induced pluripotent stem cells from somatic cells of a pluripotency induction-resistant animal, the kit including: a reprogramming factor including an OCT family, a SOX family, a KLF family, a MYC family, a LIN28 family, and a P53 function-inhibiting substance; and a neural stem cell culture medium containing a MAP kinase inhibitor, a GSK3β inhibitor, and a TGFβ inhibitor.

[8] The kit according to [7], in which the reprogramming factor the reprogramming factor further includes one or more selected from the group consisting of a KDM family, a GLIS family, and NANOG.

[9] The kit according to [7] or [8], further including a growth medium containing bFGF.

Advantageous Effects of Invention

According to the present invention, it is possible to provide a new technique for establishing iPS cells from mammalian somatic cells.

BRIEF DESCRIPTION OF DRAWINGS

FIG. 3(*a*) is a photograph obtained by imaging cells, into which the EP-A vector set was introduced and which were cultured in a growth medium for 4 days, in a bright field. FIG. 3(*b*) is a photograph obtained by imaging fluorescence of EGFP of cells into which the EP-A vector set was introduced and which were cultured in a growth medium for 4 days.

FIG. 4(*a*) is a photograph of cells in which the EP-A vector set was introduced into E01F and which were cultured in a growth medium for 30 days. FIG. 4(*b*) is a photograph of cells in which the EP-A vector set was introduced into E02M and which were cultured in a growth medium for 30 days.

FIG. 6(*a*) is a photograph of a colony formed by introducing the EP-A vector set into E01F and then culturing in a neural stem cell culture medium. FIG. 6(*b*) is a photograph of a colony formed by introducing the EP-B vector set into E01F and then culturing in a neural stem cell culture medium. FIG. 6(*c*) is a photograph of a colony formed by introducing the EP-A vector set into E02M and then culturing in a neural stem cell culture medium. FIG. 6(*d*) is a photograph of a colony formed by introducing the EP-B vector set into E02M and then culturing in a neural stem cell culture medium.

FIG. 8(*a*) is a diagram showing the results of staining, with alkaline phosphatase, a colony obtained by introducing the EP-A vector set into E01F and culturing in a neural stem cell culture medium. FIG. 8(*b*) is a diagram showing the results of staining, with alkaline phosphatase, a colony obtained by introducing the EP-B vector set into E01F and culturing in a neural stem cell culture medium.

FIG. 9(*a*) is a photograph of a colony formed by introducing the EP-A vector set into marmoset embryonic fibroblasts (E01F) and culturing in a neural stem cell culture medium. FIG. 9(*b*) is a photograph of a colony formed by introducing the EP-A vector set into marmoset embryonic fibroblasts (E01F), culturing in a neural stem cell culture medium, and then culturing in a growth medium. FIG. 9(*c*) is a photograph of a colony formed by introducing the EP-B vector set into marmoset embryonic fibroblasts (E02M) and culturing in a neural stem cell culture medium. FIG. 9(*d*) is a photograph of a colony formed by introducing the EP-B vector set into marmoset embryonic fibroblasts (E02M), culturing in a neural stem cell culture medium, and then culturing in a growth medium.

DESCRIPTION OF EMBODIMENTS

Figure 1:
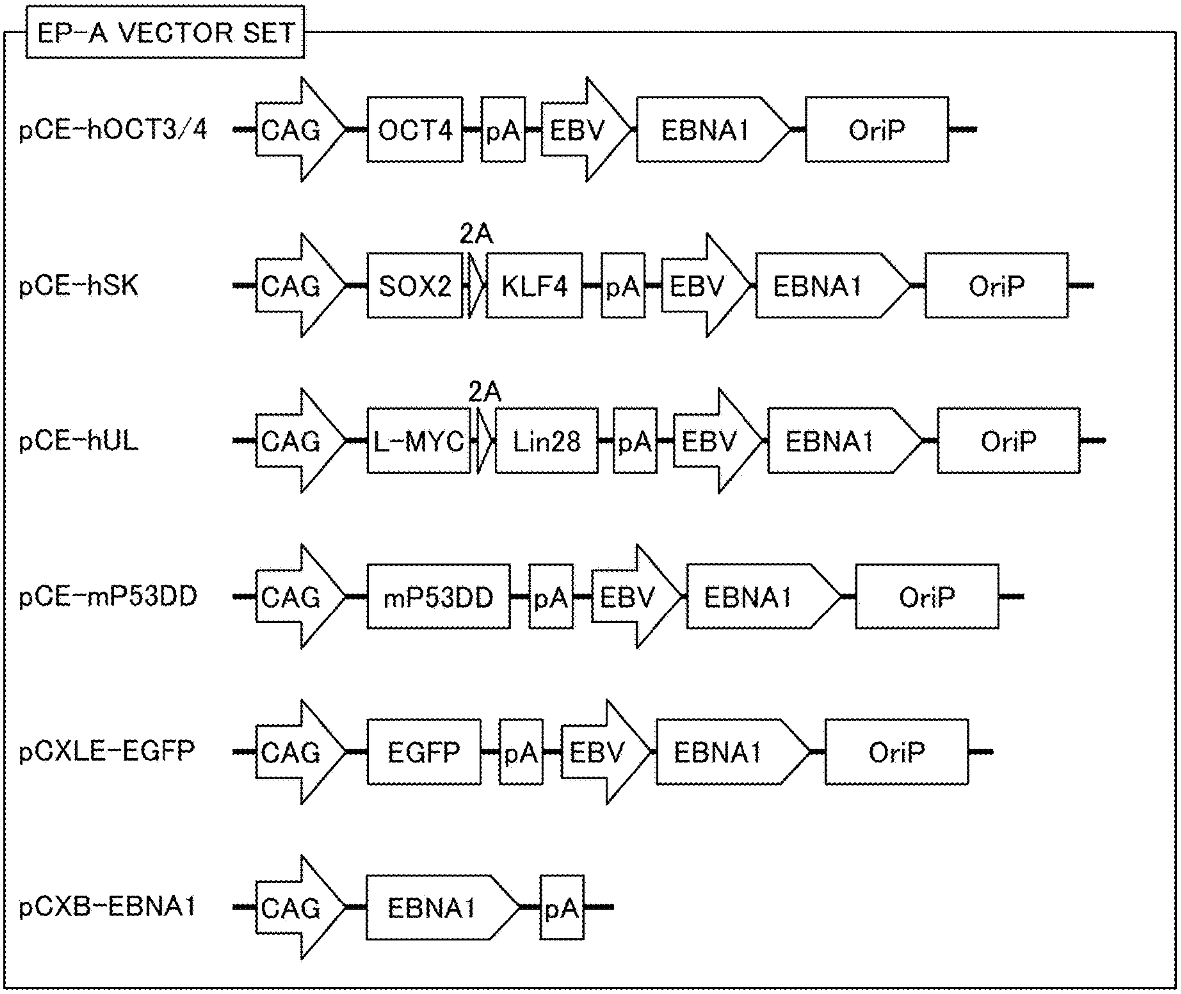
FIG. 1 is a diagram schematically showing an EP-A vector set for expressing a reprogramming factor.

Notation of Gene Name and Protein Name

In the present specification, human genes and human proteins, and genes and proteins of pluripotency induction-resistant animals are represented by uppercase alphabets. However, in some cases, human genes and genes of other species may be represented by uppercase alphabets without strict distinction. In addition, human proteins and proteins of other species may be represented by uppercase alphabets without strict distinction.

In the present specification, for example, the notation "SOX2" means both the SOX2 protein and the nucleic acid encoding it. In addition, for example, the notation "reprogramming factor" means both the reprogramming protein and the nucleic acid encoding it. In addition, for example, the notation "SOX family" means both the SOX protein and the nucleic acid encoding it.

Notation of Cell Name

In the present specification, induced pluripotent stem cells may be referred to as iPS cells or iPSCs. In addition, induced neural stem cell-like cells may be referred to as iNSL cells or iNSLCs.

Production Method

In one embodiment, the present invention provides a production method of induced pluripotent stem cells, the method including: a step (a) of introducing a reprogramming factor into mammalian somatic cells and culturing the mammalian somatic cells in a neural stem cell culture medium to obtain induced neural stem cell-like cells; and a step (b) of culturing the induced neural stem cell-like cells in a growth medium to obtain induced pluripotent stem cells, in which the reprogramming factor includes an OCT family, a SOX family, a KLF family, a MYC family, a LIN28 family, and a P53 function-inhibiting substance. In the present embodiment, the mammal may be a pluripotency induction-resistant animal.

In the present specification, the pluripotency induction-resistant animal refers to a mammal that cannot establish iPS cells even when the reprogramming factors of an OCT family, a SOX family, a KLF family, and a MYC family are expressed in combination in somatic cells of the adult pluripotency induction-resistant animal.

Examples of the pluripotency induction-resistant animal include, but are not limited to, monkeys, pigs, ferrets, sheep, cats, dogs, horses, cows, goats, and rabbits. Examples of monkeys include marmosets.

In the present embodiment, examples of somatic cells of the pluripotency induction-resistant animal which are as a material for producing iPS cells include fetus-derived somatic cells and adult-derived somatic cells. Examples of somatic cells include fat cells, cartilage cells, osteoblasts, bone cells, muscle cells, vascular cells, immune cells, epithelial cells, nerve cells, liver cells, pancreatic cells, and precursor cells thereof. The above-mentioned somatic cells may be undifferentiated cells or differentiated cells.

Marmosets, dogs, pigs, and ferrets are typical pluripotency induction-resistant animals. As will be described later in Examples, iPS cells, which do not have an expression construct expressing a reprogramming factor within the cells, can be established by transiently expressing the reprogramming factor intracellularly from somatic cells of adult marmosets, dogs, pigs, and ferrets by the production method of the present embodiment.

In the present embodiment, it is preferable to introduce a non-episomal vector having a nucleic acid encoding EBNA-1 into mammalian somatic cells together with the reprogramming factor.

Reprogramming Factor

In the present embodiment, the reprogramming factor includes an OCT family, a SOX family, a KLF family, an MYC family, a LIN28 family, and a P53 function-inhibiting substance.

Examples of the OCT family include OCT3/4, OCT1, OCT2, and OCT6. As the OCT family, OCT3/4 is preferable.

Examples of the SOX family include SOX2, SOX1, SOX3, SOX15, and SOX17.

Examples of the KLF family include KLF1, KLF2, KLF4, and KLF5.

Examples of the MYC family include C-MYC, N-MYC, and L-MYC.

Examples of the LIN28 family include LIN28 and LIN28B.

NANOG is a transcription factor having a homeodomain. When NANOG is expressed in somatic cells together with OCT4, SOX2, and LIN28, it is possible to establish iPS cells (refer to, for example, Yu J et al., Science, 318, 1917-1920 (2007)).

In the present specification, the P53 function-inhibiting substance may be any substance as long as it is a substance suppressing the function of P53 protein or a substance suppressing the expression of a P53 gene (for example, PCT International Publication No. WO2009/157593).

Examples of the substance suppressing the function of P53 protein include dominant negative mutants of P53, chemical substances that inhibit the function of P53 protein, anti-P53 antagonist antibodies, decoy nucleic acids containing a consensus sequence of P53 response elements, and P53 pathway-inhibiting substances. Examples of the substance suppressing the expression of a P53 gene include siRNA and shRNA for P53.

As the dominant negative mutant of P53, P53DD in which the amino acid at the positions 14 to 301 of mouse P53 (corresponding to the positions 11 to 304 in human P53) is deleted is preferable (refer to, for example, Bowman, T., Genes & Development, 10, 826-835 (1996)).

The reprogramming factor may further include one or more selected from the group consisting of a KDM family, a GLIS family, and NANOG.

The reprogramming factor preferably includes the OCT family, the SOX family, the KLF family, the MYC family, the LIN28 family, the P53 function-inhibiting substance, the KDM family, the GLIS family, and NANOG.

The KDM family has Lysine Demethylase activity and demethylates K9 of histone H3. As the KDM family, KDM1, KDM2, KDM3, KDM4, KDM5, and KDM6 are known. Forced expression of KDM4D or KDM4A demethylates the 9th lysine residue of histone H3 and promotes reprogramming of somatic cells (refer to, for example, Matoba et al., Cell, 159, 884-895 (2014); Chung Y G et al., Cell Stem Cell, 17, 758-766 (2015)).

The KDM family used as the reprogramming factor is not particularly limited, and examples thereof include KDM1, KDM2, KDM3, KDM4, KDM5, and KDM6. As the KDM family, KDM4A and KDM4D are preferable.

The GLIS family (GLI Similar family) is a zinc finger-type transcription factor. As the GLIS family, GLIS1, GLIS2, and GLIS3 are known. Forced expression of GLIS1 promotes the formation of iPS cells (refer to, for example, Maekawa et al., Nature, 474, 225-229 (2011)). In addition, GLIS1, GLIS2, and GLIS3 play various roles in stem cells (refer to, for example, Scoville D W et al., Stem Cell Investig, 4:80 (2017)).

The GLIS family used as the reprogramming factor is not particularly limited, and examples thereof include GLIS1, GLIS2, and GLIS3. As the GLIS family, GLIS1 is preferable.

The reprogramming factor may include an ESRR family.

The ESRR family (Estrogen-related receptor family) is a nuclear receptor. As the ESRR family, ESRRA, ESRRB, and ESRRG are known. When ESRRB or ESRRG is forcibly expressed together with OCT4 and SOX2, somatic cells can be reprogrammed (refer to, for example, Feng B et al., Nat. Cell. Biol., vol. 11, 197-203 (2009)).

The ESRR family used as the reprogramming factor is not particularly limited, and examples thereof include ESRRB and ESRRG.

Examples of combinations of the reprogramming factors include, but are not limited to, combinations exemplified in Table 1 as disclosed in PCT International Publication No. WO2015/056804.

TABLE 1

| Combination of reprogramming factors |
|---|
| OCT3/4, KLF4, C-MYC |
| OCT3/4, KLF4, C-MYC, SOX2 |
| OCT3/4, KLF4, SOX2 |
| OCT3/4, SOX2, NANOG, LIN28 |
| OCT3/4, KLF4, C-MYC, SOX2, NANOG, LIN28 |
| OCT3/4, KLF4 |
| OCT3/4, C-MYC |
| OCT3/4, SOX2 |
| OCT3/4, SOX2, NANOG |
| OCT3/4, SOX2, LIN28 |
| OCT3/4, SOX2, C-MYC, ESRRB |
| OCT3/4, SOX2, ESRRB |
| OCT3/4, KLF4, L-MYC |
| OCT3/4, NANOG |
| OCT3/4 |
| OCT3/4, KLF4, C-MYC, SOX2, NANOG, LIN28 |
| OCT3/4, SOX2, KLF4, L-MYC, LIN28 |
| OCT3/4, SOX2, KLF4, L-MYC, LIN28, GLIS1 |

The reprogramming factor may have a mutation as long as the reprogramming factor has the activity to reprogram pluripotency induction-resistant somatic cells. When the reprogramming factor has a mutation, the reprogramming factor preferably has 80% or more sequence identity, more preferable has 90% or more sequence identity, and further preferable has 95% or more sequence identity with respect to proteins or mRNAs specified by the NCBI accession numbers exemplified in Table 1.

The sequence identity of an amino acid sequence is a value indicating a proportion in which an amino acid sequence of a target (target amino acid sequence) matches an amino acid sequence as a reference (reference amino acid sequence). The sequence identity of a target amino acid sequence with respect to a reference amino acid sequence can be obtained as follows, for example. First, a reference amino acid sequence and a target amino acid sequence are aligned. Each amino acid sequence may contain a gap so as to maximize the sequence identity. Subsequently, the number of amino acids matched in the reference amino acid sequence and the target amino acid sequence can be calculated to obtain the sequence identity according to Formula (1).

$$\text{Sequence identity (\%)} = \text{number of amino acids matched/total number of amino acids in target amino acid sequence} \times 100 \quad (1)$$

Similarly, the sequence identity of a target base sequence with respect to a reference base sequence can be obtained as follows, for example. First, a reference base sequence and a target base sequence are aligned. Each base sequence may contain a gap so as to maximize the sequence identity. Subsequently, the number of bases matched in the reference base sequence and the target base sequence can be calculated to obtain the sequence identity according to Formula (2).

$$\text{Sequence identity (\%)} = \text{number of bases matched/total number of bases in target base sequence} \times 100 \quad (2)$$

In the present embodiment, the animal species from which the reprogramming factor is derived may be the same as or different from the animal species from which somatic cells into which the reprogramming factor is introduced are derived. Those skilled in the art can obtain the amino acid sequence or mRNA sequence of the reprogramming factor of the desired animal species from the database.

The reprogramming factor may be mRNA specified by the NCBI accession number exemplified in Table 2, a protein encoded by the mRNA, or a gene that transcribes the mRNA (refer to, for example, Japanese Patent No. 5098028, Japanese Patent No. 6381442, PCT International Publication No. WO2015/030111, and PCT International Publication No. WO2015/056804). The accession numbers shown in Table 1 are human cDNA sequences.

TABLE 2

| Name | Accession number |
|---|---|
| OCT3/4 | NM_002701 |
| OCT1 | NM_002697 |
| OCT2 | NM_002698 |
| OCT6 | NM_002699 |
| SOX2 | NM_003106 |
| SOX1 | NM_005986 |
| SOX3 | NM_005634 |
| SOX15 | NM_006942 |
| SOX17 | NM_022454 |
| KLF1 | NM_006563 |
| KLF4 | NM_004235 |
| KLF2 | NM_016270 |
| KLF5 | NM_001730 |
| C-MYC | NM_002467 |
| N-MYC | NM_005378 |
| L-MYC | NM_005376 |
| LIN28 | NM_024674 |
| LIN28B | NM_001004317 |
| KDM1 | NM_015013 |
| KDM2 | NM_012308 |
| KDM3 | NM_018433 |
| KDM4A | NM_014663 |
| KDM4D | NM_018039 |
| KDM5 | NM_001042603 |
| KDM6 | NM_001291415 |
| GLIS1 | NM_147193 |
| GLIS2 | NM_032575 |
| GLIS3 | NM_001042413 |
| NANOG | NM_152676 |
| ESRRB | NM_004452 |
| ESRRG | NM_001438 |

The reprogramming factor of the present embodiment may be introduced in the form of a protein, or may be introduced in the form of mRNA encoding the protein or a nucleic acid such as an expression vector.

As will be described later in Examples, the reprogramming factor preferably includes OCT4, SOX2, KLF4, L-MYC, LIN28, and mP53DD.

In addition, as will be described later in Examples, the reprogramming factor preferably includes OCT4, SOX2, KLF4, L-MYC, LIN28, mP53DD, KLF2, KDM4D, GLIS1, and NANOG.

Step (a)

In the present step, a reprogramming factor is introduced into mammalian somatic cells, and culturing is performed in a neural stem cell culture medium to obtain induced neural stem cell-like cells. The mammal may be a pluripotency induction-resistant animal.

When the reprogramming factor is protein or RNA, a conventional method such as microinjection or electroporation can be used as a method of incorporating the reprogramming factor into cells.

When the reprogramming factor is a protein, examples of the method of incorporating the reprogramming factor into cells include a method using protein transduction reagent, a method using protein transduction domain (PTD) fusion proteins, and a microinjection method.

As the protein transduction reagent, for example, it is possible to use known reagents such as cationic lipid type introduction reagents such as BioPORTER (Gelantis), Pro-DeliverIN (OZ Bioscience), Ab-DeliverIN (OZ Bioscience), PULSin Kit (Polyplus-transfection SAS), Proteinfectin (Targeting Systems), and Fuse-It P (NIPPON Genetics); membrane-permeable peptide type introduction reagents such as Chariot (Active motif), Xfect Protein (Clontech), JBS Transduction Kit (Jena Bioscience), and Cellvader (GE Healthcare); lipid type introduction reagents such as Profect-1 (Targeting Systems); and HVJ envelope type introduction reagents such as GenomONE™-Neo (FD) (Cosmo Bio).

As a reagent for introducing mRNA, for example, it is possible to use known reagents such as TransIT-mRNA Transfection Reagent (TaKaRa), Lipofectamine Messenger MAX™ (Thermo Fisher Scientific), and Xfect™ RNA Transfection Reagent (Clonetech).

The reprogramming factor may be an expression construct in which DNA encoding the reprogramming factor and a promoter are linked. The promoter may be one having activity in a target cell or may be an expression-inducible promoter capable of inducing activity by a drug or the like.

For example, the promoter may be a cytomegalovirus promoter (CMV promoter) or a CMV early enhancer/chicken beta actin (CAG promoter) which has strong promoter activity in almost all cells, or may be a promoter having tissue-specific promoter activity.

Examples of the expression-inducible promoter include, but are not limited to, a doxycycline-inducible promoter, a Cumate-inducible promoter, a heat shock promoter, and a light-induced promoter. In addition, it may be a system in which expression is induced during Cre recombinant enzyme action by a protein translation stop codon or polyadenylation sequence sandwiched between loxP sites.

The above-mentioned expression construct may be one incorporated into, for example, a transposon vector, an adenovirus vector, an adeno-associated virus vector, a plasmid vector, an episomal vector, or the like.

The vector is preferably one in which the vector is not incorporated into the genome, or a vector in which the vector is temporarily incorporated into the genome but can be removed from the genome by an artificial operation.

For example, when the above-mentioned construct is incorporated into a transposon vector, it can be easily incorporated into the chromosome of a cell by introducing it into a cell to cause a transposase to act. In addition, by causing the transposase to act, the above-mentioned construct incorporated into the chromosome can be excised from the chromosome and removed without leaving a trace. The transposon may be, for example, piggyBac, Sleeping Beauty, Tol II, mariner, or the like.

Alternatively, after loxP sequences are disposed at both ends of the above-mentioned construct and iPS cells are established, Cre recombinase may be caused to act to remove the sequence sandwiched between the loxP sequences.

As the vector, an episomal vector is preferable. Examples of the episomal vector include a vector which is derived from EBV, SV40, or the like and contains a sequence required for autonomous replication within mammalian cells.

Examples of the sequence required for autonomous replication within mammalian cells include a replication initiation point that functions within mammalian cells, and a gene that encodes a protein that binds to a replication initiation point and controls replication.

Specifically, regarding the vector derived from EBV, a replication initiation point oriP and an EBNA-1 gene are exemplary examples. Regarding the vector of SV40, a replication initiation point ori and an SV40 large T antigen gene are exemplary examples.

Examples of methods of introducing the vector into cells include a lipofection method, a DEAE-dextran method, a calcium phosphate method, a microinjection method, an electroporation method, a gene gun method, and a viral vector method.

Examples of devices for performing the electroporation method include NEPA21 (Nepa Gene Co., Ltd.), 4D-Nucleofector (Lonza), Neon (Thermo Fisher Scientific), Gene Pulser Xcell (Bio-Rad Laboratories, Inc.), and ECM839 (BTX, Harvard Apparatus).

A reagent for transfection may be used as a method of introducing the vector into cells. As the reagent for transfection, it is possible to use, for example, Lipofectamine 2000 (Thermo Fisher Scientific), StemFect (STEMGEN S.p.A.), FuGENE 6/HD (Promega), CRISPRMAX (Thermo Fisher Scientific), jetPRIME Kit (Polyplus Transfection), DreamFect (OZ Biosciences), GenePorter 3000 (OZ Biosciences), a reagent for calcium phosphate method, and the like.

Subsequently, in the step (a), somatic cells of a pluripotency induction-resistant animal into which the reprogramming factor has been introduced are cultured in a neural stem cell culture medium. The neural stem cell culture medium preferably contains a MAP kinase inhibitor, a GSK3β inhibitor, and a TGFβ inhibitor.

The neural stem cell culture medium may further contain Leukemia Inhibitory Factor (LIF) as a differentiation inhibiting factor, and a basic fibroblast growth factor (bFGF) as a growth factor.

Examples of the GSK3β inhibitor include CHIR99021, SB-415286, SB-2167, indirubin-3'-Monoxime, and Kenpaullone, and among these, CHIR99021 and Kenpaullone are particularly preferable. In addition, the addition concentration of the GSK inhibitor to the medium is, for example, 0.1 to 10 μM, preferably 1 to 3 μM.

Examples of the TGF-β inhibitor include A83-01, SB-431542, SB-505124, SB-525334, SD-208, LY-36494, and SJN-2511. Among these, A83-01 is preferable. In addition, the addition concentration of the TGF-β inhibitor to the medium is, for example, 0.1 to 10 μM, preferably 0.5 to 1 μM.

The MAP kinase inhibitor may be, for example, one inhibiting constituent factors of the MAP kinase pathway such as MAPK, ERK, MEK, MEKK, ERK1, ERK2, Raf, MOS, p21ras, GRB2, SOS, JNK, c-jun, SAPK, JNKK, PAK, RAC, and p38.

Examples of the MAP kinase inhibitor include PD0325901, PD184352, VX-745, SB202190, anisomycin, PD98059, SB203580, U0126, AG126, apigenin, an HSP25 kinase inhibitor, 5-iodotubercidin, MAP kinase antisense oligonucleotide, control MAP kinase oligonucleotide, a MAP kinase cascade inhibitor, a MAP kinase inhibitor set 1, a MAP kinase inhibitor set 2, a MEK inhibitor set, olomoucine, iso-olomoucine, N9-isopropyl-olomoucine, a p38 MAP kinase inhibitor, PD169316, SB202474, SB202190 hydrochloride, SB202474 dihydrochloride, SB203580 sulfone, Ioto-SB203580, SB220025, SC68376, SKF-86002, Tyrphostin AG 126, U0124, U0125, and ZM336372 (refer to, for example, Japanese Patent No. 6218229). Among these, PD0325901 is preferable. In addition, the addition concentration of the MAP kinase inhibitor to the medium is, for example, 0.01 to 10 μM, preferably 0.03 to 1 μM.

Step (b)

In the present step, the induced neural stem cell-like cells obtained in the step (a) are cultured in a growth medium to obtain induced pluripotent stem cells.

As will be described later in Examples, induced pluripotent stem cells can be obtained by culturing the induced neural stem cell-like cells obtained in the step (a) in a growth medium. As the growth medium, a known medium for culturing ES cells can be used, but the growth medium is not limited thereto and may be any medium as long as it is suitable for culturing ES cells. As will be described later in Examples, the growth medium may contain bFGF (FGF2).

As will be described later in Examples, the growth medium may be a Dulbecco's modified Eagle's medium containing 20% Knockout serum replacement (KSR, Thermo Fisher Scientific) and 4 to 10 ng/mL bFGF.

Induced Pluripotent Stem Cells

In one embodiment, the present invention provides induced pluripotent stem cells produced by the production method described above.

As will be described later in Examples, the iPS cells of the present embodiment endogenously express OCT4, NANOG, SOX2, KLF4, LIN28, ZFP42, TRA-1-60, and SSEA4, which are pluripotent stem cell markers. In addition, the iPS cells of the present embodiment can be differentiated into endoderm, mesoderm, and ectoderm. In addition, the iPS cells of the present embodiment can form teratomas and differentiate into differentiated glandular epithelium, blood vessels, cartilage, fat cells, and nerve cells.

The iPS cells of the present embodiment are produced by expressing the above-mentioned reprogramming factor in somatic cells. Therefore, a gene encoding the reprogramming factor may be introduced.

However, for example, when a gene is introduced using an episomal vector or the like and the gene is removed in the middle of culturing, it is impossible to detect the reprogramming factor.

A difference in gene expression patterns and the like may be present between the iPS cells of the present embodiment and, for example, ES cells. However, it is uncertain whether or not such a difference is present, and in order to specify such a difference to specify the iPS cells of the present embodiment by gene expression patterns and the like, a significantly large number of trials and errors is required, which is substantially impossible. Therefore, it can be said that it is practical to specify the iPS cells of the present embodiment by them being produced by the above-mentioned production method.

The efficiency for establishing the iPS cells may be improved by bringing, in addition to the reprogramming factors described above, an efficiency-improving substance, which is capable of improving the efficiency for establishing known iPS cells, into contact with somatic cells of a pluripotency induction-resistant animal in the step (a).

As described in PCT International Publication No. WO2015/056804, examples of the substance for improving the efficiency of establishing iPS cells include, but are not limited to, a histone deacetylase (HDAC) inhibitor [for example, valproic acid (VPA) (Nat. Biotechnol., 26(7): 795-797 (2008)), small molecule inhibitors such as tricostatin A, sodium butyrate, MC 1293, and M344, and nucleic acid expression inhibitors such as siRNA and shRNA for HDAC (for example, HDAC1 siRNA Smartpool™ (Millipore), HuSH 29mer shRNA Constructs against HDAC1 (OriGene), and the like)], DNA methyltransferase inhibitors (for example, 5'-azacytidine) (Nat. Biotechnol., 26(7): 795-797 (2008)), G9a histone methyltransferase inhibitors [for example, small molecule inhibitors such as BIX-01294 (Cell Stem Cell, 2: 525-528 (2008)), and nucleic acid expression inhibitors such as siRNA and shRNA for G9a (for example, G9a siRNA (human) (Santa Cruz Biotechnology) and the like)], L-channel calcium agonist (for example, Bayk8644) (Cell Stem Cell, 3, 568-574 (2008)), UTF1 (Cell Stem Cell, 3, 475-479 (2008)), Wnt Signaling activators (for example, soluble Wnt3a) (Cell Stem Cell, 3, 132-135 (2008)), 2i/LIF (where 2i is an inhibitor of mitogen-activated protein kinase signalling and glycogen synthase kinase-3, PloS Biology, 6(10), 2237-2247 (2008)), ES cell-specific miRNA (for example, miR-302-367 cluster (Mol. Cell. Biol. doi: 10.1128/MCB.00398-08), miR-302 (RNA (2008) 14: 1-10), miR-291-3p, miR-294, and miR-295 (which are in Nat. Biotechnol. 27: 459-461 (2009))), 3'-phosphoinositide-dependent kinase-1 (PDK1) acitvators (for example, PS48 (Cell Stem Cell, 7: 651-655 (2010))), neuropeptide Y (WO2010/147395), and prostaglandins (for example, prostaglandin E2 and prostaglandin J2) (WO2010/068955).

In the above-described step (a) and step (b), the efficiency for establishing iPS cells may be improved by culturing somatic cells, iNSL cells, and iPS cells under hypoxic conditions. For example, a condition in which the oxygen concentration in the atmosphere when culturing cells is 18% or less is an exemplary example.

Kit

In one embodiment, the present invention provides a kit for producing induced pluripotent stem cells from somatic cells of a pluripotency induction-resistant animal, the kit including: a reprogramming factor including an OCT family, a SOX family, a KLF family, a MYC family, a LIN28 family, and a P53 function-inhibiting substance; and a neural stem cell culture medium containing a MAP kinase inhibitor, a GSK3β inhibitor, and a TGFβ inhibitor.

For example, iPS cells can be produced by introducing the reprogramming factor attached to the kit of the present embodiment into the somatic cells of a pluripotency induction-resistant animal and thereafter culturing the cells in the neural stem cell culture medium attached to the kit of the present embodiment. The above-mentioned MAP kinase inhibitor, GSK3β inhibitor, and TGFβ inhibitor may be the above-mentioned inhibitors in the production method.

The kit described above may further include a growth medium containing bFGF. The growth medium may be any medium as long as it can culture ES cells, and may be a known medium.

By using the kit of the present embodiment, induced pluripotent stem cells can be easily produced even in the case of somatic cells of a pluripotency induction-resistant animal.

The reprogramming factor attached to the kit of the present embodiment may further include one or more selected from the group consisting of a KDM family, a GUS family, and NANOG.

The reprogramming factor preferably includes the OCT family, the SOX family, the KLF family, the MYC family, the LIN28 family, the P53 function-inhibiting substance, the KDM family, the GLIS family, and NANOG.

The reprogramming factor described above may be a protein or a nucleic acid encoding the protein, as described above in the production method.

The P53 function-inhibiting substance attached to the kit of the present embodiment may be any substance as long as it is a substance suppressing the function of P53 protein or a substance suppressing the expression of a P53 gene, as described above in the production method.

The kit of the present embodiment may include a non-episomal vector having an expression construct for expressing the reprogramming factor and a nucleic acid encoding EBNA-1. Examples of the expression construct include one in which a gene fragment encoding a reprogramming factor is linked downstream of a promoter, as described above in the production method.

EXAMPLES

Hereinafter, the present invention will be described with reference to examples, but the present invention is not limited to the following examples.

Figure 56:
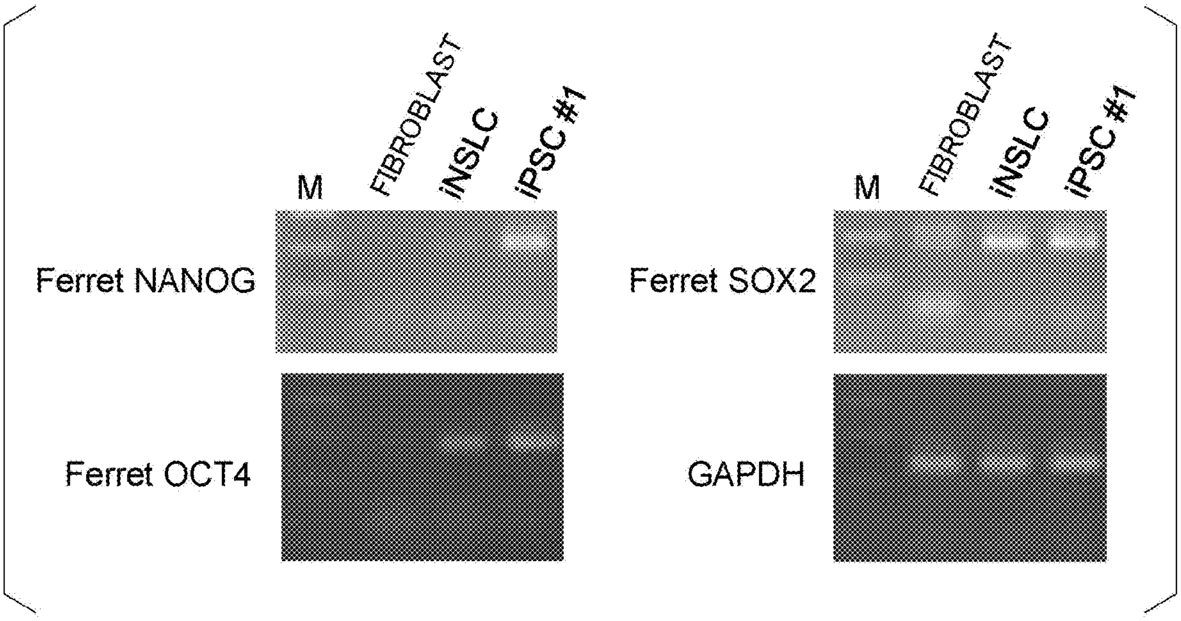
FIG. 56 shows diagrams showing the results of analyzing the expression of OCT4, SOX2, and NANOG in ferret iNSL cells and ferret iPS cells in Experimental Example 10.

In FIGS. 1 to 56 of Examples, E01F and E02M mean the line names of embryonic fibroblasts of marmosets, and I5061F and CM421F mean the line names of fibroblasts of adult marmosets. In addition, the description of these line names may mean cells from which iPS cells and iNSL cells are derived. In addition, EP-A means an EP-A vector set, and EP-B means an EP-B vector set. In addition, the description of EP-A and EP-B may mean a vector set introduced into cells.

Experimental Example 1

Introduction of Reprogramming Factor and Culture in Growth Medium

After introducing a reprogramming factor into somatic cells of a marmoset, the obtained cells were directly cultured in a growth medium (ES cell culture medium) without being cultured in a neural stem cell culture medium.

First, a reprogramming gene expression construct inserted into the vector described below was prepared. The reprogramming genes are OCT4, SOX2, KLF4, L-MYC, LIN28, mP53DD, KLF2, NANOG, KDM4D, and GLIS1.

OCT4, SOX2, KLF4, L-MYC, LIN28, KLF2, NANOG, KDM4D, and GLIS1 are human genes. An mP53DD protein is a dominant negative form in which the C-terminus of a mouse P53 protein has been deleted (Okita K et al., An Efficient Non-viral Method to Generate Integration-Free Human iPS Cells from Cord Blood and Peripheral Blood Cells, Stem Cells, vol. 31, 458-466, 2013).

Figure 2:
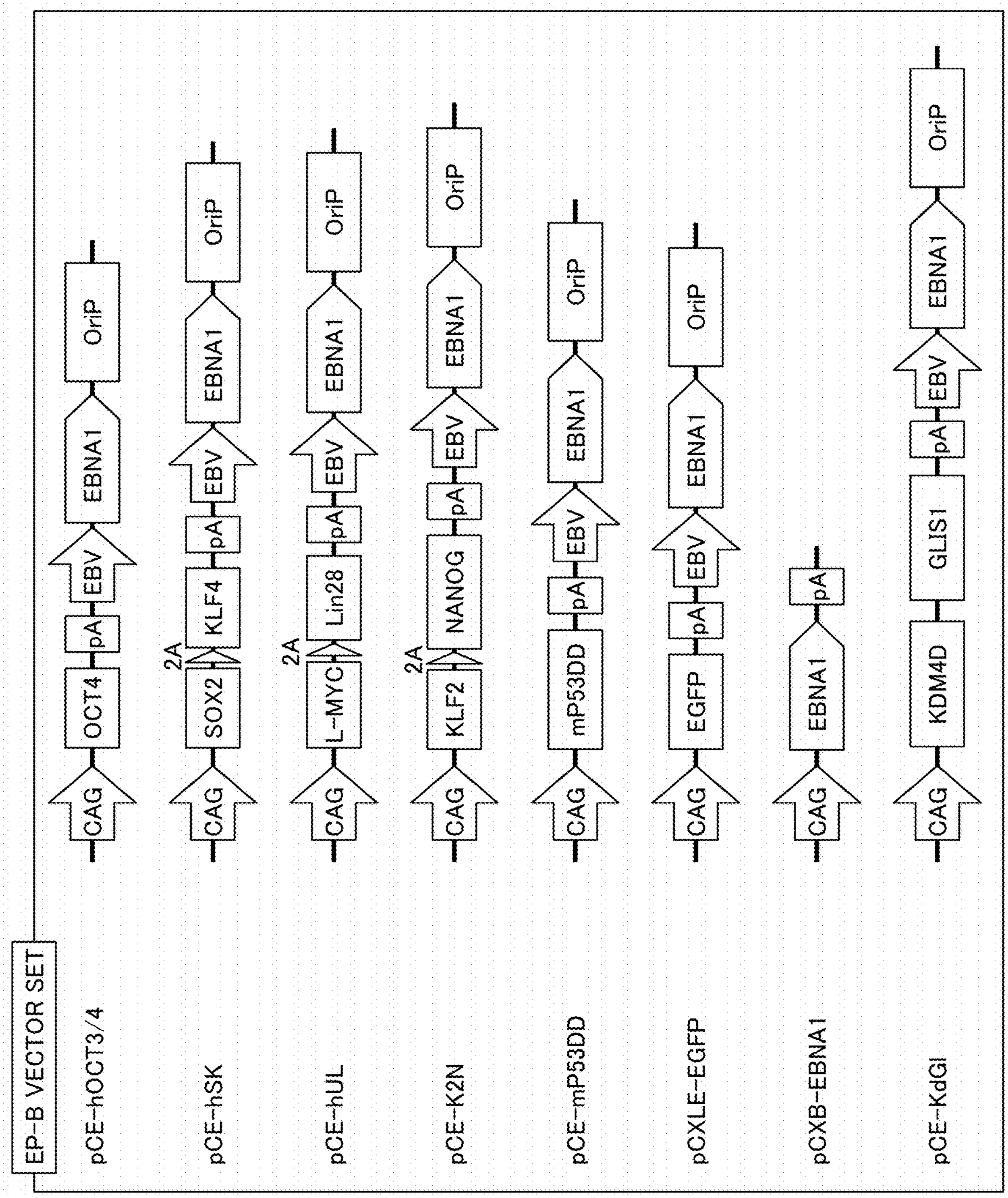
FIG. 2 is a diagram schematically showing an EP-B vector set for expressing a reprogramming factor.

Expression constructs introduced into the marmoset somatic cells are shown in FIGS. 1 and 2. The expression constructs have the structure described below.

pCE-hOCT3/4 expressing OCT4 has ORF of an OCT4 gene downstream of a CAG promoter, and further has ORF of an EBNA1 gene (EBV Nuclear Antigen 1) downstream of an EBV (Epstein-Barr Virus) promoter, and a replication origin point OriP of EBV.

pCE-hSK expressing SOX2 and KLF4 has ORF of SOX2, a 2A sequence of foot-and-mouth disease virus, and ORF of KLF4 downstream of a CAG promoter, and has ORF of an EBNA1 gene downstream of an EBV promoter and a replication origin point OriP of EBV.

pCE-hUL expressing L-MYC and LIN28 has ORF of L-MYC, a 2A sequence of foot-and-mouth disease virus, and ORF of LIN28 downstream of a CAG promoter, and has ORF of an EBNA1 gene downstream of an EBV promoter and a replication origin point OriP of EBV.

pCE-mP53DD expressing mP53DD has ORF of mP53DD downstream of a CAG promoter, and has ORF of an EBNA1 gene downstream of an EBV promoter and a replication origin point OriP of EBV.

pCXLE-EGFP expressing EGFP has ORF of EGFP downstream of a CAG promoter, and has ORF of an EBNA1 gene downstream of an EBV promoter and a replication origin point OriP of EBV.

pCXB-EBNA1 expressing EBNA1 has ORF of an EBNA1 gene downstream of a CAG promoter.

pCE-K2N expressing KLF2 and NANOG has ORF of KLF2, a 2A sequence of foot-and-mouth disease virus, and ORF of NANOG downstream of a CAG promoter, and has ORF of an EBNA1 gene downstream of an EBV promoter and a replication origin point OriP of EBV.

pCE-KdGI expressing KDM4D and GLIS1 has ORF of KDM4D, a 2A sequence of foot-and-mouth disease virus, and ORF of GLIS1 downstream of a CAG promoter, and has ORF of an EBNA1 gene downstream of an EBV promoter and a replication origin point OriP of EBV.

The EP-A vector set consists of pCE-hOCT3/4, pCE-hSK, pCE-hUL, pCE-mP53DD, pCXLE-EGFP, and pCXB-EBNA1.

The EP-B vector set consists of pCE-hOCT3/4, pCE-hSK, pCE-hUL, pCE-mP53DD, pCXLE-EGFP, pCXB-EBNA1, pCE-K2N, and pCE-KdGI.

As the growth medium, a Dulbecco's modified Eagle's medium (DMEM medium) containing 20% Knockout serum replacement (KSR, Thermo Fisher Scientific) and 4 to 10 ng/mL bFGF was used. The composition of the growth medium is shown in Table 3 below.

TABLE 3

| |
|---|
| DMEM medium |
| 20% KSR (Thermo Fisher Scientific) |
| 10 ng/mL bFGF |
| 1% NEAA (Thermo Fisher Scientific) |
| 2 mM L-glutamine |
| 0.1 mM 2-mercaptoethanol |

Figure 3:
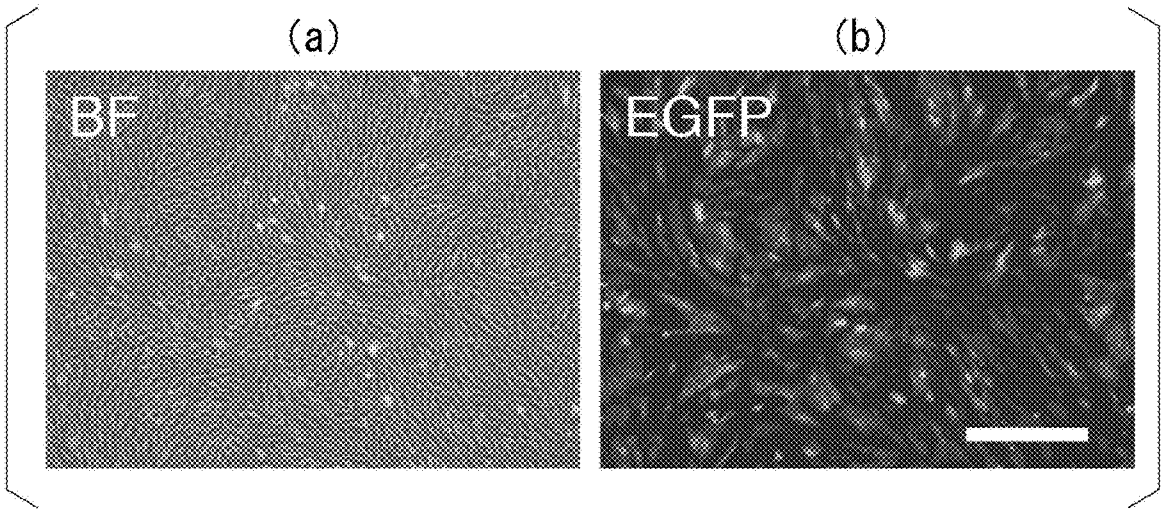
FIGS. 3(*a*) and 3(*b*) are photographs of cells in Experimental Example 1.

The EP-A vector set was introduced into marmoset embryonic fibroblasts (E01F), and culturing was directly performed in the growth medium without culturing in a neural stem cell culture medium. FIG. 3 shows the results.

FIG. 3(*a*) is a photograph obtained by imaging cells, into which the EP-A vector set was introduced and which were cultured in the growth medium for 4 days, in a bright field. FIG. 3(*b*) is a photograph obtained by imaging fluorescence of EGFP of cells into which the EP-A vector set was introduced and which were cultured in the growth medium for 4 days.

As a result, it was confirmed that the EP-A vector set was introduced into the marmoset cells and expressed EGFP which is a marker.

Figure 4:
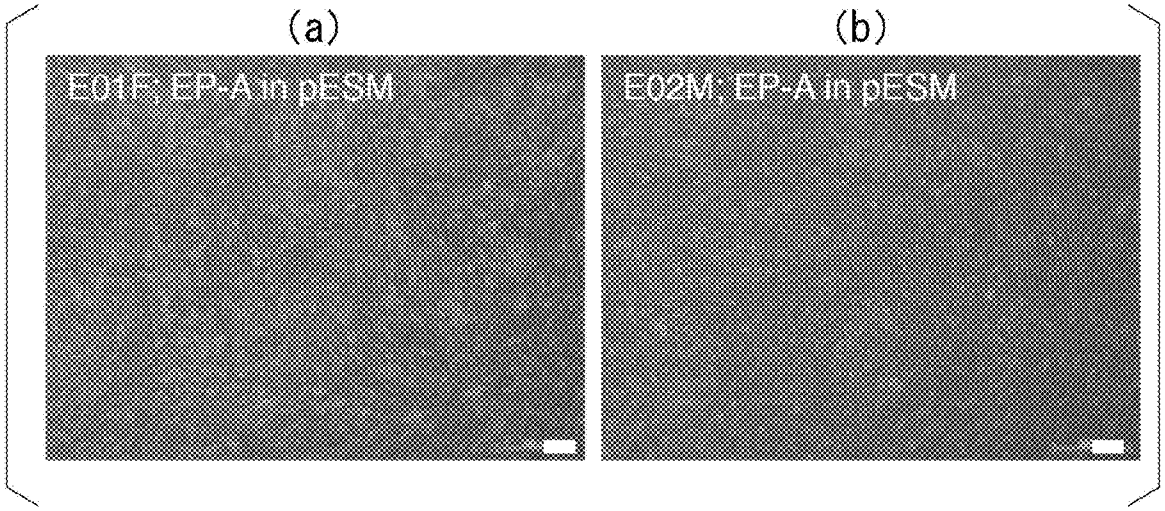
FIGS. 4(*a*) and 4(*b*) are photographs of cells in Experimental Example 1.

The EP-A vector set was introduced into marmoset embryonic fibroblasts (E01F and E02M), and the obtained cells were cultured in a medium for ES cell culture for 30 days. FIG. 4 shows the results. FIG. 4(*a*) is a photograph of cells in which the EP-A vector set was introduced into E01F and which were cultured in the growth medium for 30 days. FIG. 4(*b*) is a photograph of cells in which the EP-A vector set was introduced into E02M and which were cultured in the growth medium for 30 days.

As a result, even when the marmoset cells into which the EP-A vector set was introduced were directly cultured in the medium for ES cell culture without being cultured in a neural stem cell culture medium, a cell colony and cell mass could not be confirmed. From this result, it became clear that marmoset iPS cells are not formed even when the reprogramming factor is expressed in the marmoset cells and thereafter culturing is performed in the medium for ES cell culture.

Experimental Example 2

Introduction of Reprogramming Factor and Culture in Neural Stem Cell Culture Medium The reprogramming factor was introduced into marmoset embryonic fibroblasts, and culturing was performed in a neural stem cell culture medium to dedifferentiate marmoset cells.

Figure 5:
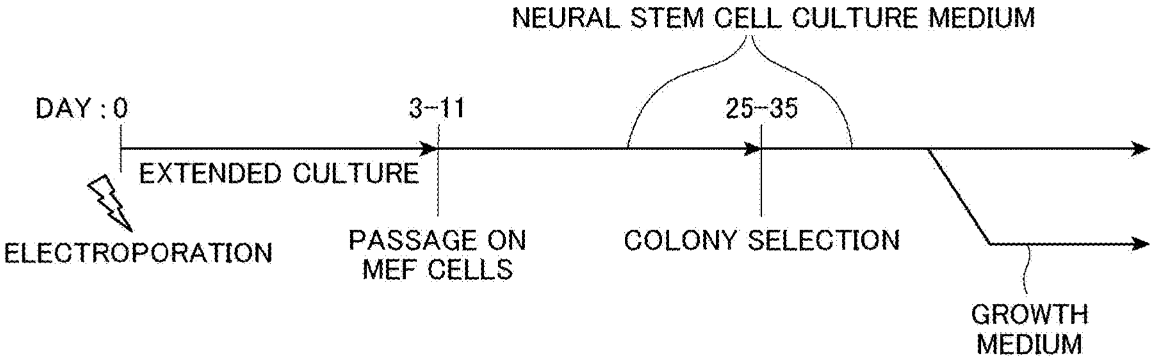
FIG. 5 is a diagram showing a process for establishing iPS cells from marmoset somatic cells.

The process for establishing iPS cells from marmoset somatic cells is shown in FIG. 5. First, a reprogramming factor expression construct was introduced into marmoset somatic cells by electroporation. Subsequently, the obtained cells were cultured in a Dulbecco's modified Eagle's medium containing 10% fetal bovine serum (FBS).

Subsequently, the obtained cells were cultured using MEF as a feeder cell. Subsequently, the obtained cells were cultured in a neural stem cell culture medium.

As the neural stem cell culture medium, a medium containing a MAP kinase inhibitor (PD0325901), a GSK3β inhibitor (CHIR99021), and a TGFβ inhibitor (A83-01) was used. The composition of the neural stem cell culture medium is shown in Table 4 below.

TABLE 4

| |
|---|
| DMEM/F12 medium:Neurobasal medium 1:1 |
| 1% N2 supplement (Thermo Fisher Scientific) |
| 2% B27 supplement (Thermo Fisher Scientific) |
| 0.05% AlubuMAX (Thermo Fisher Scientific) |
| 1% NEAA (Thermo Fisher Scientific) |
| 2 mM L-glutamine |
| 0.1 mM 2-mercaptoethanol |
| 1% KSR (Thermo Fisher Scientific) |
| 0.1 μM PD0325901 (CAS: 391210-10-9) |
| 1 μM CHIR99021 (CAS: 252917-06-9) |
| 0.5 μM A83-01 (CAS: 909910-43-6) |
| 10 μM Forskolin (CAS: 66575-29-9) |
| 10 ng/ml hLIF (Thermo Fisher Scientific) |

In Table 4, the DMEM/F12 medium is a medium in which DMEM and Ham's F-12 were mixed at the ratio of 1:1. The Neurobasal medium is manufactured by Thermo Fisher Scientific.

Figure 6:
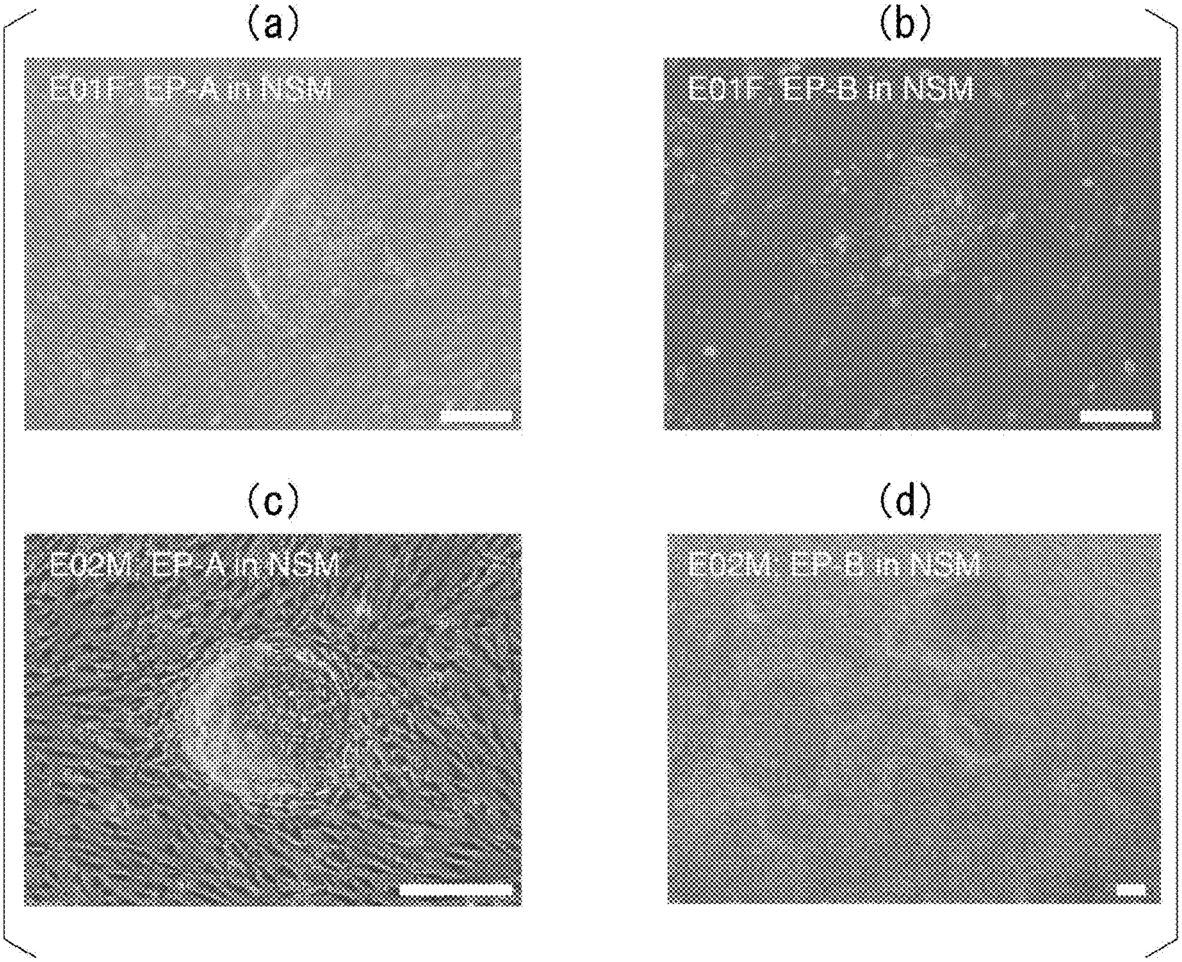
FIGS. 6(*a*) to 6(*d*) are photographs of iNSL cells in Experimental Example 2.

The EP-A vector set or EP-B vector set was introduced into marmoset embryonic fibroblasts (E01F and E02M), and culturing was performed in a neural stem cell culture medium. FIG. 6 shows the results.

FIG. 6(*a*) is a photograph of a colony formed by introducing the EP-A vector set into E01F and then culturing in the neural stem cell culture medium. FIG. 6(*b*) is a photograph of a colony formed by introducing the EP-B vector set into E01F and then culturing in the neural stem cell culture medium. FIG. 6(*c*) is a photograph of a colony formed by introducing the EP-A vector set into E02M and then culturing in the neural stem cell culture medium. FIG. 6(*d*) is a photograph of a colony formed by introducing the EP-A vector set into E02M and then culturing in the neural stem cell culture medium.

As a result, it became clear that all the marmoset cells into which the EP-A vector set or the EP-B vector set was introduced formed colonies.

Figure 7:
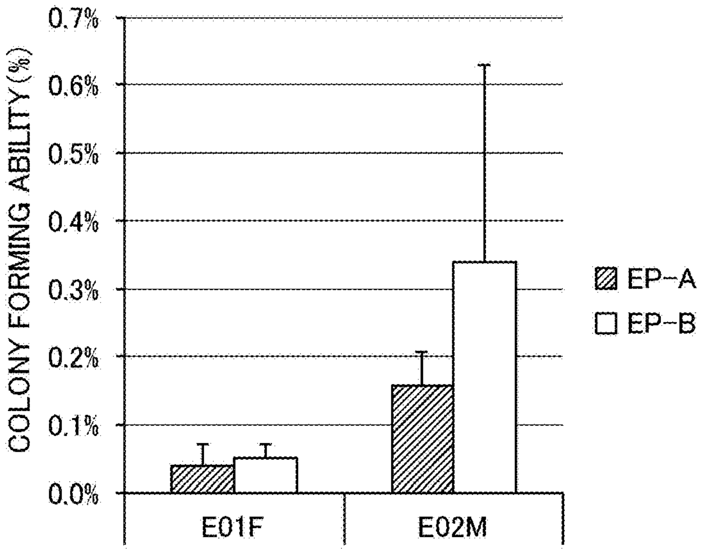
FIG. 7 is a graph showing the results of calculating a colony forming ability when marmoset embryonic fibroblasts were used in Experimental Example 2.

Furthermore, the colony forming ability of the marmoset cells into which the EP-A vector set or the EP-B vector set was introduced was calculated. FIG. 7 shows the results. FIG. 7 is a graph showing the results of calculating the colony forming ability when marmoset embryonic fibroblasts were used.

Figure 8:
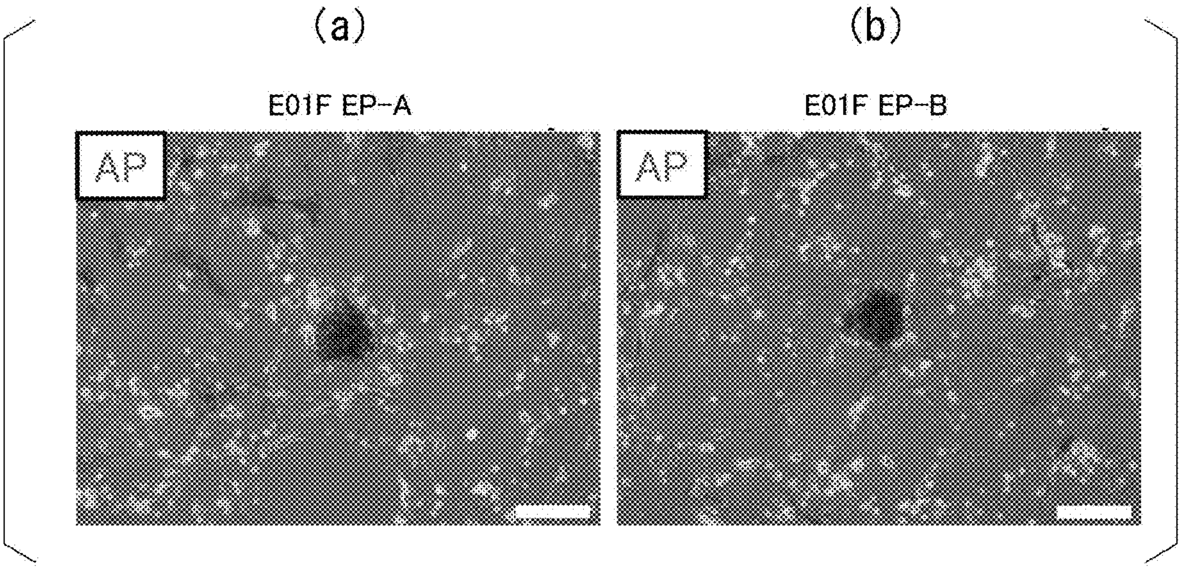
FIGS. 8(*a*) and 8(*b*) are diagrams showing the results of staining with alkaline phosphatase in Experimental Example 2.

In addition, the above-mentioned colonies were subjected to alkaline phosphatase staining. FIG. 8 shows the results.

FIG. 8(*a*) is a diagram showing the results of staining, with alkaline phosphatase, a colony obtained by introducing E01F into the EP-A vector set and culturing in a neural stem cell culture medium. FIG. 8(*b*) is a diagram showing the results of staining, with alkaline phosphatase, a colony obtained by introducing E01F into the EP-B vector set and culturing in a neural stem cell culture medium.

As a result, it became clear that the colonies of marmoset cells into which the EP-A vector set or the EP-B vector set was introduced were stained by alkaline phosphatase staining.

This result suggests that these colonies have been dedifferentiated and are in an undifferentiated state. Hereinafter, the cells forming these colonies may be referred to as induced Neural Stem Cell Like Cells (iNSLC), that is iNSL cells.

Experimental Example 3

Establishment of Marmoset iPS Cells

The reprogramming factor was introduced into marmoset embryonic fibroblasts, and culturing was performed in a neural stem cell culture medium. Thereafter, culturing was performed in a growth medium (ES cell culture medium) to establish marmoset iPS cells. As the neural stem cell culture medium and the growth medium, the same media as in Experimental Examples 1 and 2 were used.

The EP-A vector set or EP-B vector set was introduced into marmoset embryonic fibroblasts (E01F and E02M). Subsequently, the obtained cells were cultured in the neural stem cell culture medium, and then cultured in the growth medium.

Figure 9:
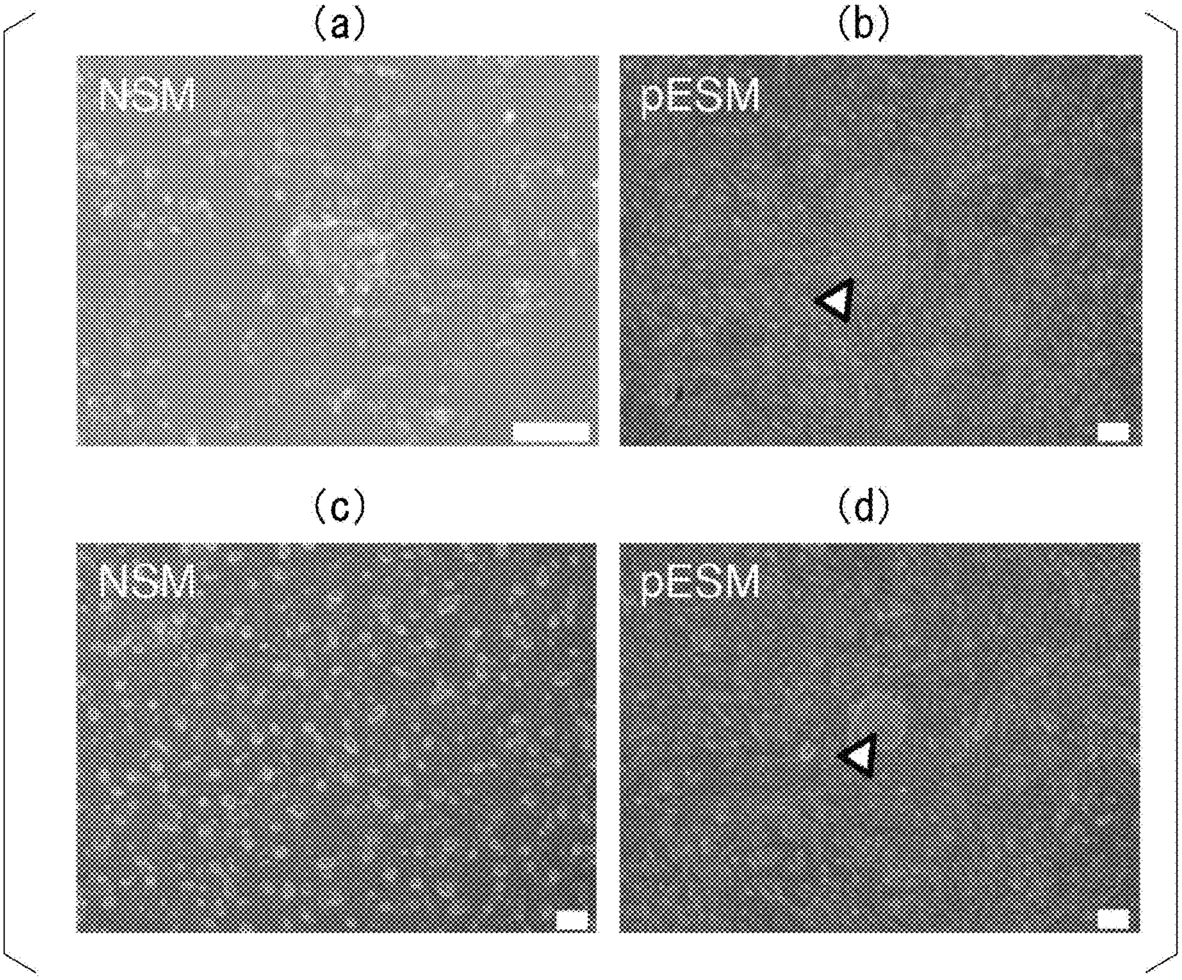
FIG. 9 shows photographs of iNSL cells and iPS cells in Experimental Example 3.

FIG. 9 shows the results. FIG. 9(*a*) is a photograph of a colony formed by introducing the EP-A vector set into marmoset embryonic fibroblasts (E01F) and culturing in the neural stem cell culture medium. FIG. 9(*b*) is a photograph of a colony formed by introducing the EP-A vector set into marmoset embryonic fibroblasts (E01F), culturing in the neural stem cell culture medium, and then culturing in the growth medium. FIG. 9(*c*) is a photograph of a colony formed by introducing the EP-B vector set into marmoset embryonic fibroblasts (E02M) and culturing in the neural stem cell culture medium. FIG. 9(*d*) is a photograph of a colony formed by introducing the EP-B vector set into marmoset embryonic fibroblasts (E02M), culturing in the neural stem cell culture medium, and then culturing in the growth medium.

As a result, when the reprogramming factor was introduced into marmoset embryonic fibroblasts, culturing was performed in the neural stem cell culture medium, and thereafter culturing was performed in the growth medium, colonies having the shape similar to colonies formed by ES cells were observed.

Figure 10:
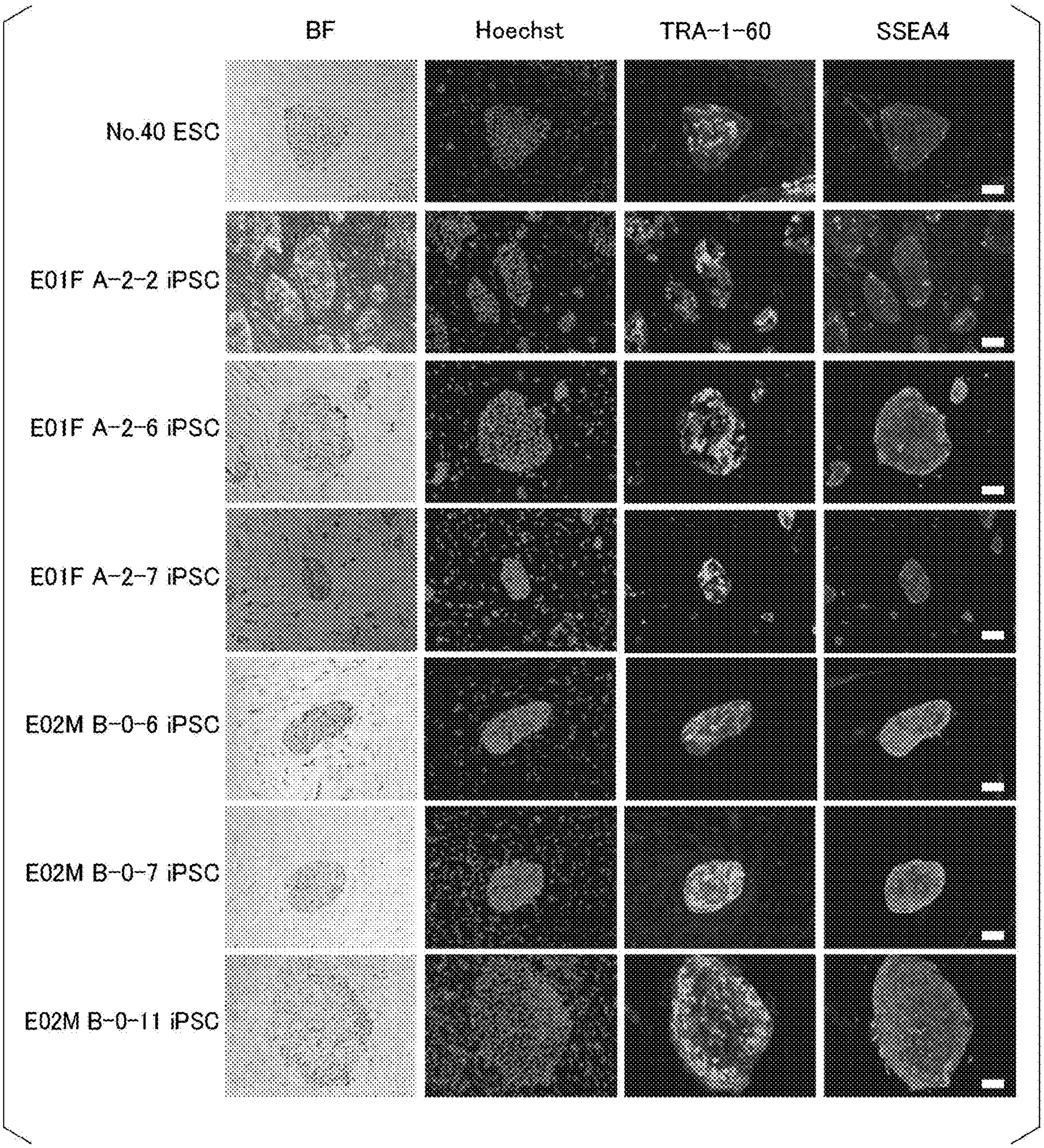
FIG. 10 shows diagrams showing the results of analyzing the expression of ES cell markers in marmoset iPS cells in Experimental Example 3.

Subsequently, the colonies of marmoset ES cells (No. 40 ESC) and the above-mentioned marmoset iPS cells (A-2-2, A-2-6, and A-2-7 derived from E01F, and B-0-6, B-0-7, and B-0-11 derived from E02M) were subjected to Hoechst staining and immunostaining using an anti-TRA-1-60 antibody and an anti-SSEA4 antibody. TRA-1-60 and SSEA4 are genes expressed in ES cells. FIG. 10 shows the results.

FIG. 10 shows diagrams showing the results of analyzing the expression of ES cell markers in marmoset iPS cells. As a result, it became clear that these marmoset iPS cells express TRA-1-60 and SSEA4 as in the case of ES cells.

Figure 11:
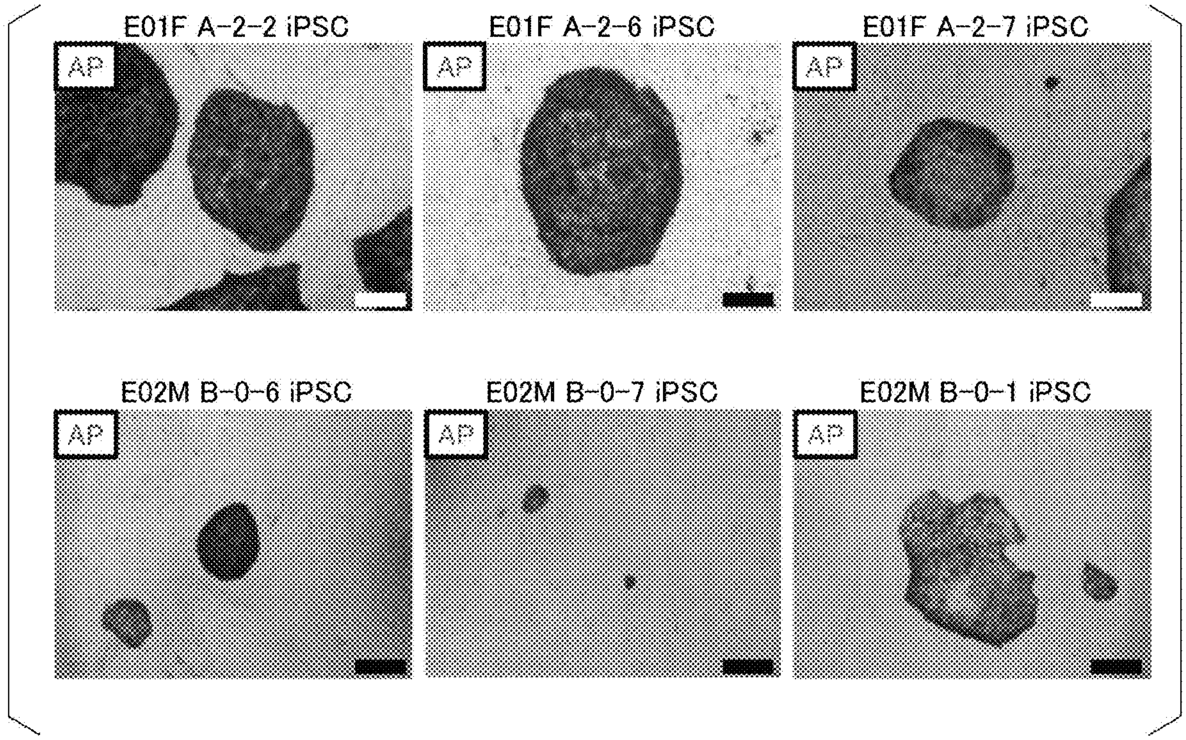
FIG. 11 shows diagrams showing the results of subjecting marmoset iPS cells to alkaline phosphatase staining in Experimental Example 3.

Subsequently, the colonies of the above-mentioned marmoset iPS cells were subjected to alkaline phosphatase staining. FIG. 11 shows the results. FIG. 11 shows diagrams showing the results of subjecting marmoset iPS cells to alkaline phosphatase staining. As a result, it became clear that these colonies were stained by alkaline phosphatase staining in the same manner as undifferentiated cells.

Figure 12:
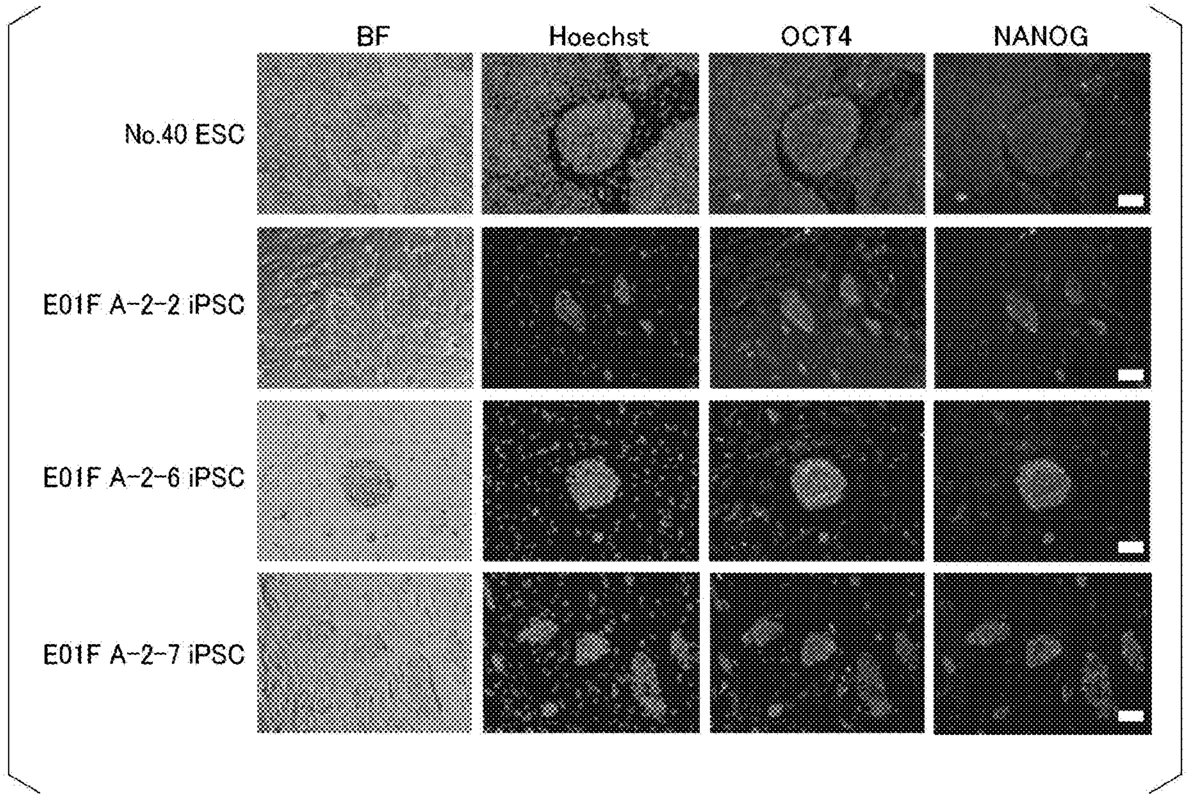
FIG. 12 shows diagrams showing the results of analyzing the expression of ES cell markers in marmoset iPS cells in Experimental Example 3.

Subsequently, the colonies of the above-mentioned marmoset iPS cells were subjected to Hoechst staining and immunostaining using an anti-OCT4 antibody and an anti-NANOG antibody. FIG. 12 shows the results. FIG. 12 shows diagrams showing the results of analyzing the expression of ES cell markers in marmoset iPS cells. As a result, it became clear that these marmoset iPS cell colonies expressed OCT4 and NANOG as in the case of ES cells.

Figure 13:
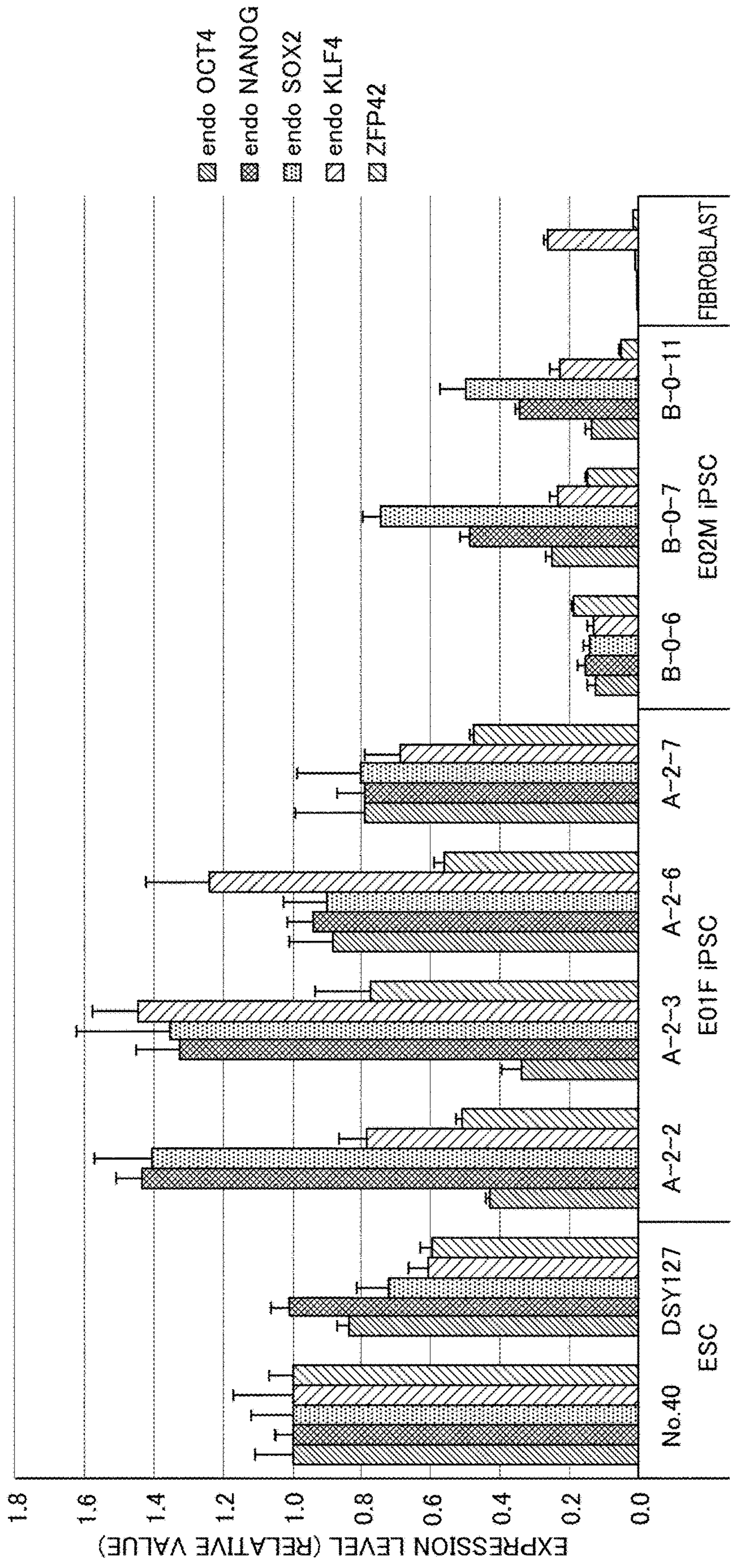
FIG. 13 shows diagrams showing the results of analyzing the expression of ES cell markers in marmoset iPS cells in Experimental Example 3.
Figure 14:
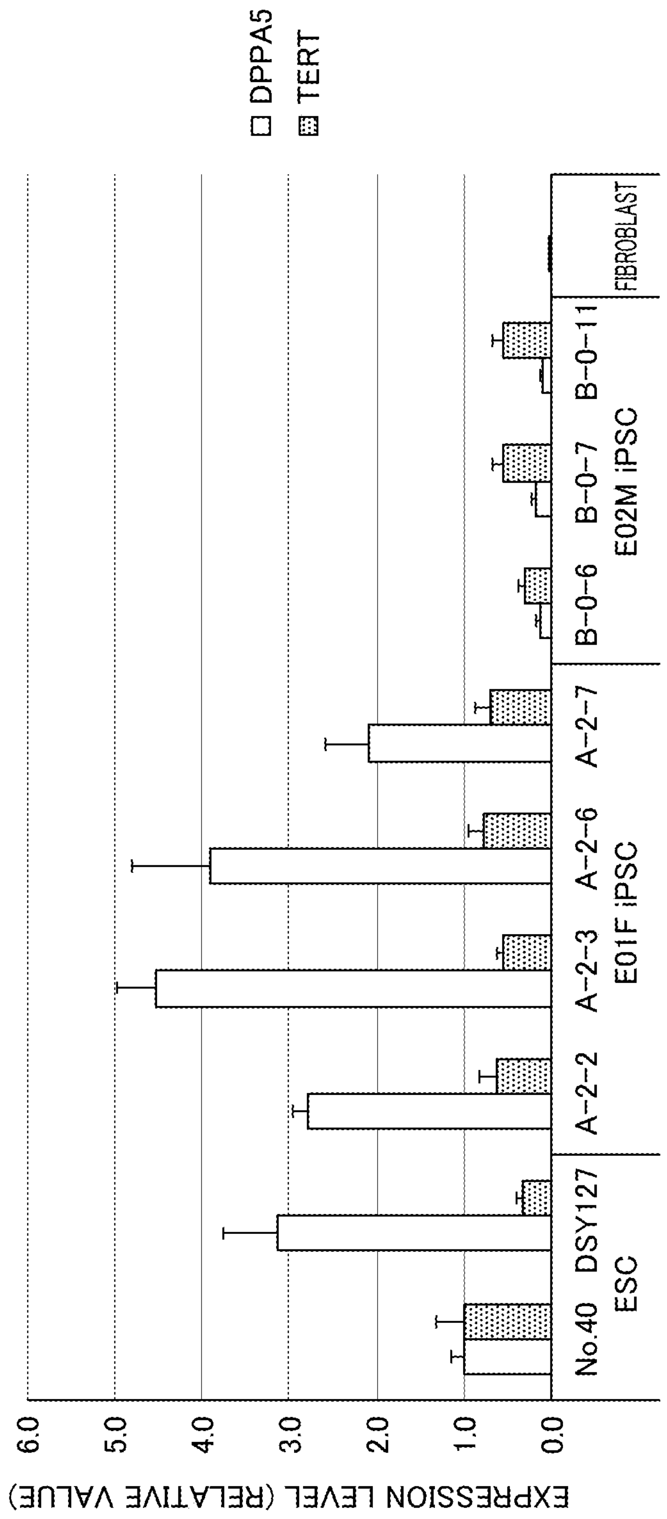
FIG. 14 shows diagrams showing the results of analyzing the expression of ES cell markers in marmoset iPS cells in Experimental Example 3.

Subsequently, for the above-mentioned marmoset iPS cells, marmoset ES cells (No. 40, DSY127), and marmoset embryonic fibroblasts, the expression of endogenous OCT4, endogenous NANOG, endogenous SOX2, and endogenous KLF4 gene, and the expression of a Zinc finger protein 42 (ZFP42) gene, a Developmental Pluripotency Associated 2 (DPPA) gene, and a Telomerase Reverse Transcriptase (TERT) gene were analyzed by qRT-PCR. FIG. 13 and FIG. 14 show the results.

FIG. 13 and FIG. 14 show diagrams showing the results of analyzing the expression of ES cell markers in marmoset iPS cells. As a result, it became clear that the marmoset iPS cells endogenously express the OCT4, NANOG, SOX2, KLF4, DRPA5, ZFP42, and TERT genes as in the case of the marmoset ES cells.

Figure 15:
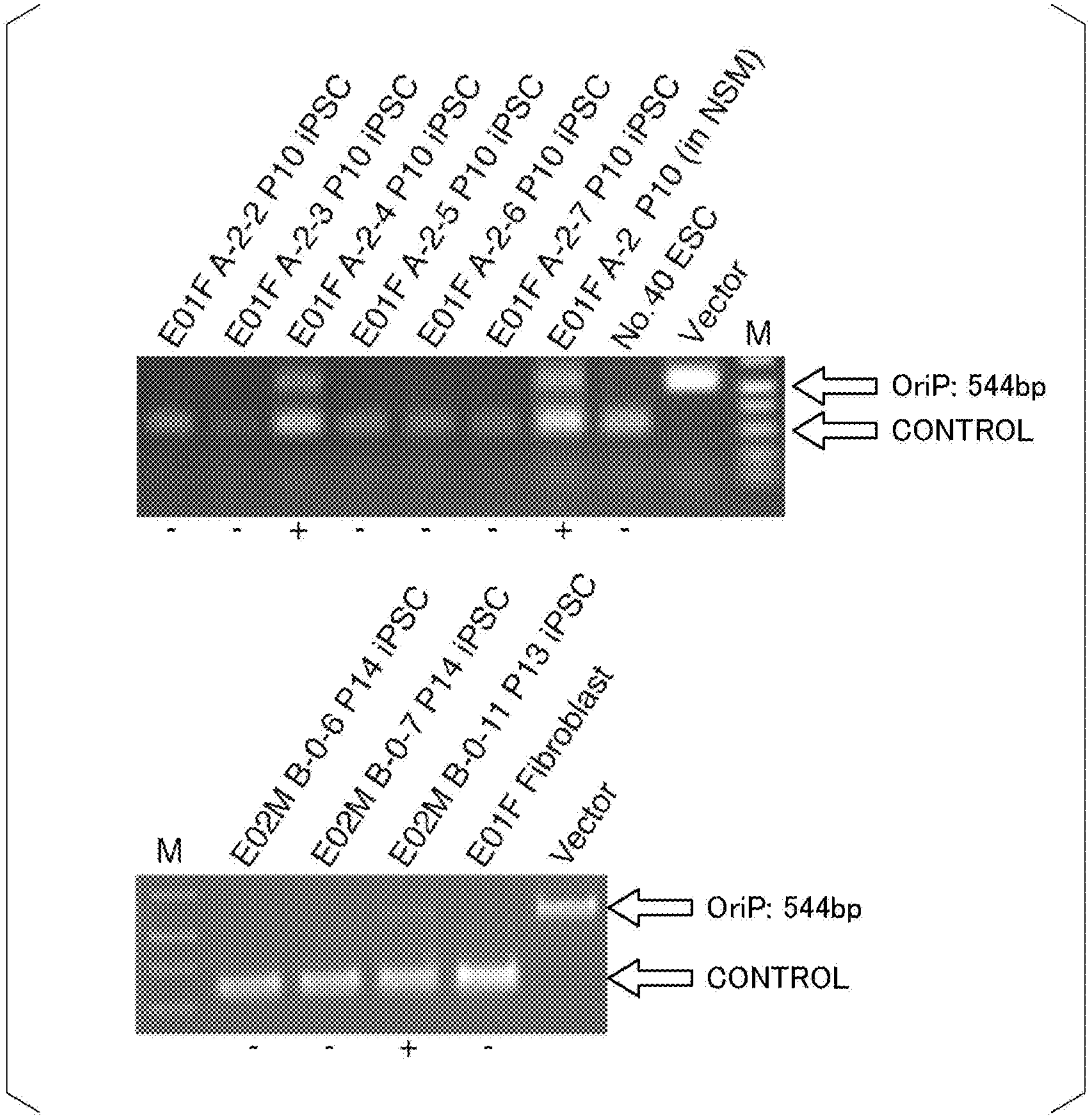
FIG. 15 shows diagrams showing the results of analyzing the presence or absence of an expression vector in marmoset iPS cells in Experimental Example 3.

Subsequently, whether or not the vector contained in the EP-A vector set or the EP-B vector set remained in the marmoset iPS cells was analyzed by a PCR method. FIG. 15 shows the results. FIG. 15 shows diagrams showing the results of analyzing the presence or absence of an expression vector in marmoset iPS cells.

As a result, regarding E01F A-2-2 iPSC, E01F A-2-3 iPSC, E01F A-2-5 iPSC, E01F A-2-6 iPSC, E01F A-2-7 iPSC, E02M B-0-6 iPSC, and E02M B-0-7 iPSC, it became clear that the EP-A vector set or the EP-B vector set did not remain in the cells.

Based on the above results, it became clear that, when marmoset cells into which the EP-A vector set or the EP-B vector set was introduced were cultured in the neural stem cell culture medium and thereafter cultured in the growth medium, the marker gene of ES cells is expressed even when the vector set is lost.

Experimental Example 4

Pluripotency of Marmoset iPS Cells

The marmoset iPS cells obtained in Experimental Example 3 were differentiated into endoderm, mesoderm, and ectoderm, and the expression of marker genes in each of the germ layers was analyzed to verify the pluripotency of the marmoset iPS cells.

First, the marmoset iPS cells (A-2-2, A-2-6, A-2-7, and B-0-7) were suspension-cultured and differentiated into each of the germ layers.

Figure 16:
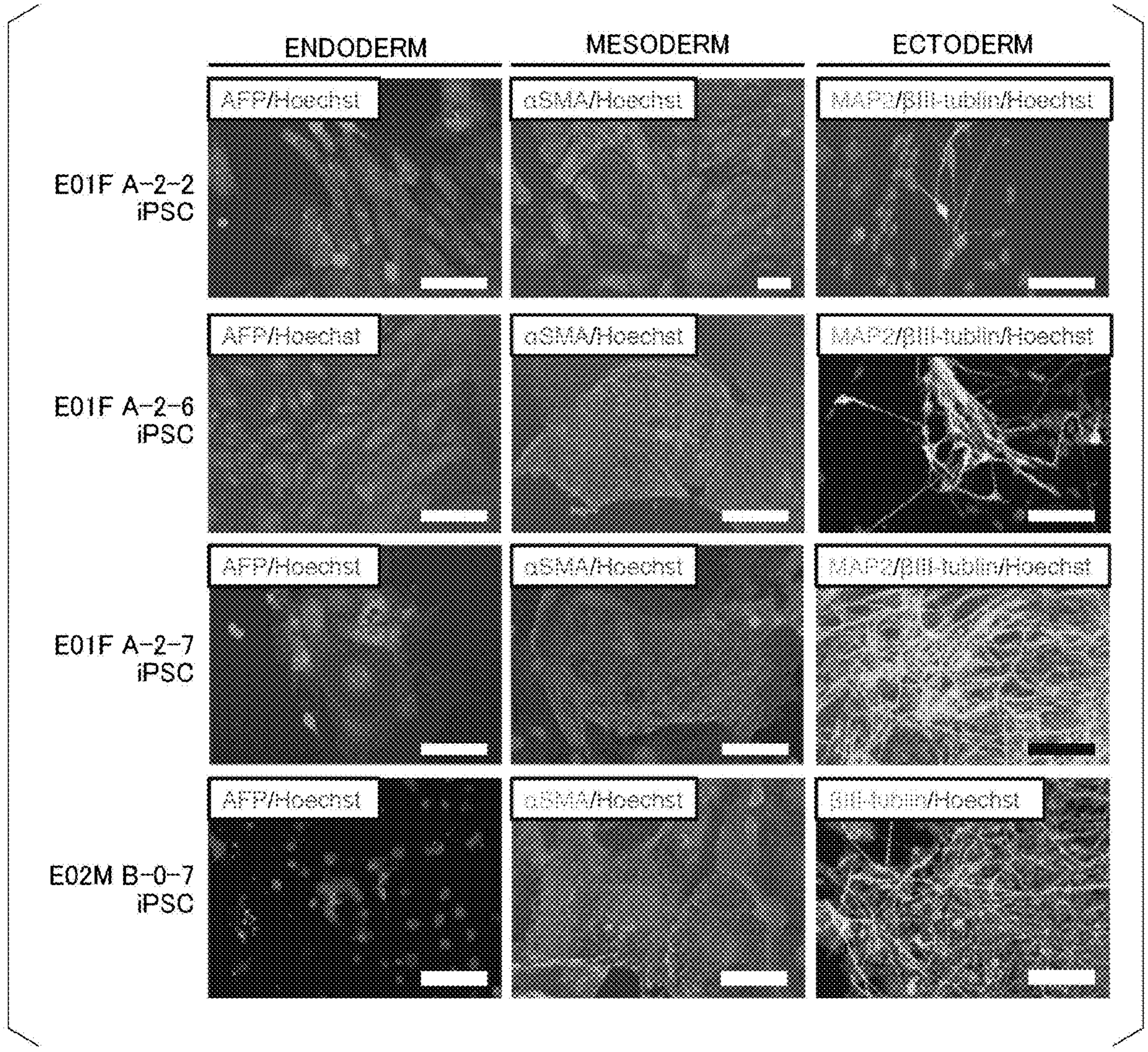
FIG. 16 shows diagrams showing the results of analyzing the expression of markers in three germ layers differentiated from marmoset iPS cells in Experimental Example 4.

Subsequently, the expression of Alpha-fetoprotein (AFP) for endoderm, α-Smooth muscle actin (αSMA) for mesoderm, and Microtubule associated protein 2 (MAP2) and βIII-tubulin for ectoderm was analyzed using antibodies against each of the proteins. Furthermore, at the same time, Hoechst staining was also performed. FIG. 16 shows the results.

FIG. 16 shows diagrams showing the results of analyzing the expression of markers in three germ layers differentiated from marmoset iPS cells. As a result, it became clear that each of the germ layers formed from the marmoset iPS cells expresses a marker gene characteristic of each of the germ layers.

Figure 17:
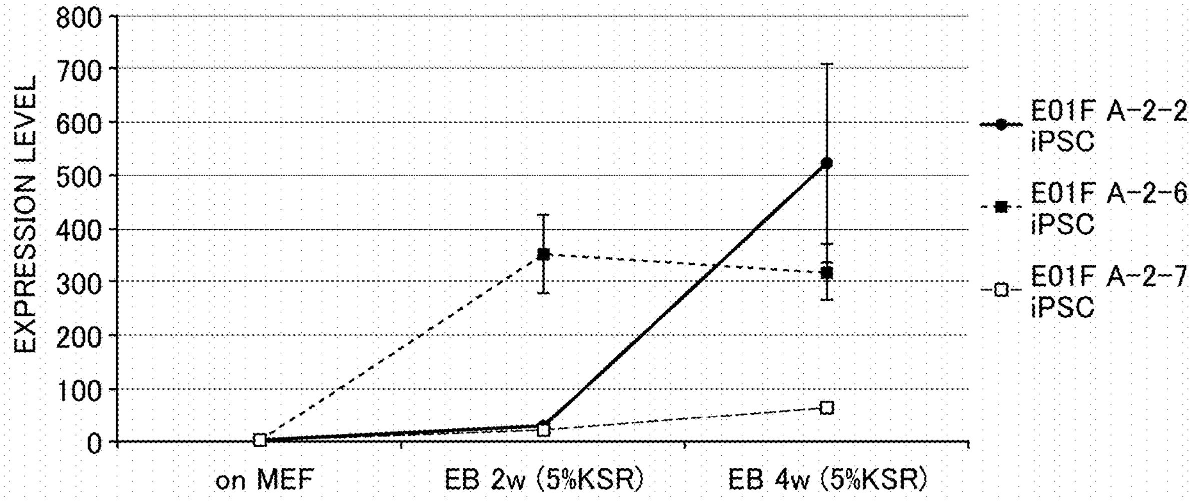
FIG. 17 is a diagram showing the results of analyzing the expression of AFP expressed by marmoset iPS cells cultured in a KSR medium in Experimental Example 4.
Figure 18:
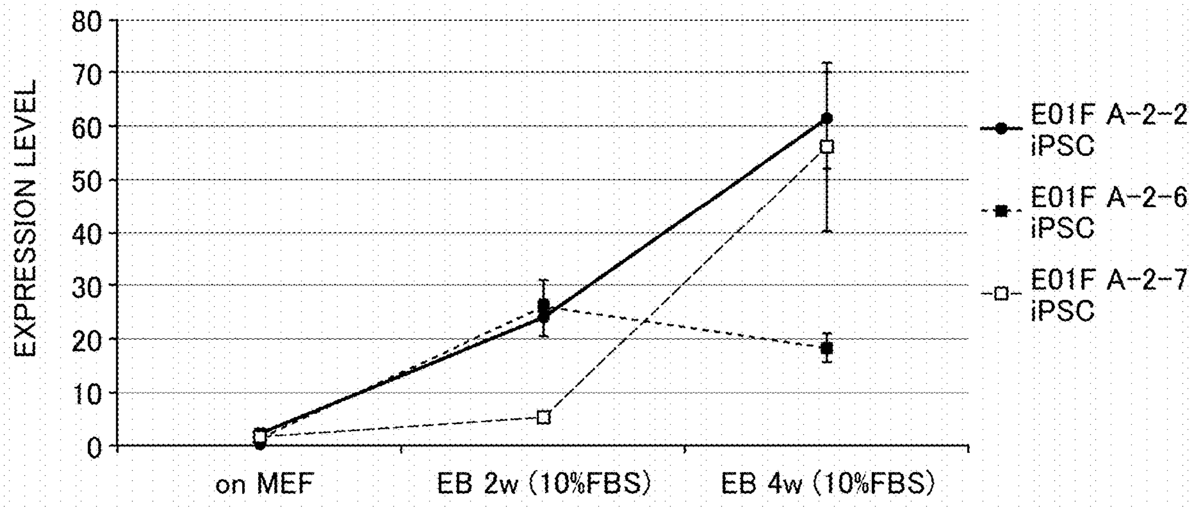
FIG. 18 is a diagram showing the results of analyzing the expression of AFP expressed by marmoset iPS cells cultured in a medium containing FBS in Experimental Example 4.

In addition, after culturing the embryoid body formed from the marmoset iPS cells for 2 weeks or 4 weeks using a KnockOut Serum Replacement Medium (KSR medium) or a medium containing 10% fetal bovine serum, the expression of AFP was analyzed by qRT-PCR. FIG. 17 and FIG. 18 show the results.

FIG. 17 is a diagram showing the results of analyzing the expression of AFP expressed by marmoset iPS cells cultured in the KSR medium. FIG. 18 is a diagram showing the results of analyzing the expression of AFP in marmoset iPS cells cultured in the medium containing FBS.

In FIGS. 17 and 18, EB indicates the embryoid body, 2 w indicates after 2 weeks, and 4 w indicates after 4 weeks. As a result, it became clear that the embryoid body formed from the marmoset iPS cells expresses AFP.

Furthermore, the obtained marmoset iPS cells (A-2-2, A-2-7, and B-0-7) were injected into the testicle of an immunodeficient mouse (NOD/SCID), and after 2 to 3 months, teratomas formed inside the testicle were excised to observe tissues differentiated from endoderm, mesoderm, and ectoderm.

Figure 19:
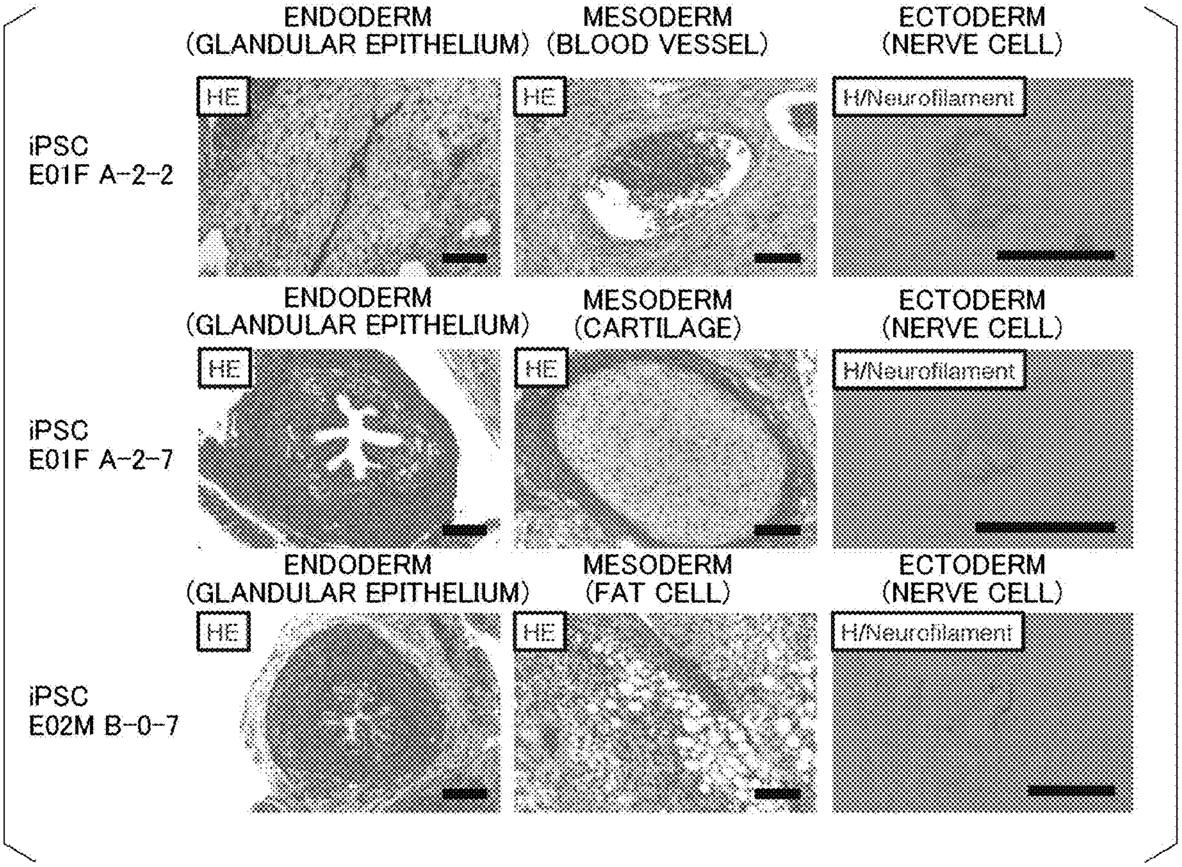
FIG. 19 shows diagrams showing the results of analyzing teratomas formed from marmoset iPS cells in Experimental Example 4.

More specifically, glandular epithelium differentiated from the endoderm, and blood vessels, cartilage, and fat cells differentiated from the mesoderm were observed by hematoxylin and eosin staining (HE staining), and nerve cells differentiated from the ectoderm were observed by HE staining and immunostaining with an antibody against neurofilament 200 kDa. FIG. 19 shows the results.

FIG. 19 shows diagrams showing the results of analyzing teratomas formed from marmoset iPS cells. As a result, it became clear that the differentiated glandular epithelium, blood vessels, cartilage, fat cells, and nerve cells are formed in the teratomas.

Experimental Example 5

Establishment of iPS Cells from Adult Marmoset Cells

The EP-A vector set or the EP-B vector set was introduced into adult marmoset fibroblasts, and culturing was performed in a neural stem cell culture medium to establish iNSL cells. Furthermore, iPS cells were established by culturing the obtained iNSL cells in a growth medium.

Figure 20:
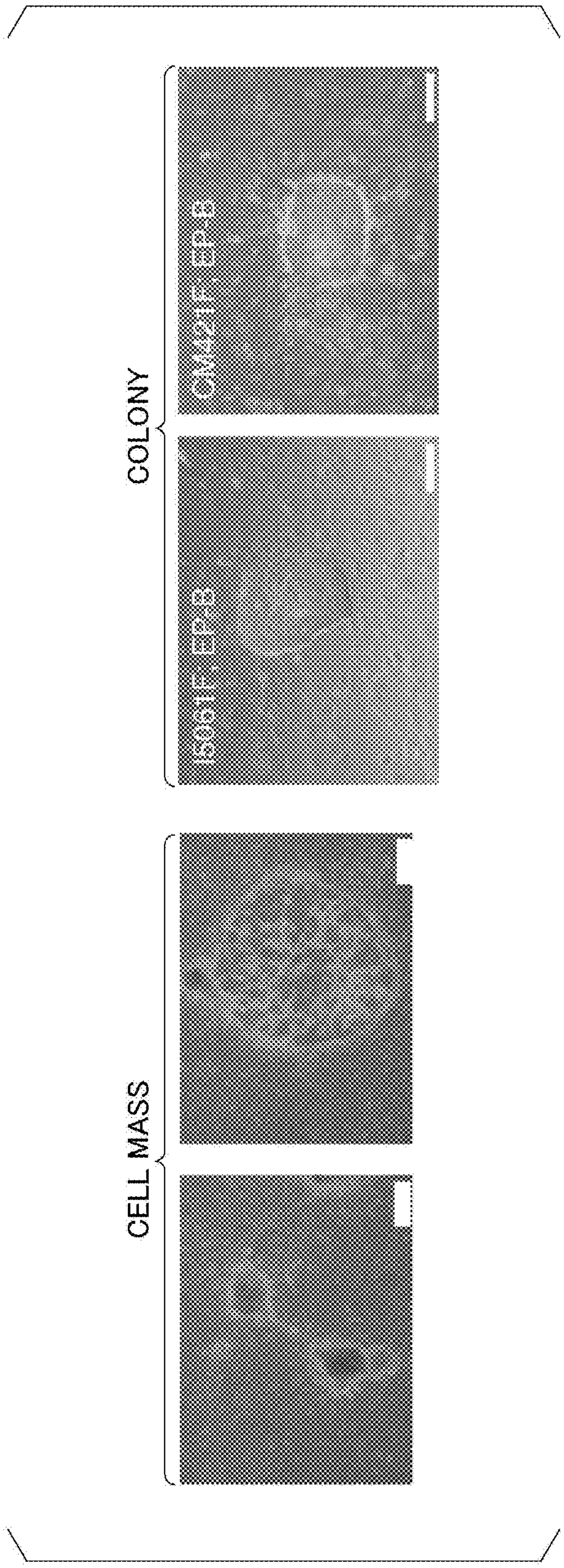
FIG. 20 shows photographs of iNSL cells derived from fibroblasts of an adult marmoset in Experimental Example 5.

Using the adult marmoset fibroblasts (15061F and CM421F), marmoset iNSL cells were established by the method described above. FIG. 20 shows the results. FIG. 20 shows photographs of iNSL cells derived from fibroblasts of an adult marmoset.

As a result, it became clear that iNSL cells derived from adult marmoset fibroblasts form cell masses and colonies.

Figure 21:
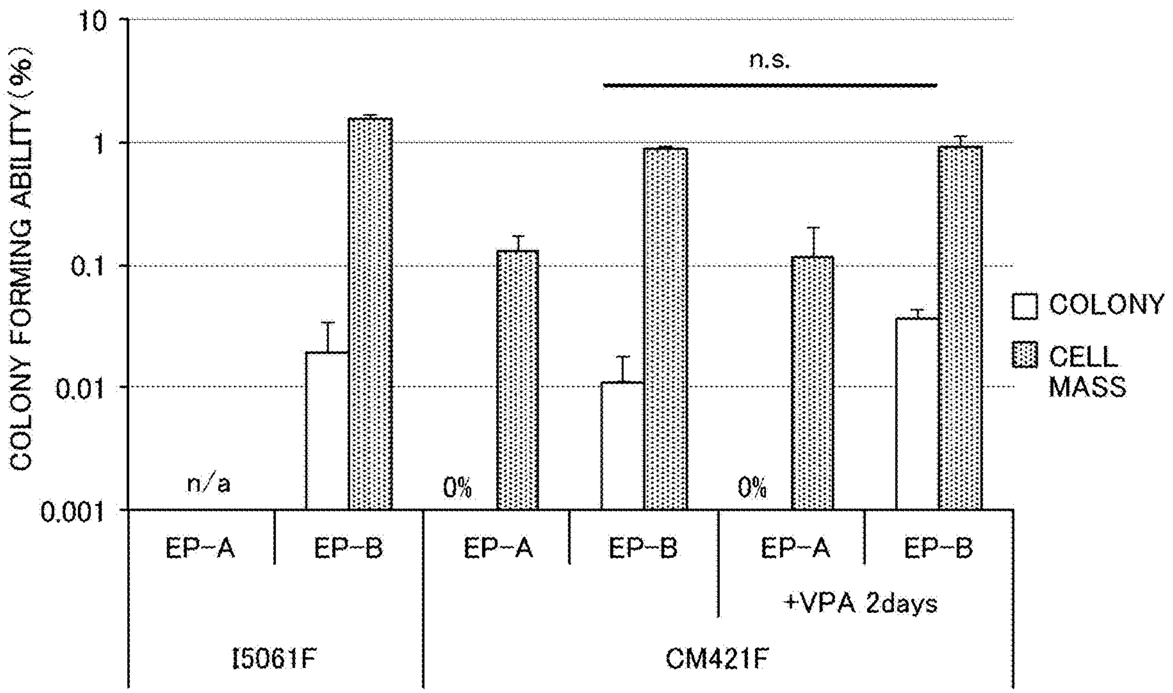
FIG. 21 is a diagram showing the colony forming ability of iNSL cells derived from fibroblasts of an adult marmoset in Experimental Example 5.

Subsequently, the colony forming ability of iNSL cells derived from adult marmoset fibroblasts was calculated. FIG. 21 shows the results. FIG. 21 is a diagram showing the colony forming ability of iNSL cells derived from fibroblasts of an adult marmoset.

In FIG. 21, "+ VPA" indicates that a histone deacetylase inhibitor (Valproic Acid) was added for 2 days. As a result, it became clear that iNSL cells can be established with good reproducibility from the adult marmoset fibroblasts.

Figure 22:
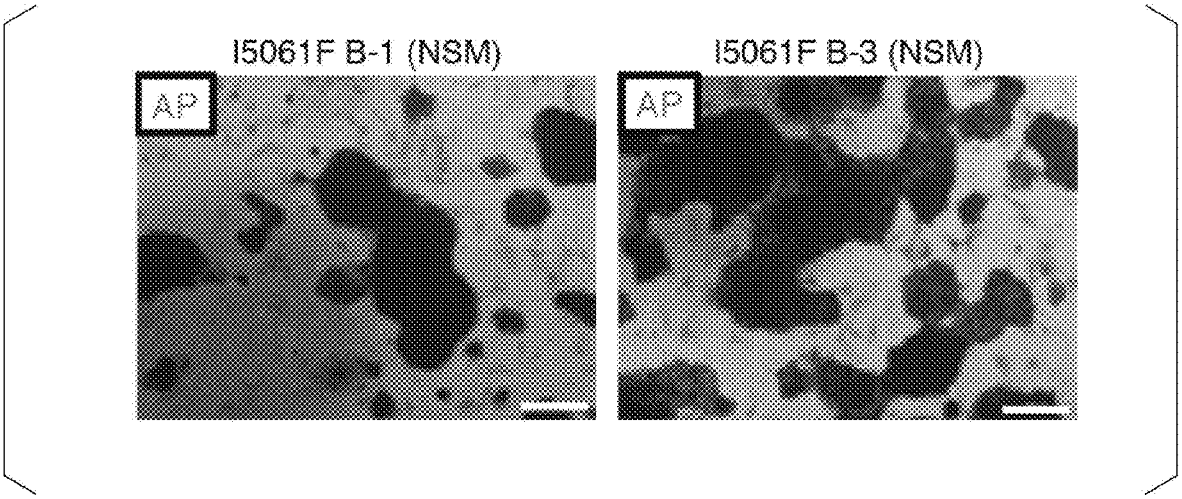
FIG. 22 shows diagrams showing the results of alkaline phosphatase staining of iNSL cells derived from fibroblasts of an adult marmoset in Experimental Example 5.

Subsequently, alkaline phosphatase staining was performed on the above-mentioned iNSL cells. FIG. 22 shows the results. FIG. 22 shows diagrams showing the results of alkaline phosphatase staining of iNSL cells derived from fibroblasts of an adult marmoset.

As a result, it became clear that iNSL cells derived from adult marmoset fibroblasts express alkaline phosphatase. That is, it became clear that iNSL cells derived from adult marmoset fibroblasts have an undifferentiation property.

Figure 23:
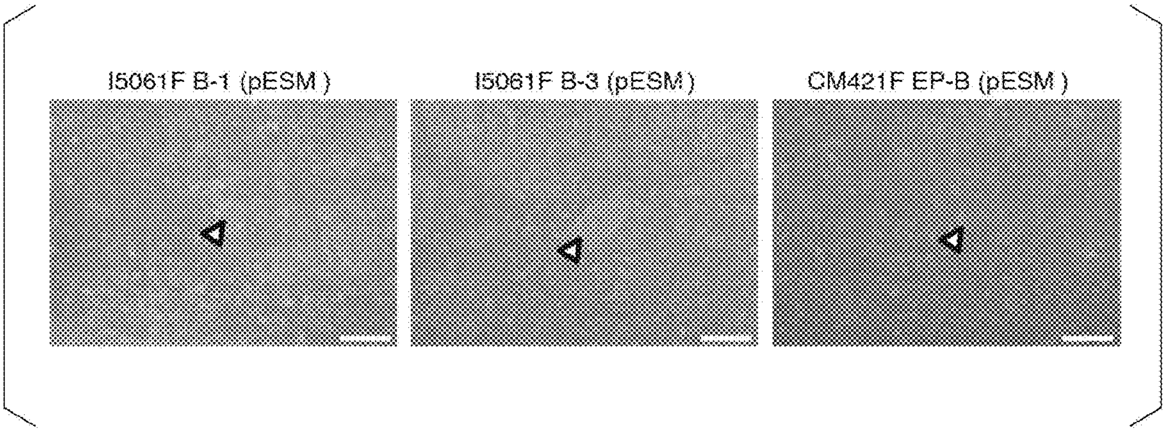
FIG. 23 shows photographs of colonies of marmoset iPS cells derived from fibroblasts of an adult marmoset in Experimental Example 5.

Subsequently, in the same manner as in Experimental Example 3, the above-mentioned iNSL cells were cultured in a growth medium to obtain marmoset iPS cells. FIG. 23 shows the results. FIG. 23 shows photographs of colonies of marmoset iPS cells derived from fibroblasts of an adult marmoset. As a result, it became clear that the marmoset iPS cells cultured in the growth medium form colonies similar to the colonies of ES cells.

Figure 24:
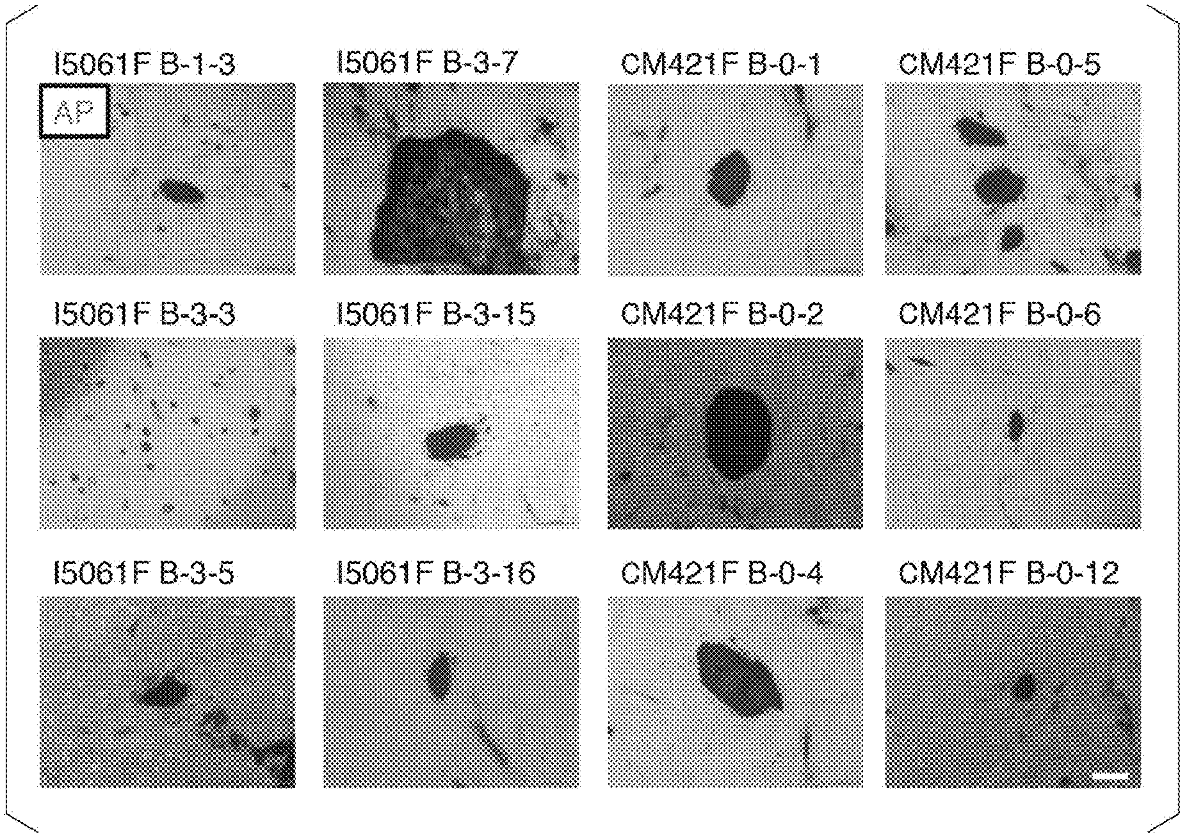
FIG. 24 shows diagrams showing the results of alkaline phosphatase staining of iPS cells derived from fibroblasts of an adult marmoset in Experimental Example 5.

Subsequently, the obtained marmoset iPS cells were subjected to alkaline phosphatase staining. FIG. 24 shows the results. FIG. 24 shows diagrams showing the results of alkaline phosphatase staining of iPS cells derived from fibroblasts of an adult marmoset. As a result, it was suggested that the established marmoset iPS cells were undifferentiated.

Figure 25:
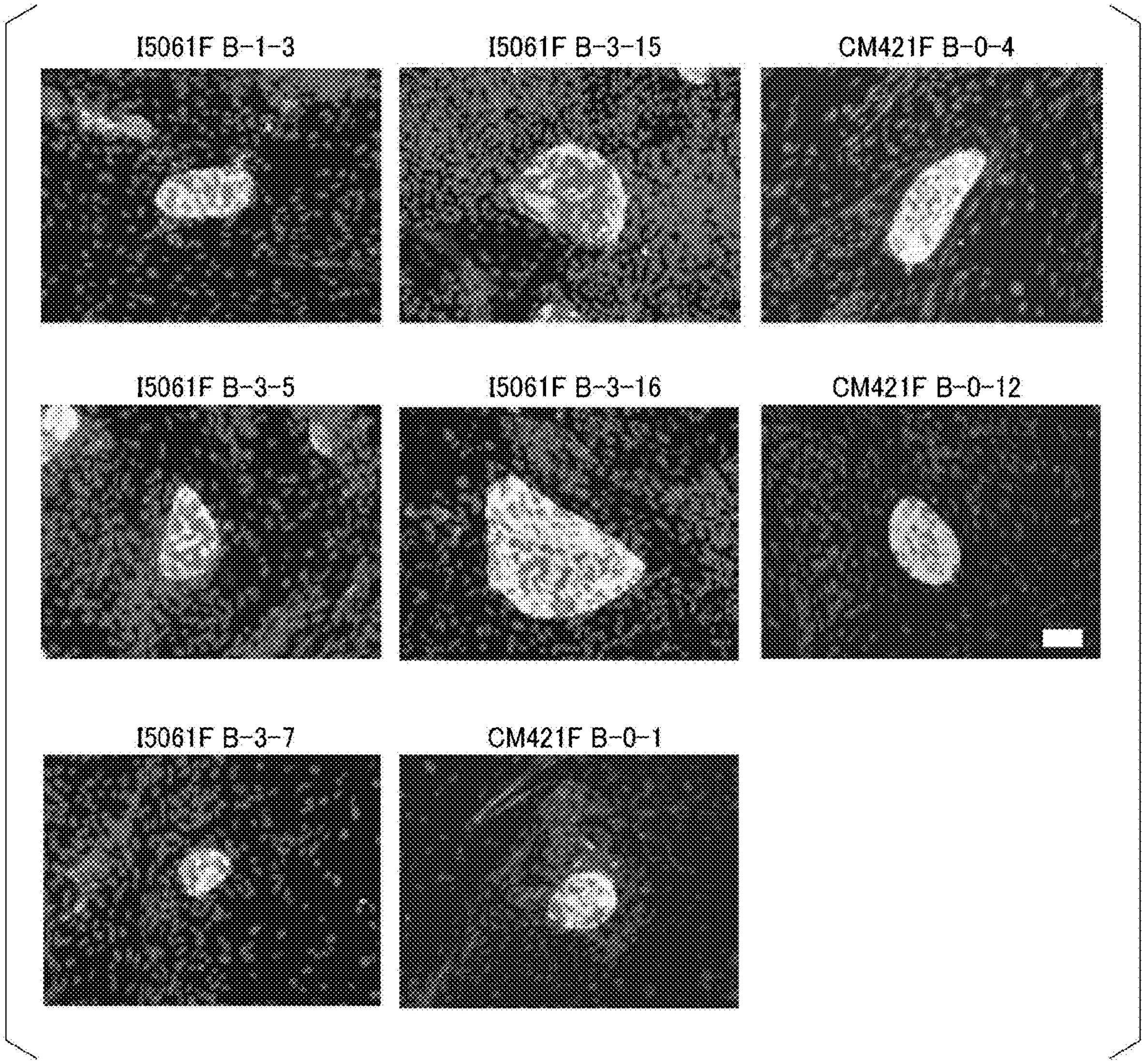
FIG. 25 shows diagrams showing the results of analyzing the expression of ES cell markers in marmoset iPS cells derived from fibroblasts of an adult marmoset in Experimental Example 5.
Figure 26:
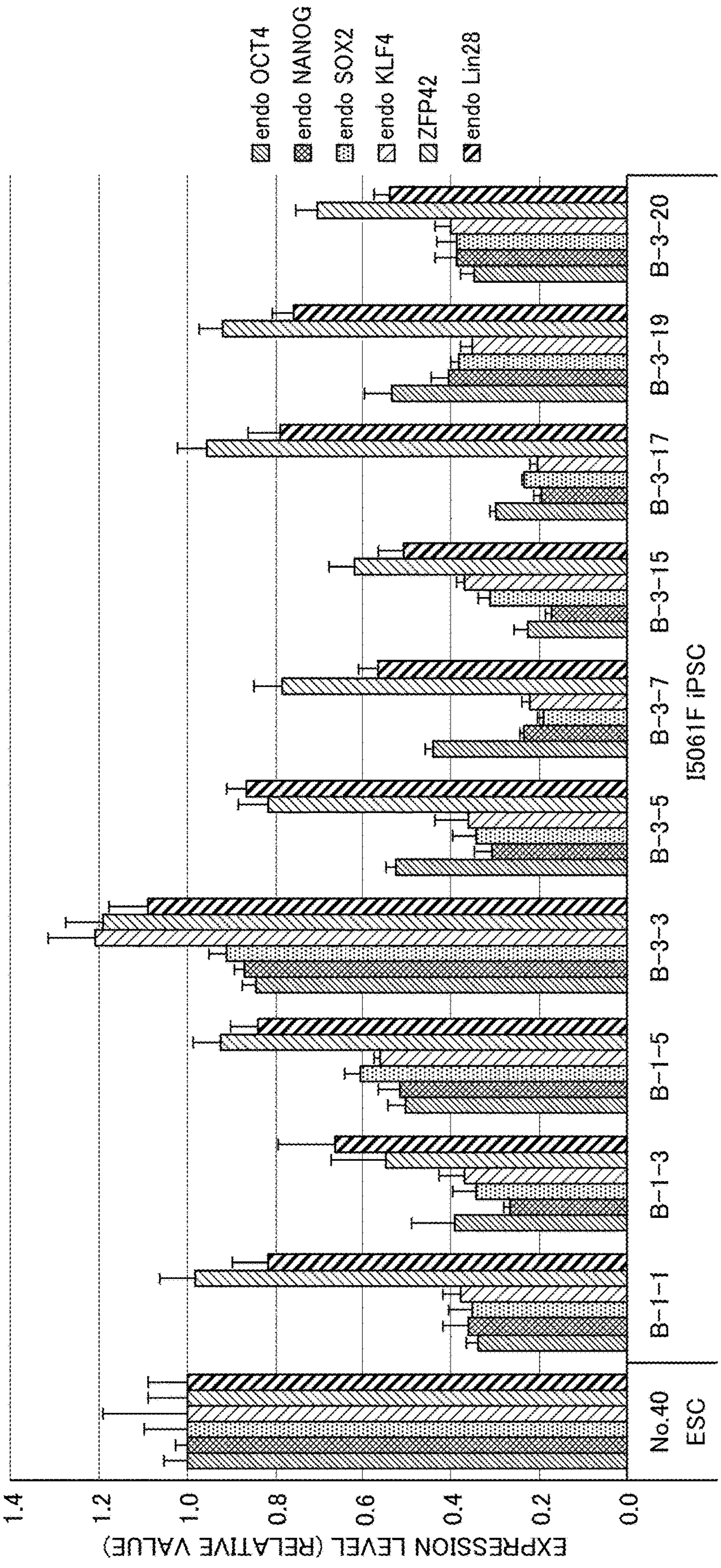
FIG. 26 is a diagram showing the results of analyzing the expression of ES cell markers in marmoset iPS cells derived from fibroblasts of an adult marmoset in Experimental Example 5.
Figure 27:
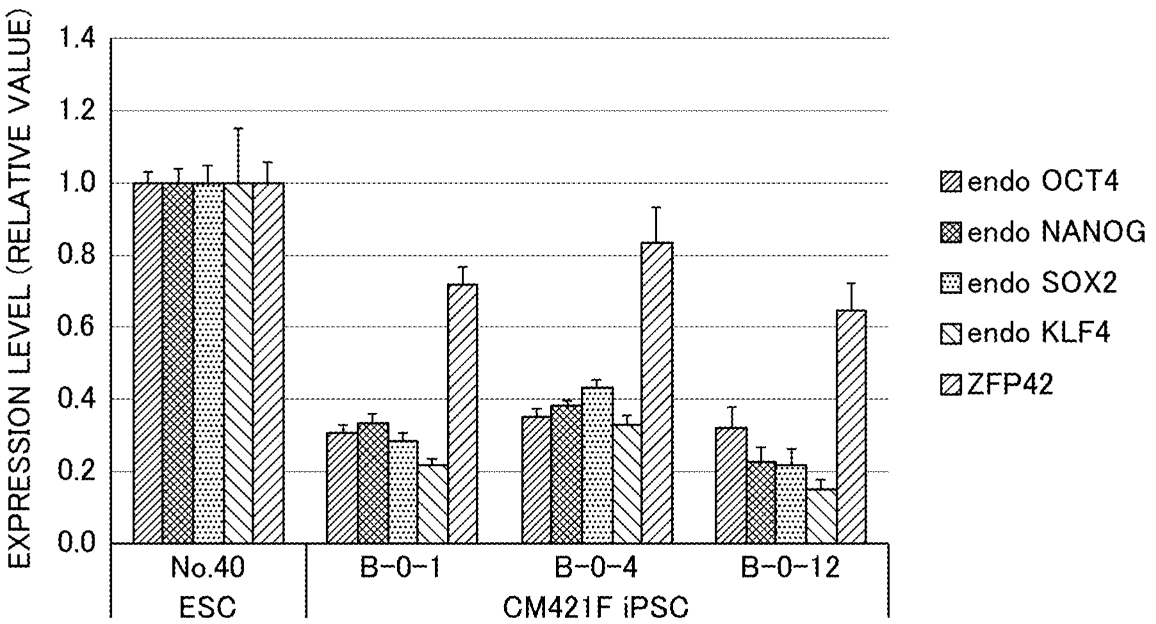
FIG. 27 is a diagram showing the results of analyzing the expression of ES cell markers in marmoset iPS cells derived from fibroblasts of an adult marmoset in Experimental Example 5.
Figure 28:
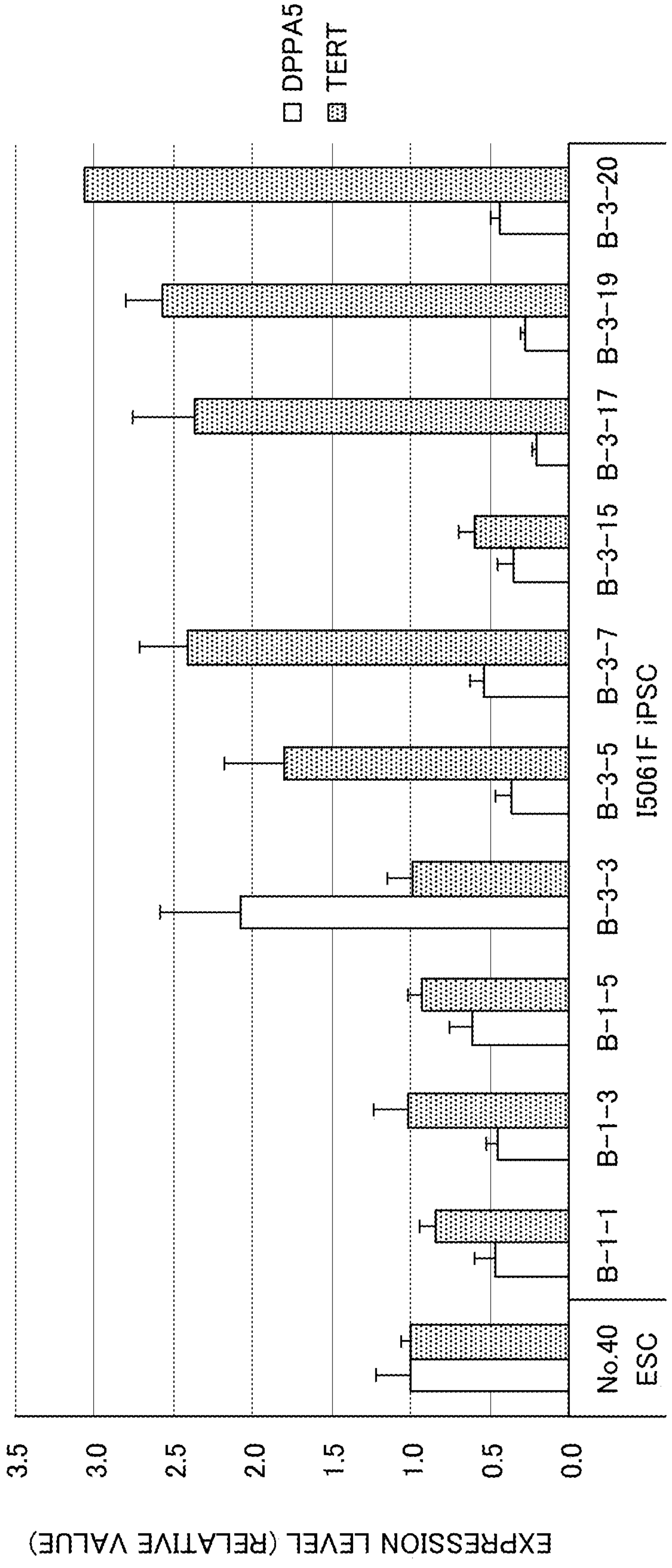
FIG. 28 is a diagram showing the results of analyzing the expression of ES cell markers in marmoset iPS cells derived from fibroblasts of an adult marmoset in Experimental Example 5.
Figure 29:
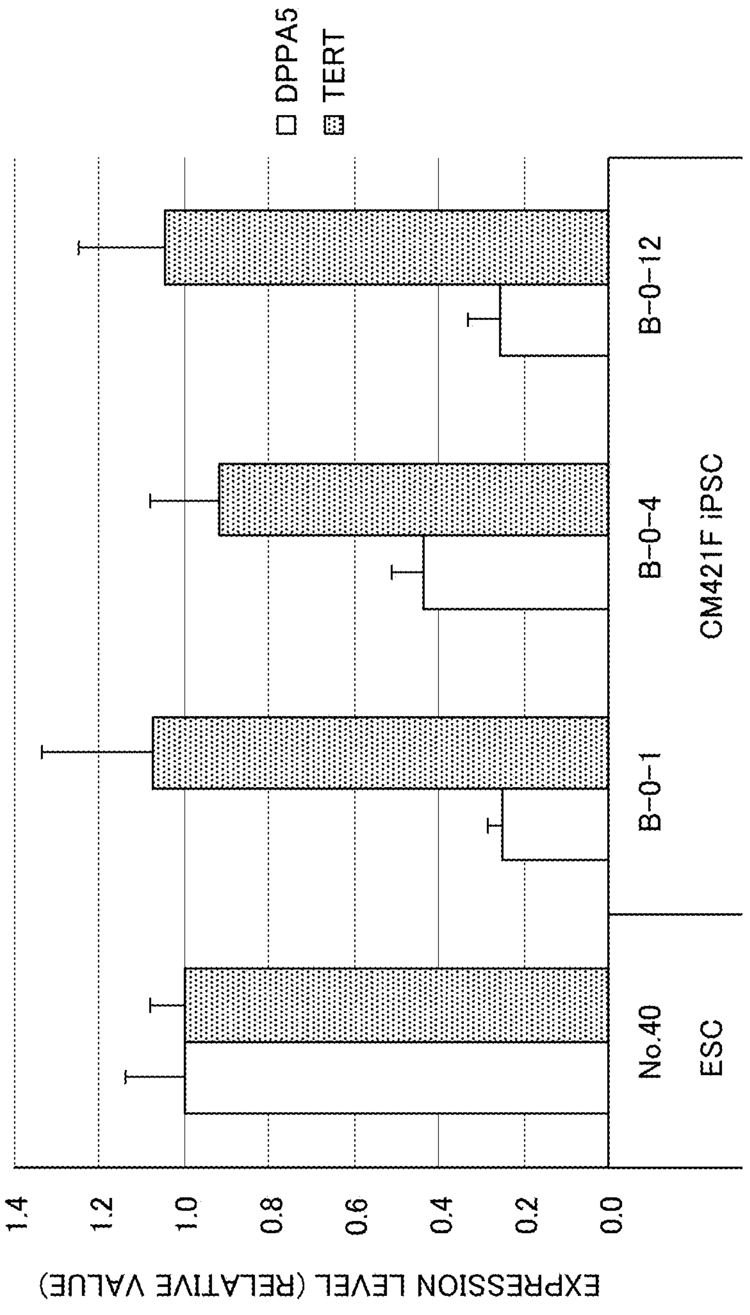
FIG. 29 is a diagram showing the results of analyzing the expression of ES cell markers in marmoset iPS cells derived from fibroblasts of an adult marmoset in Experimental Example 5.

Subsequently, the obtained marmoset iPS cells were immunostained using an anti-TRA-1-60 antibody and an anti-SSEA4 antibody. At the same time, staining was performed using Hoechst. FIG. 25 shows the results.

FIG. 25 shows diagrams showing the results of analyzing the expression of ES cell markers in marmoset iPS cells derived from fibroblasts of an adult marmoset. As a result, it became clear that the obtained marmoset iPS cells express TRA-1-60 and SSEA4 as in the case of ES cells.

Subsequently, for the obtained marmoset iPS cells, the expression of endogenous OCT4, NANOG, SOX2, KLF4, and Lin28 genes, and the expression of the ZFP42 gene, DPPA gene, and TERT gene were analyzed by qRT-PCR. FIGS. 26 to 29 show the results.

FIGS. 26 to 29 are diagrams showing the results of analyzing the expression of ES cell markers in marmoset iPS cells derived from fibroblasts of an adult marmoset. As a result, it became clear that the obtained marmoset iPS cells express the above-mentioned genes as in the case of the marmoset ES cells.

Subsequently, the obtained marmoset iPS cells were differentiated into endoderm, mesoderm, and ectoderm by the same method as in Experimental Example 4, and the expression of a marker gene in each of the germ layers was analyzed.

Figure 30:
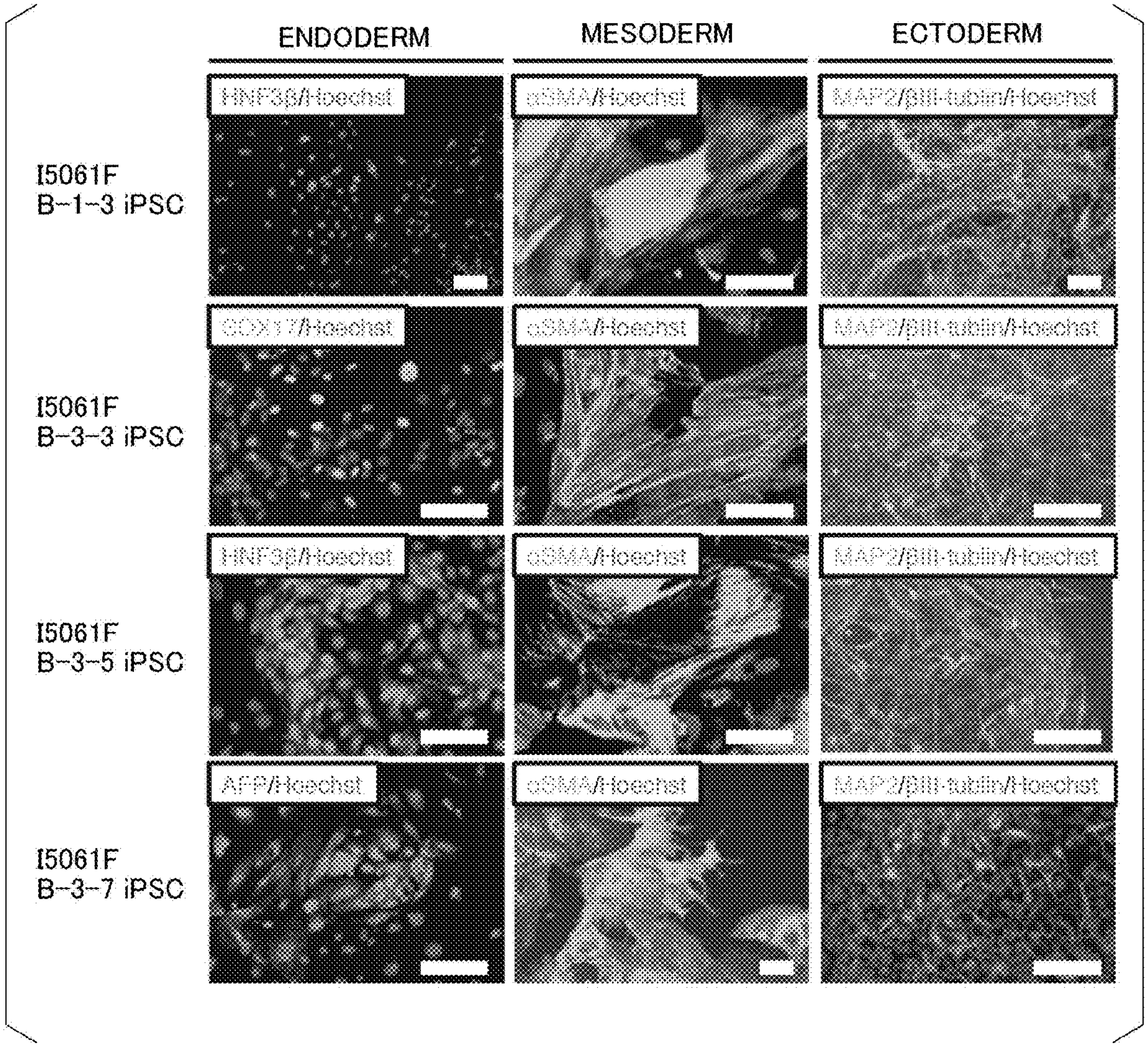
FIG. 30 shows diagrams showing the results of analyzing the expression of markers in three germ layers differentiated from marmoset iPS cells derived from fibroblasts of an adult marmoset in Experimental Example 5.
Figure 31:
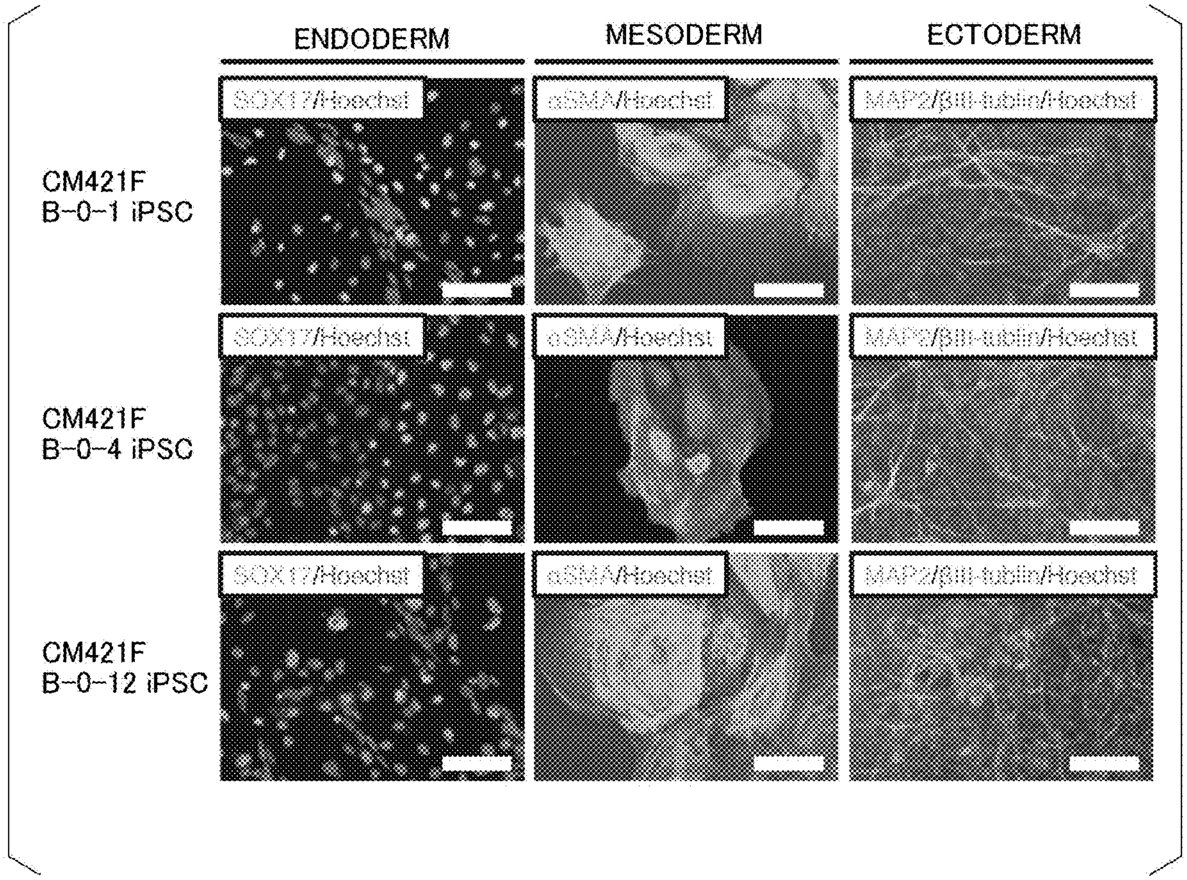
FIG. 31 shows diagrams showing the results of analyzing the expression of markers in three germ layers differentiated from marmoset iPS cells derived from fibroblasts of an adult marmoset in Experimental Example 5.

Subsequently, the expression of AFP for endoderm, αSMA for mesoderm, and MAP2 and βIII-tubulin for ectoderm was analyzed using antibodies against each of the proteins. Furthermore, at the same time, Hoechst staining was also performed. FIGS. 30 and 31 show the results.

FIG. 30 and FIG. 31 show diagrams showing the results of analyzing the expression of markers in three germ layers differentiated from marmoset iPS cells derived from fibroblasts of an adult marmoset. As a result, it became clear that each of the germ layers formed by being differentiated from the obtained marmoset iPS cells expresses a marker gene characteristic of each of the germ layers.

Figure 32:
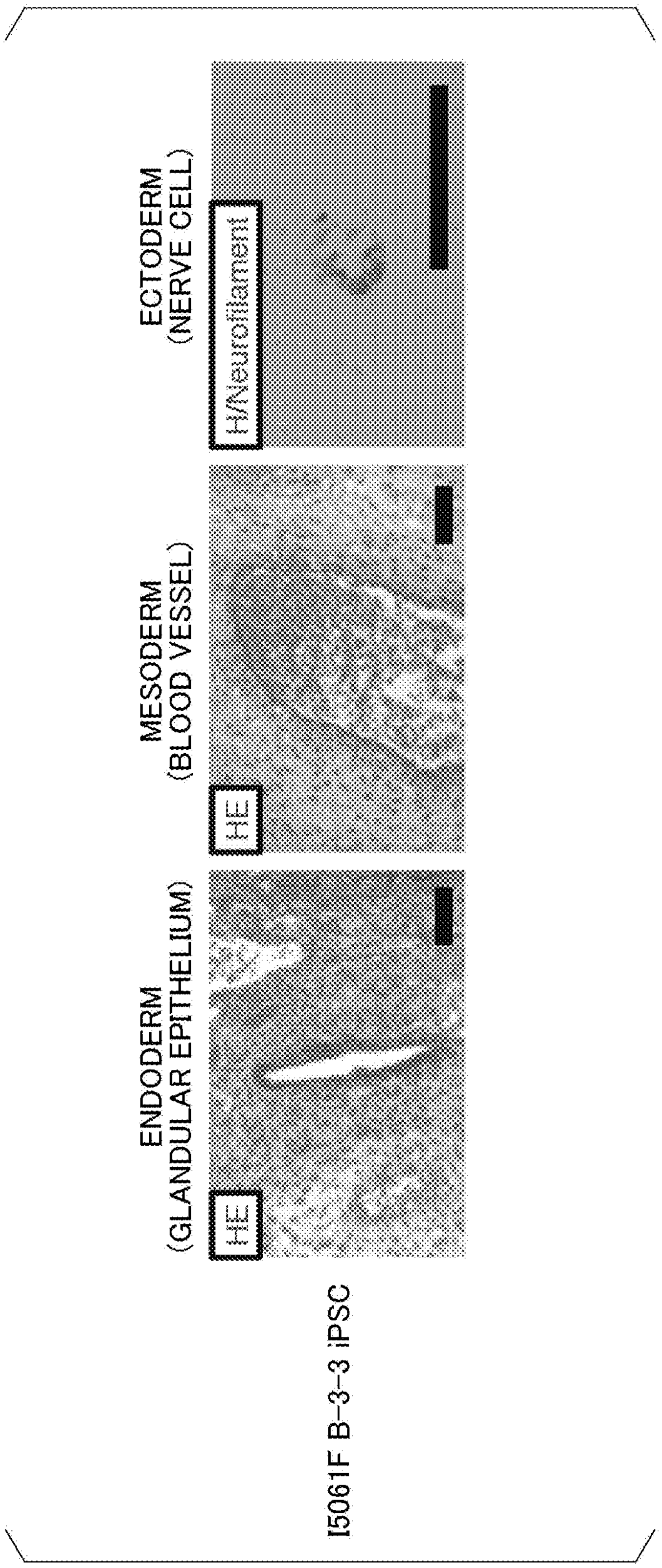
FIG. 32 shows diagrams showing the results of analyzing teratomas formed from marmoset iPS cells derived from fibroblasts of an adult marmoset in Experimental Example 5.

Furthermore, teratomas were produced from the obtained marmoset iPS cells in the same manner as in Experimental Example 4, and tissues differentiated from endoderm, mesoderm, and ectoderm were observed. Glandular epithelium differentiated from the endoderm and blood vessels differentiated from the mesoderm were observed by HE staining, and nerve cells differentiated from the ectoderm were observed by HE staining and immunostaining with an antibody against neurofilament 200 kDa. FIG. 32 shows the results.

FIG. 32 shows diagrams showing the results of analyzing teratomas formed from marmoset iPS cells derived from fibroblasts of an adult marmoset. As a result, it became clear that the differentiated glandular epithelium, blood vessels, and nerve cells are formed in the teratomas.

Figure 33:
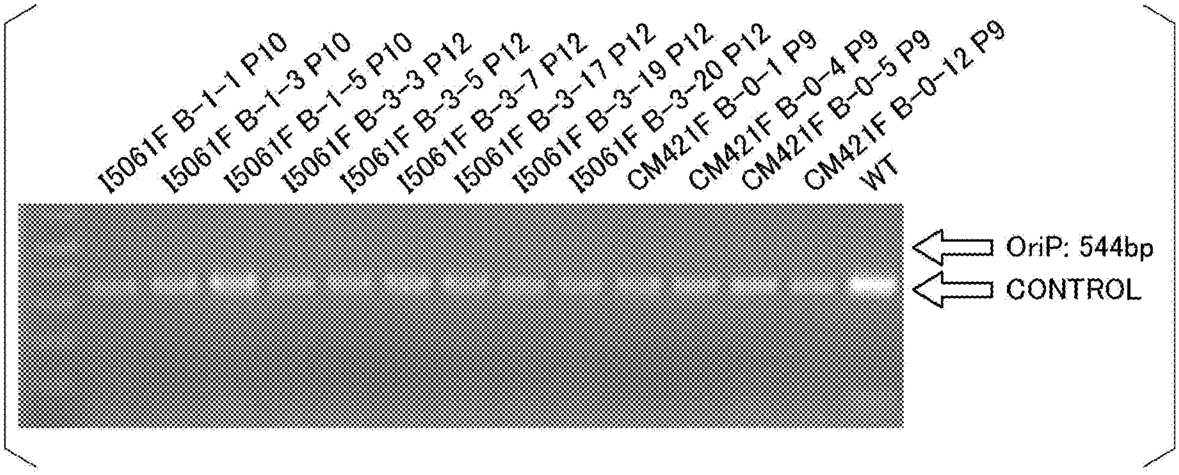
FIG. 33 is a diagram showing the results of analyzing whether or not a vector remains in marmoset iPS cells derived from fibroblasts of an adult marmoset in Experimental Example 5.

In addition, regarding the obtained marmoset iPS cells, whether or not the vector contained in the EP-A vector set or the EP-B vector set remained was analyzed by a PCR method. FIG. 33 shows the results.

FIG. 33 is a diagram showing the results of analyzing whether or not a vector remains in marmoset iPS cells derived from fibroblasts of an adult marmoset. As a result, it became clear that the vector did not remain in the obtained marmoset iPS cells.

Experimental Example 6

Analysis of Gene Expression Pattern in iNSL Cells

The EP-A vector set or the EP-B vector set was introduced into marmoset embryonic fibroblasts or adult marmoset fibroblasts. Thereafter, culturing was performed in a neural stem cell culture medium to obtain induced neural stem cell-like cells (iNSL cells). The gene expression pattern and the differentiation potential into nerve cells of the obtained iNSL cells were analyzed.

Figure 34:
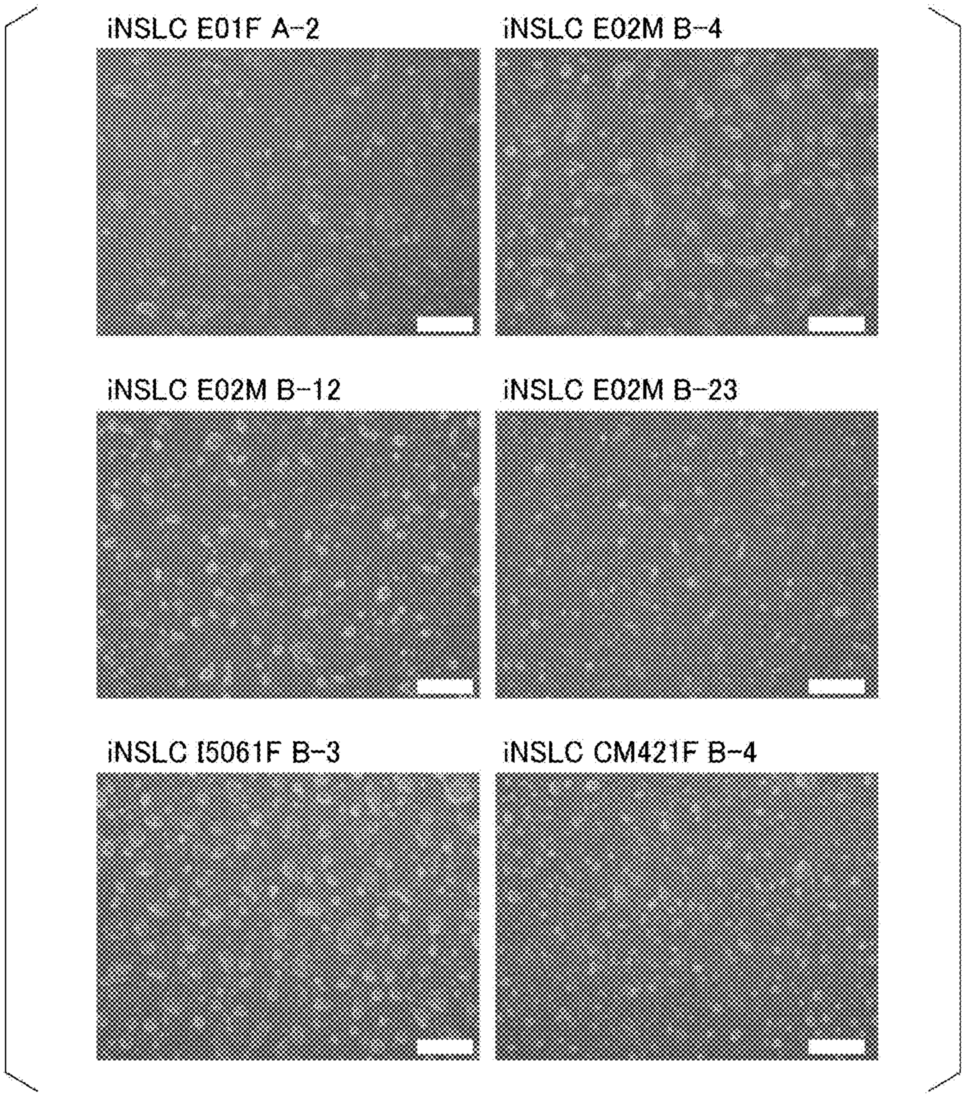
FIG. 34 shows photographs of marmoset iNSL cells in Experimental Example 6.

First, the EP-A vector set or EP-A vector set was introduced into marmoset embryonic fibroblasts, and thereafter, culturing was performed in a neural stem cell culture medium. FIG. 34 shows the results. FIG. 34 shows photographs of marmoset iNSL cells. As a result, it was confirmed that iNSL cells were obtained.

Figure 35:
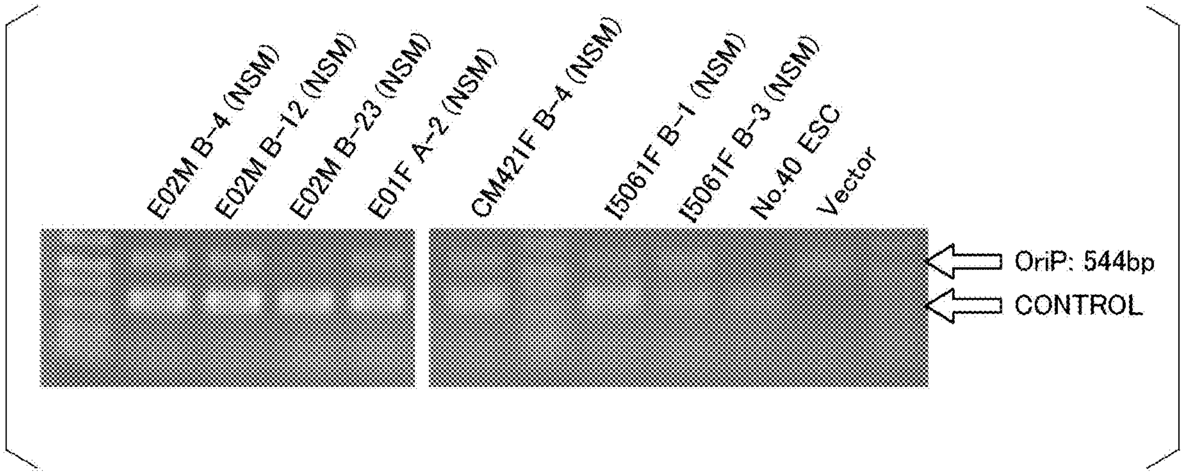
FIG. 35 shows diagrams showing the results of analyzing a vector remaining in marmoset iNSL cells in Experimental Example 6.

Subsequently, whether or not the EP-A vector set or the EP-B vector set remained in the obtained iNSL cells was analyzed by a PCR method. FIG. 35 shows the results. FIG. 35 shows diagrams showing the results of analyzing a vector remaining in iNSL cells.

As a result, it became clear that the EP-A vector set or the EP-B vector set remained in the iNSL cells passaged 10 times after the introduction of the vector set.

Figure 36:
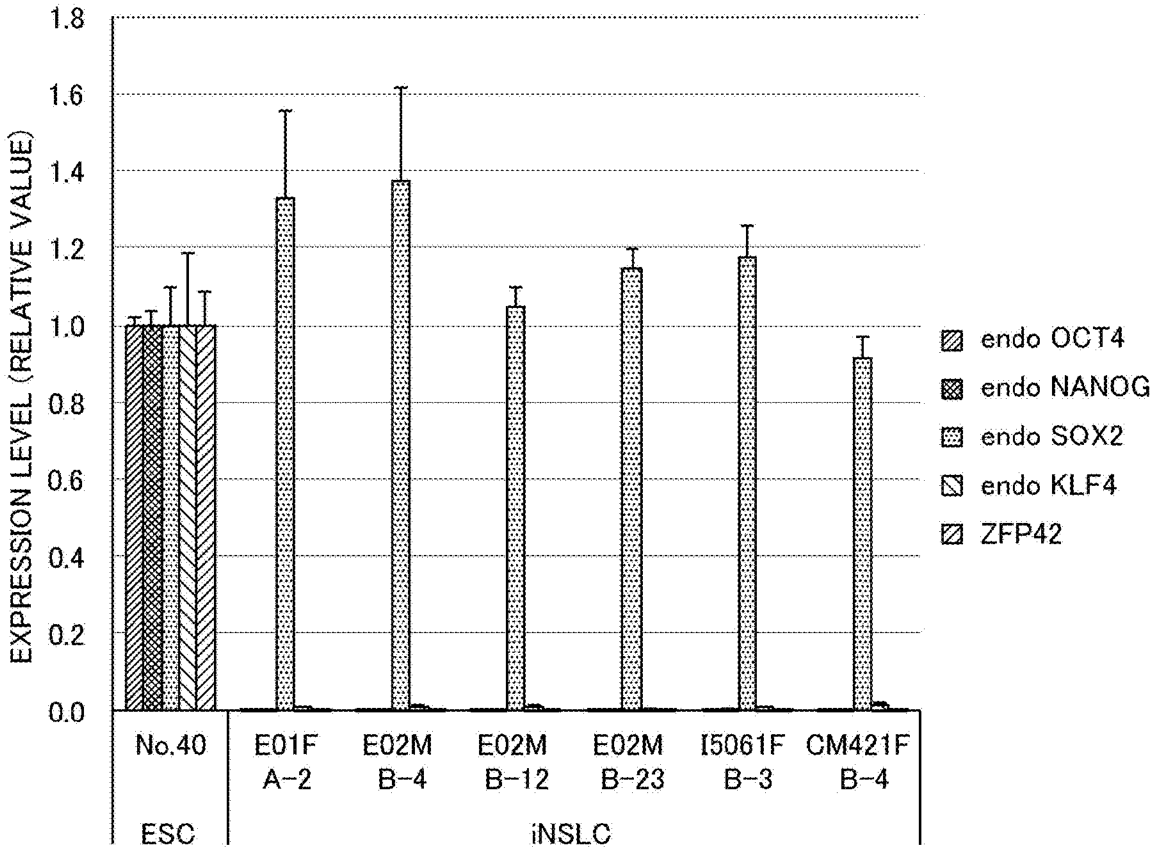
FIG. 36 is a diagram showing the results of analyzing the expression of endogenous OCT4, NANOG, SOX2, KLKF4, and ZFP42 in marmoset iNSL cells in Experimental Example 6.
Figure 37:
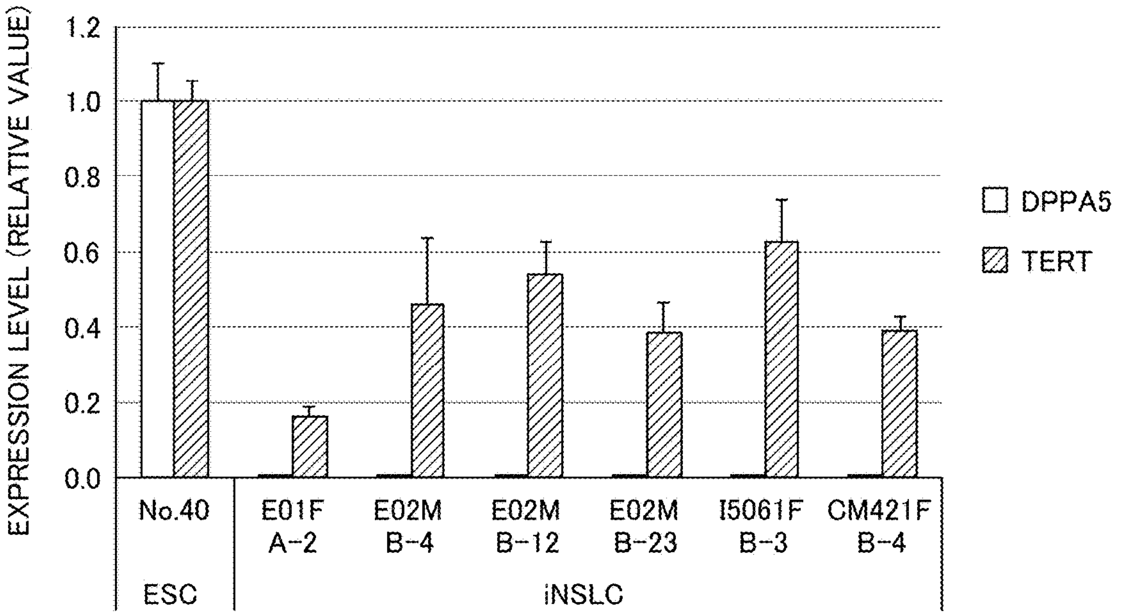
FIG. 37 is a diagram showing the results of analyzing the expression of DPPA5 and TERT in marmoset iNSL cells in Experimental Example 6.

Subsequently, the gene expression pattern of the obtained iNSL cells was analyzed by qRT-PCR. FIG. 36 and FIG. 37 show the results. FIG. 36 is a diagram showing the results of analyzing the expression of endogenous OCT4, NANOG, SOX2, KLKF4, and ZFP42 in iNSL cells. FIG. 37 is a diagram showing the results of analyzing the expression of DPPA5 and TERT in iNSL cells.

As a result, it became clear that the obtained iNSL cells endogenously express SOX2 and TERT, but do not endogenously express OCT4, NANOG, KLF4, ZFP42, and DPPA5.

Figure 38:
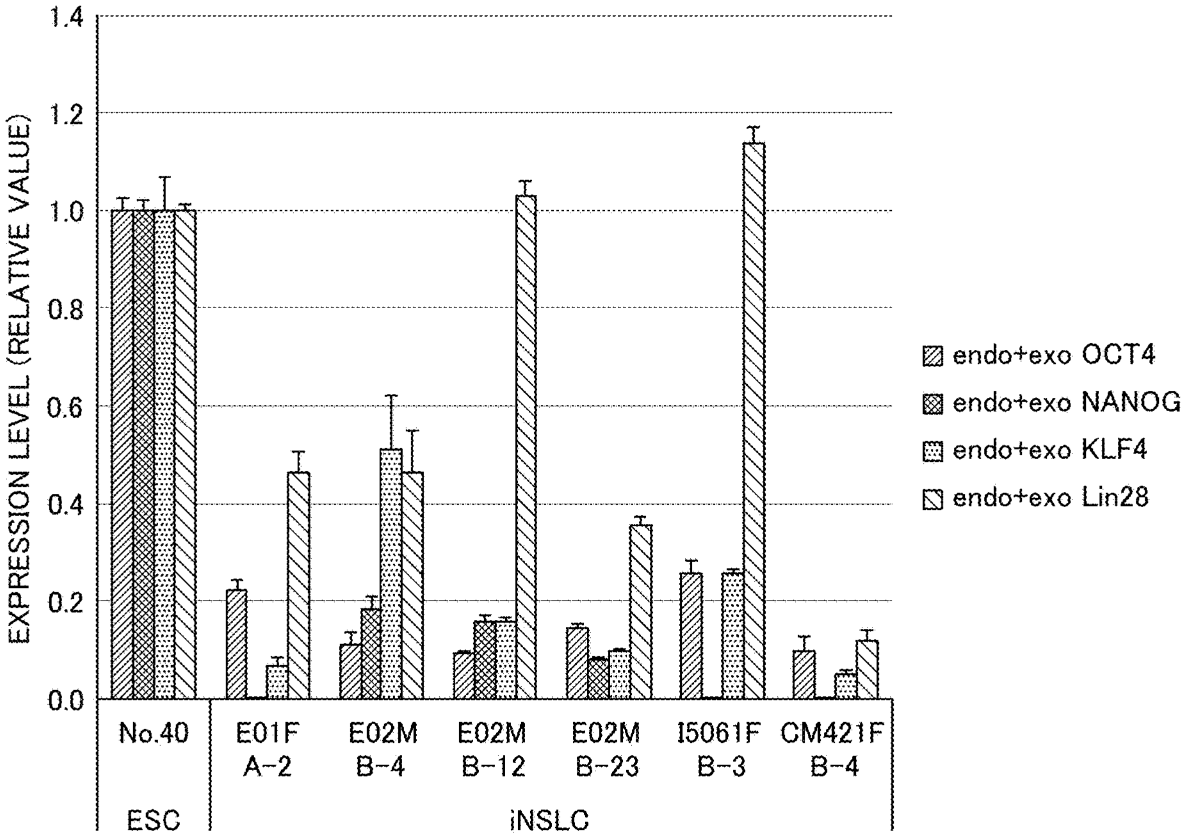
FIG. 38 is a diagram showing the results of analyzing the expression of endogenous and exogenous OCT4, NANOG, KLF4, and Lin28 in marmoset iNSL cells in Experimental Example 6.

Subsequently, the gene expression level of the obtained iNSL cells, in which the endogenous gene expression and the exogenous (gene expression by the vector set) gene expression were combined, was analyzed by qRT-PCR. FIG. 38 is a diagram showing the results of analyzing the expression of endogenous and exogenous OCT4, NANOG, KLF4, and Lin28 in iNSL cells.

As a result, it became clear that in the gene expression level in which the endogenous gene expression and the exogenous gene expression were combined, OCT4, KLF4, and Lin28 were expressed, but NANOG was not expressed.

Figure 39:
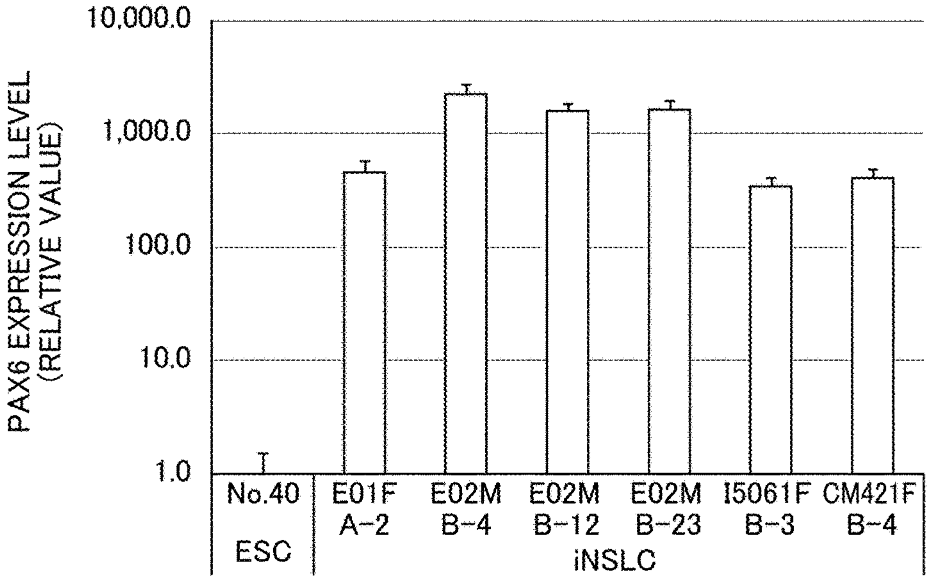
FIG. 39 is a diagram showing the results of analyzing the expression of PAX6 in marmoset iNSL cells in Experimental Example 6.
Figure 40:
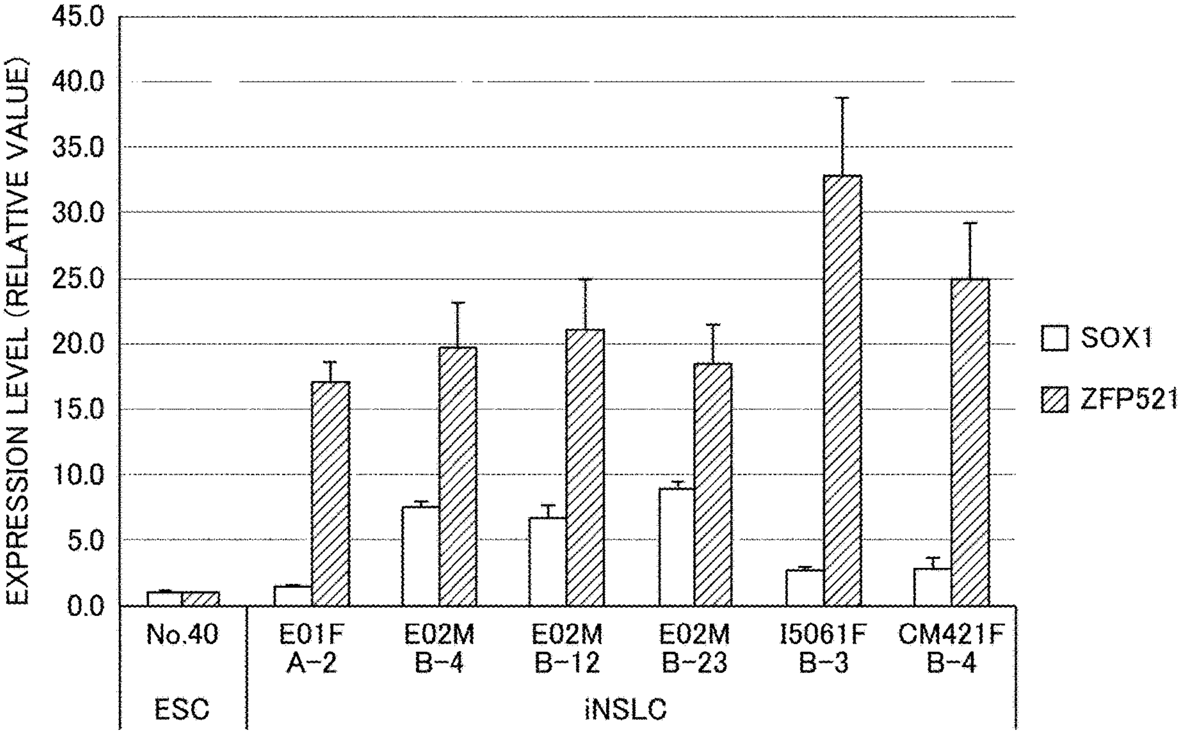
FIG. 40 is a diagram showing the results of analyzing the expression of SOX1 and ZFP521 in marmoset iNSL cells in Experimental Example 6.

Subsequently, for the obtained iNSL cells, the expression of PAX6 (Paired box 6), SOX1 (Sry-type HMG box 1), and ZFP521 (Zinc Finger Protein 521), which are neural stem cell markers, was analyzed by qRT-PCR. FIG. 39 and FIG. 40 show the results.

FIG. 39 is a diagram showing the results of analyzing the expression of PAX6 in iNSL cells. FIG. 40 is a diagram showing the results of analyzing the expression of SOX1 and ZFP521 in iNSL cells. As a result, it became clear that PAX6 is not expressed in marmoset ES cells, but the obtained induced neural stem cells express PAX6, SOX1, and ZFP521.

Figure 41:
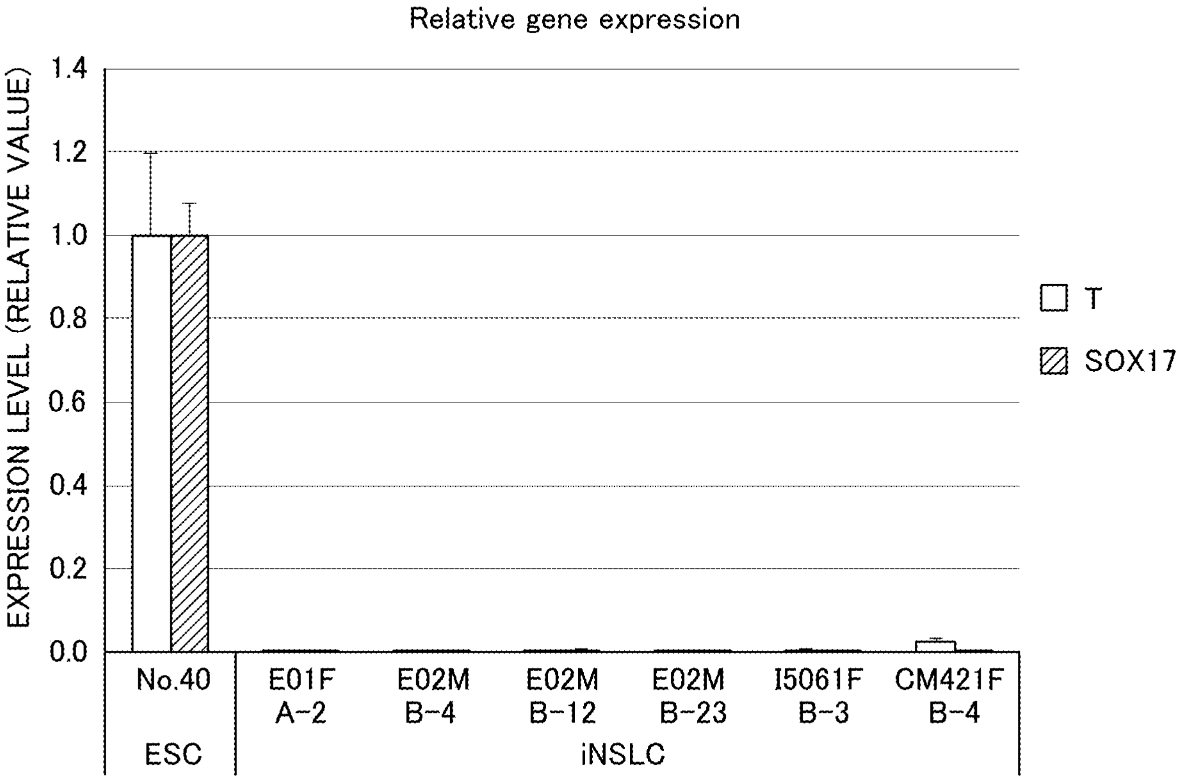
FIG. 41 is a diagram showing the results of analyzing the expression of T and SOX17 in marmoset iNSL cells in Experimental Example 6.

Subsequently, for the obtained induced neural stem cells, the expression of T (TBX T), which is a mesoderm marker, and SOX17 (Sry-type HMG box 17), which is an endoderm marker, was analyzed by qRT-PCR. FIG. 41 shows the results.

FIG. 41 is a diagram showing the results of analyzing the expression of T and SOX17 in iNSL cells. As a result, it was confirmed that T and SOX17 are expressed in marmoset ES cells but not in the obtained induced neural stem cells.

Figure 42:
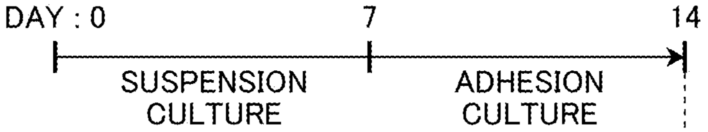
FIG. 42 is a schedule of neural differentiation assays in Experimental Example 6.
Figure 43:
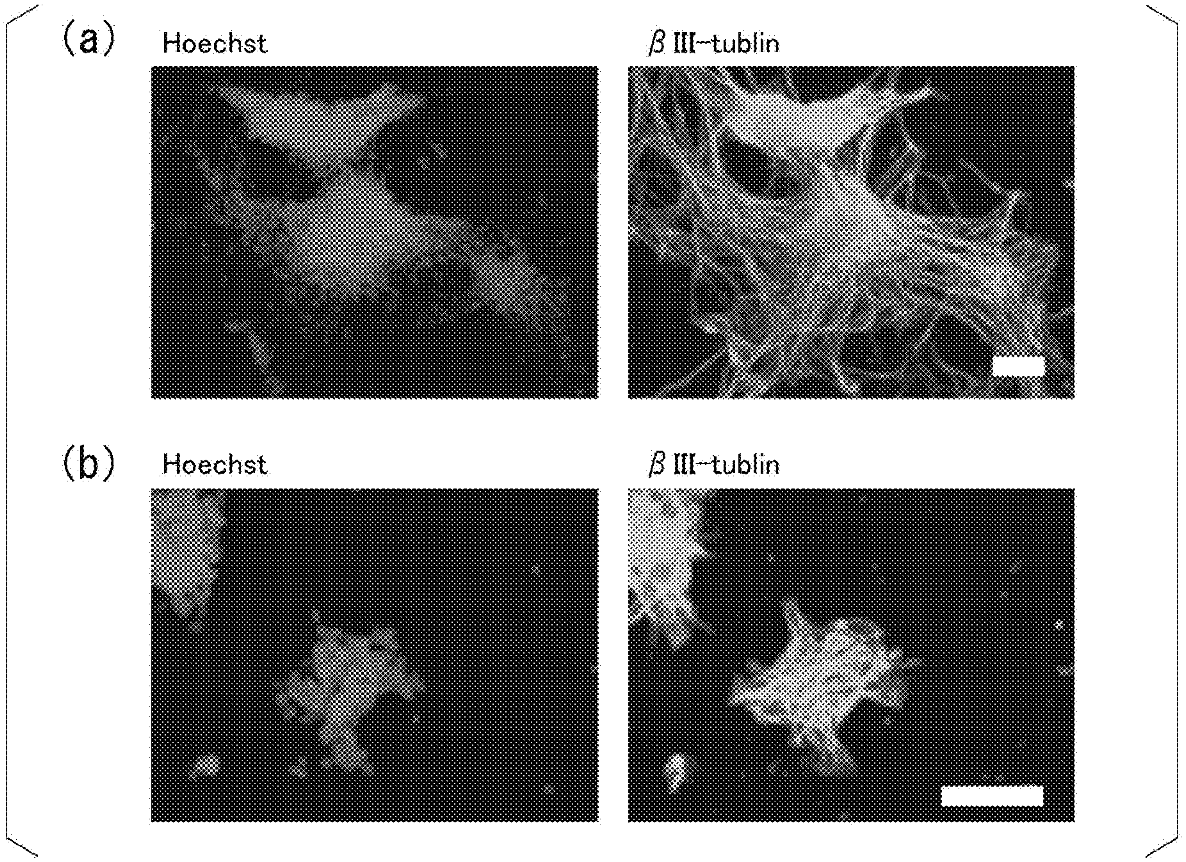
FIG. 43 shows diagrams showing the results of immunostaining of cells differentiated from the obtained induced neural stem cells with a Hoechst stain and an anti-βIII-tubulin antibody in Experimental Example 6.
Figure 44:
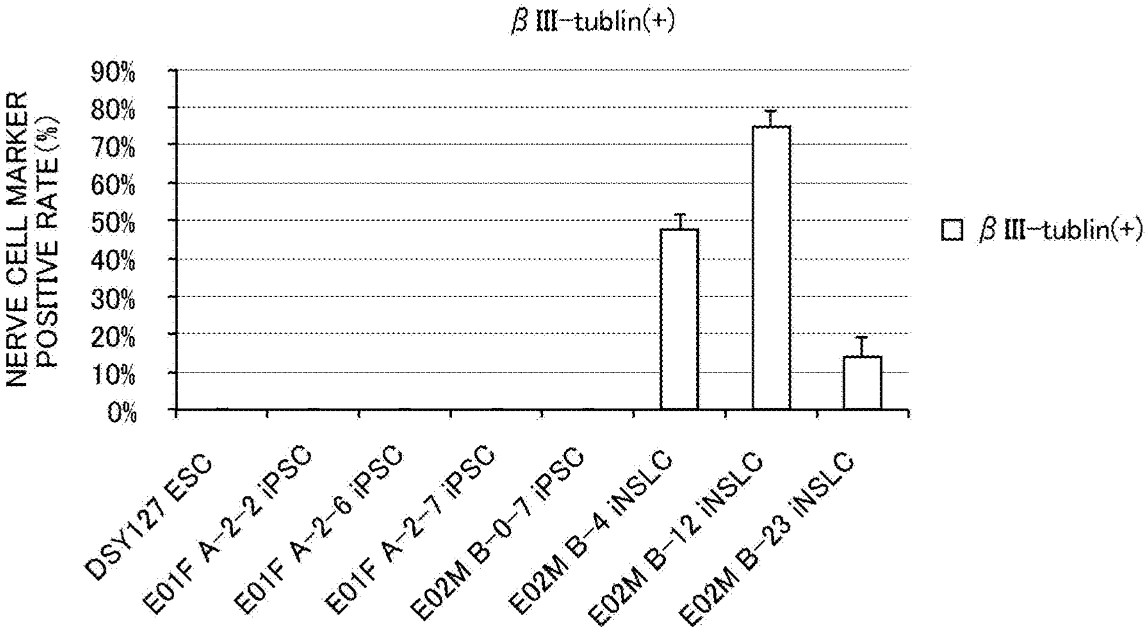
FIG. 44 is a graph showing the proportion of cells in which the expression of βIII-tubulin was recognized among cells differentiated into nerve cells in Experimental Example 6.

Subsequently, the marmoset ES cells, marmoset iPS cells, and marmoset-induced neural stem cells were analyzed for the differentiation potential into neural stem cells by unbiased neuronal differentiation assay. FIG. 42 is a schedule of neural differentiation assays. Specifically, suspension culture was performed for 7 days, and thereafter adhesion culture was performed for 7 days. FIG. 43 and FIG. 44 show the results.

FIG. 43 shows diagrams showing the results of immunostaining of cells differentiated from the obtained induced neural stem cells with a Hoechst stain and an anti-βIII-tubulin antibody. As a result, it became clear that the cells differentiated from the obtained induced neural stem cells differentiated into nerve cells.

FIG. 44 is a graph showing the proportion of cells in which the expression of βIII-tubulin was recognized among cells differentiated into nerve cells. As a result, it became clear that cells differentiated from marmoset ES cells and marmoset iPS cells do not express βIII-tubulin, but cells differentiated from marmoset-induced neural stem cells express βIII-tubulin.

From the above results, it became clear that the iNSL cells, which were obtained by introducing the EP-A vector set or EP-B vector set into adult marmoset fibroblasts and performing culturing in a neural stem cell culture medium, acquire the traits of neural stem cells.

In addition, it became clear that, when iNSL cells are continuously cultured in the neural stem cell culture medium without being transferred to the growth medium, the iNSL cells retain the traits of neural stem cells and do not acquire the traits of ES cells even though the iNSL cells continue to retain the vector.

From this result, it became clear that it is not possible to directly produce iPS cells from adult somatic cells of a pluripotency induction-resistant animal, but it is possible to cause dedifferentiation into neural stem cells once and thereafter further dedifferentiation into iPS cells.

Experimental Example 7

Gene Profiling of Marmoset iPS Cells and iNSL Cells

Clustering analysis was performed on the gene expression profiles of ES cells, iPS cells, and iNSL cells of marmosets.

Figure 45:
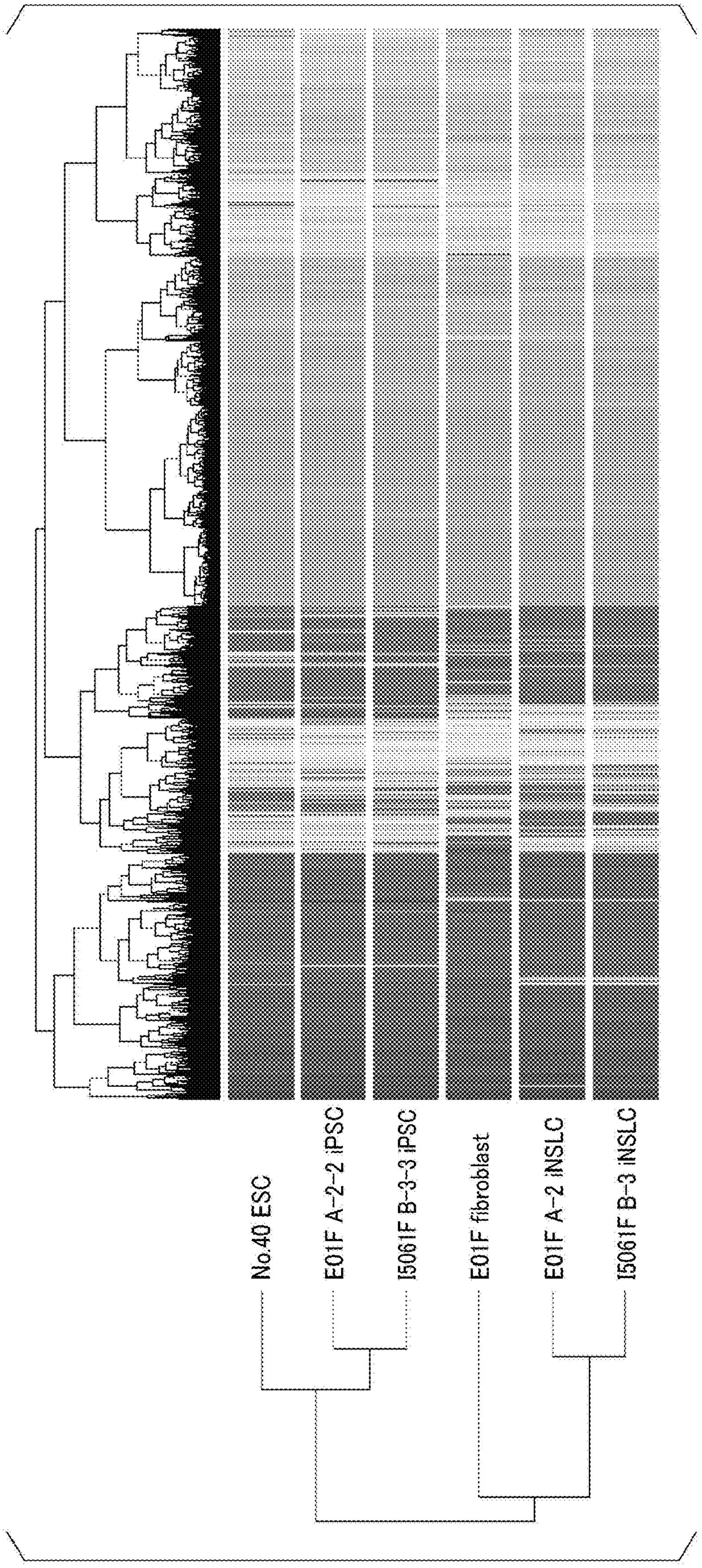
FIG. 45 is a diagram showing the results of clustering analysis in Experimental Example 7.

Clustering analysis was performed on the ES cells, iPS cells, and iNSL cells of marmosets based on a comprehensive gene expression profile. FIG. 45 shows the results. As a result, it became clear that the marmoset iPS cells have high similarity to the marmoset ES cells, and the marmoset iNSL cells have high similarity to the marmoset fibroblasts.

Figure 46:
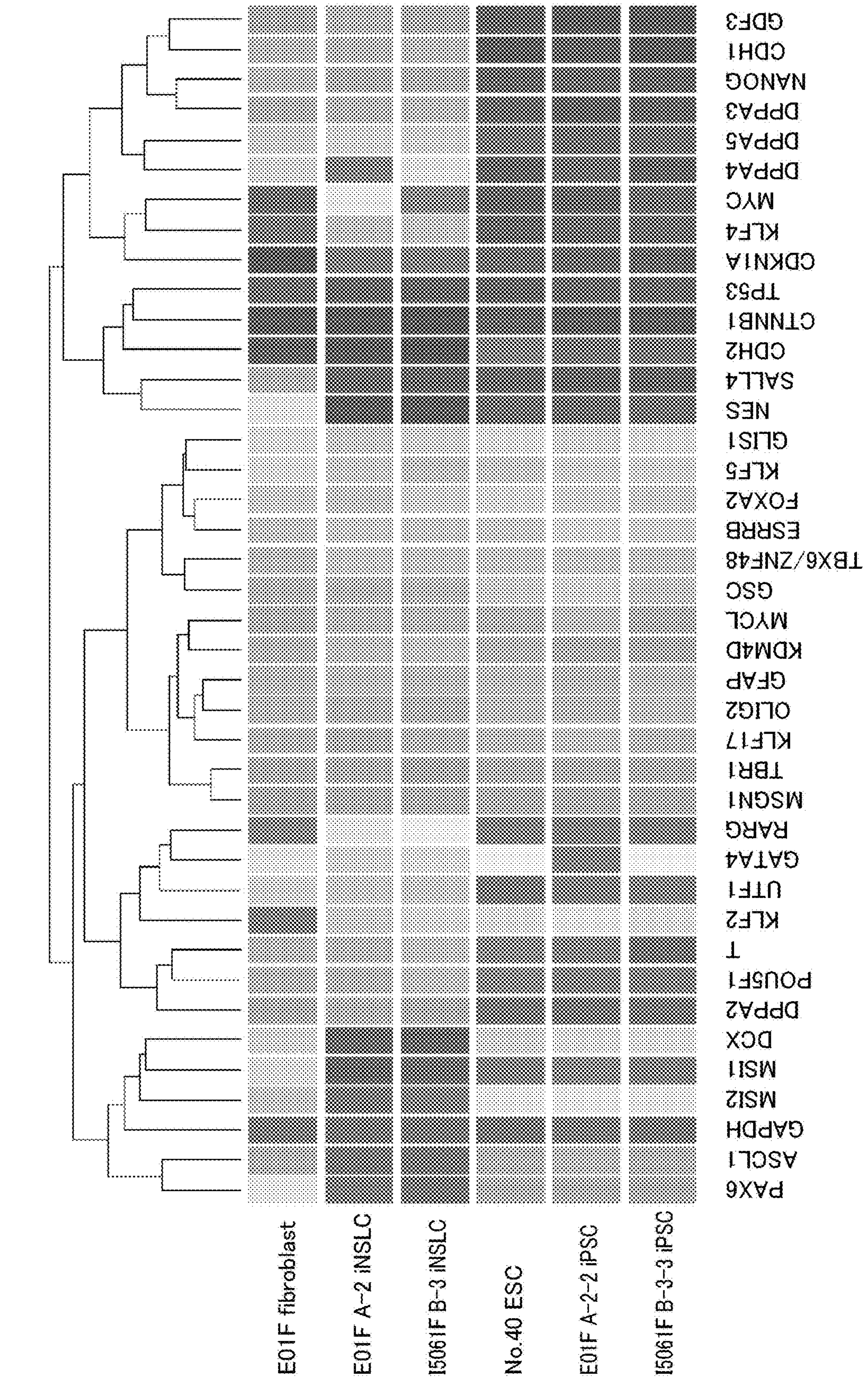
FIG. 46 is a diagram showing the results of analyzing the gene expression level in Experimental Example 7.

Subsequently, the expression levels of 40 genes, reflecting the similarity of each cluster, in each of the cells were analyzed. FIG. 46 shows the results. As a result, genes having characteristic expression levels could be extracted from the marmoset iPS cells and the marmoset-induced neural stem cells.

Figure 47:
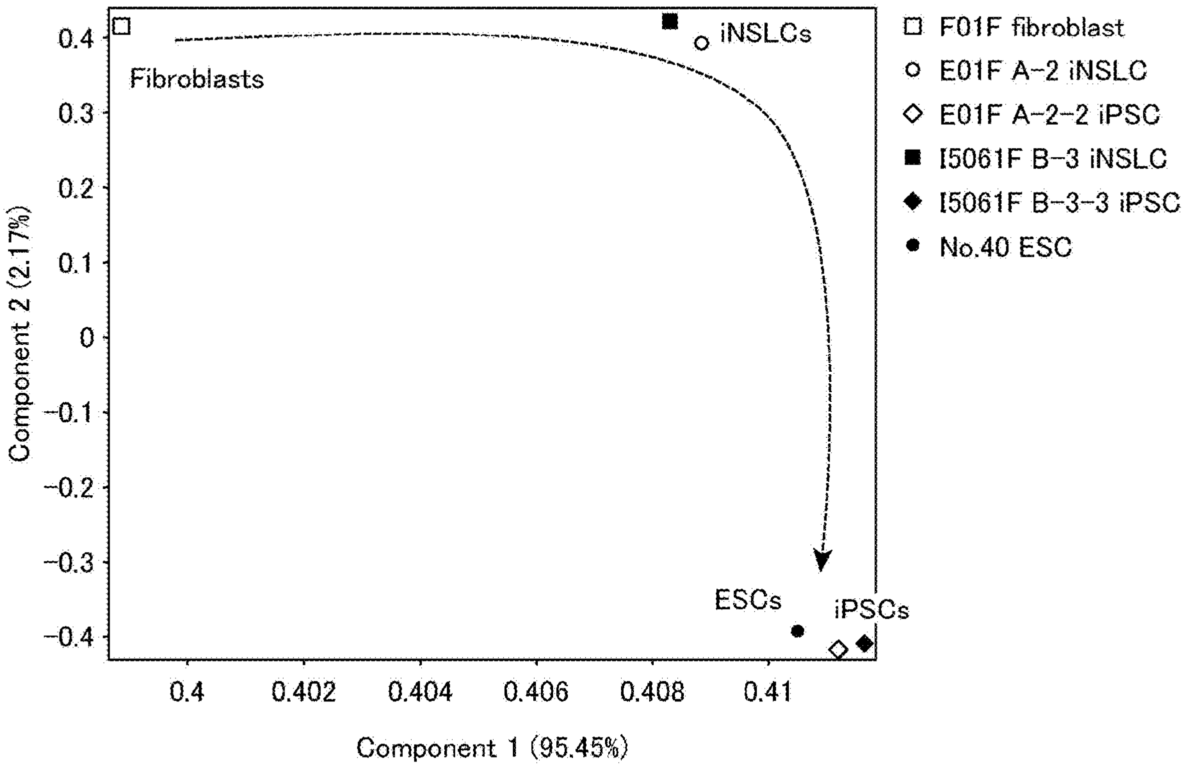
FIG. 47 is a diagram showing the results of principal component analysis in Experimental Example 7.

Principal component analysis was performed on the gene expression profile of each of the cells. FIG. 47 shows the results. As a result, it became clear that each of the cells was divided into a group of fibroblasts, ES cells and iPS cells, and induced neural stem cells.

Experimental Example 8

Establishment of Canine iPS Cells

The EP-B vector set was introduced into canine fibroblasts to establish canine iPS cells.

Figure 48:
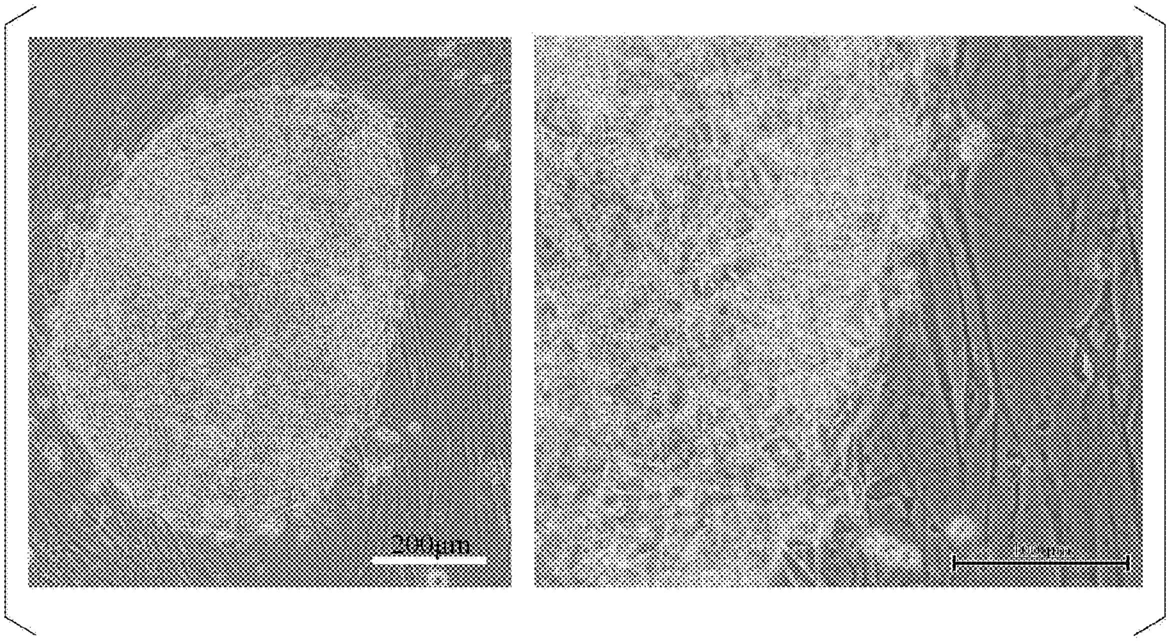
FIG. 48 shows photographs of colonies formed by canine iPS cells in Experimental Example 8.

FIG. 48 shows the results. FIG. 48 shows photographs of colonies formed by canine iPS cells. As a result, it became clear that the canine iPS cells form colonies similar to the colonies formed by ES cells.

Figure 49:
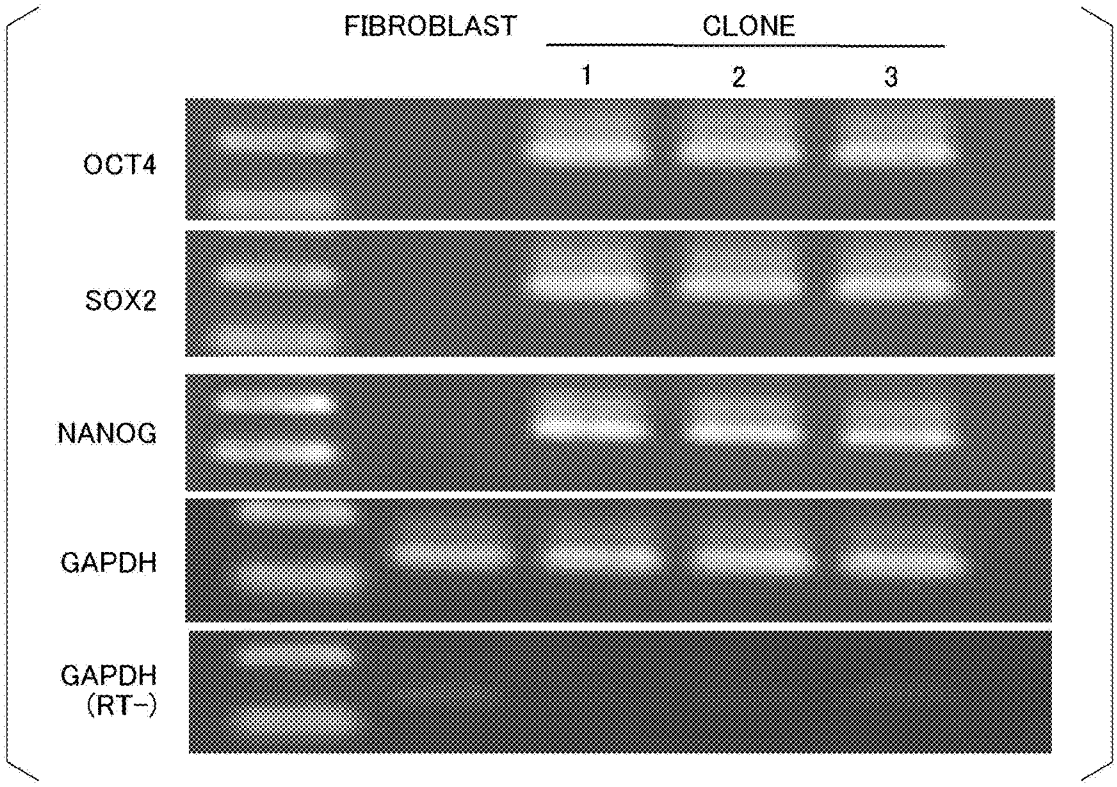
FIG. 49 shows diagrams showing the results of analyzing the expression of OCT4, SOX2, and NANOG in canine iPS cells in Experimental Example 8.

The expression of markers of ES cells was analyzed for the obtained canine iPS cells. FIG. 49 shows the results. FIG. 49 shows diagrams showing the results of analyzing the expression of OCT4, SOX2, and NANOG in canine iPS cells by RT-PCR.

As a result, it became clear that the canine iPS cells express OCT4, SOX2, and NANOG. That is, it was suggested that the canine iPS cells have the traits similar to those of ES cells.

Figure 50:
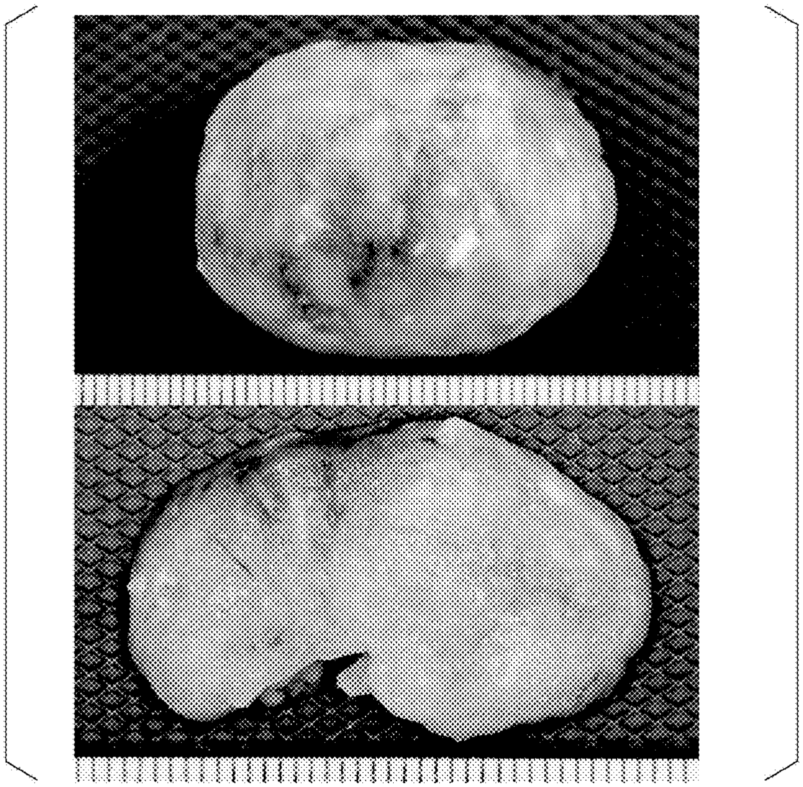
FIG. 50 shows photographs of teratomas formed from canine iPS cells in Experimental Example 8.

The canine iPS cells were injected into the testicle of an immunodeficient mouse (NOD/SCID), and after 2 to 3 months, teratomas formed inside the testicle were excised to observe the teratomas. FIG. 50 shows the results.

Figure 51:
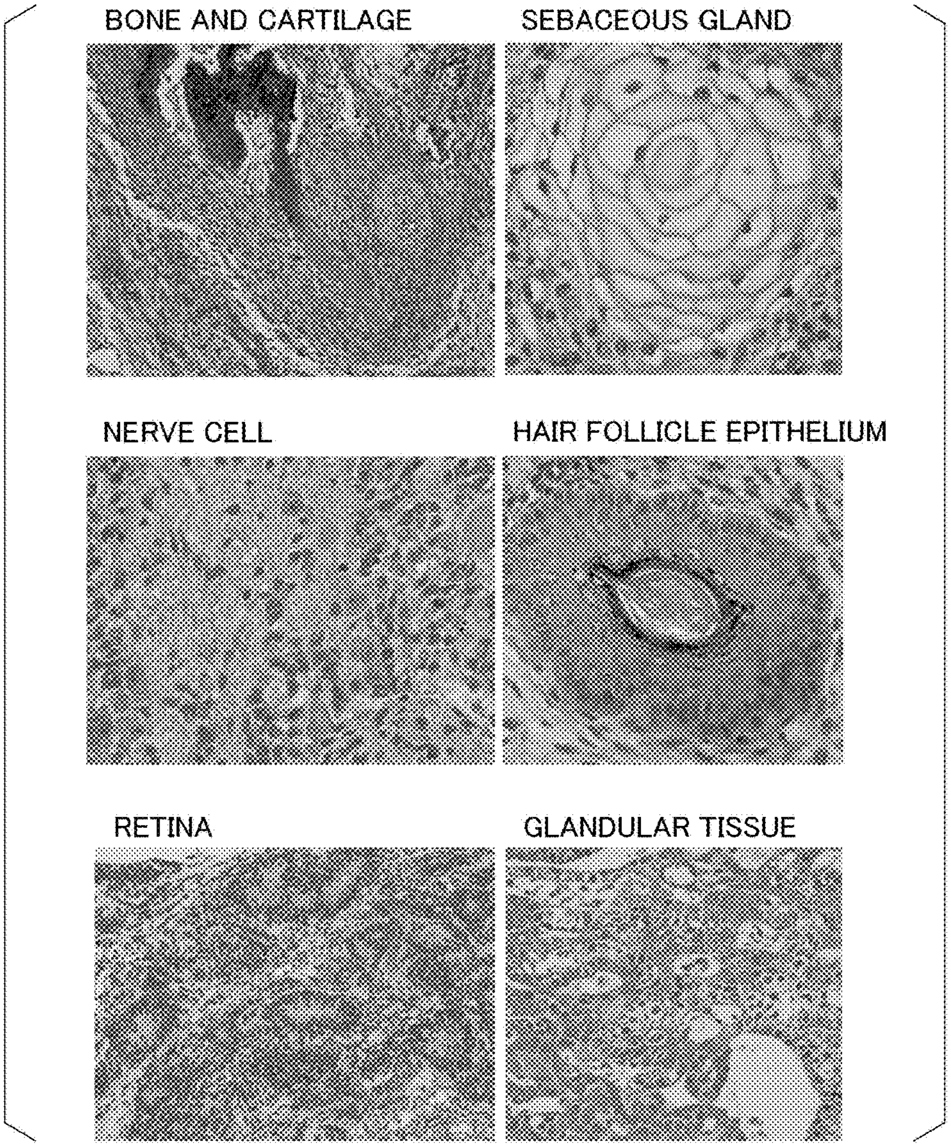
FIG. 51 shows diagrams showing the results of analyzing the bone, cartilage, nerve cells, retina, sebaceous gland, hair follicle epithelium, and glandular tissue in teratomas formed from canine iPS cells in Experimental Example 8.

The obtained teratomas were subjected to hematoxylin and eosin staining to observe each tissue. FIG. 51 shows the results. FIG. 51 shows diagrams showing the results of analyzing the bone, cartilage, nerve cells, retina, sebaceous gland, hair follicle epithelium, and glandular tissue.

Figure 52:
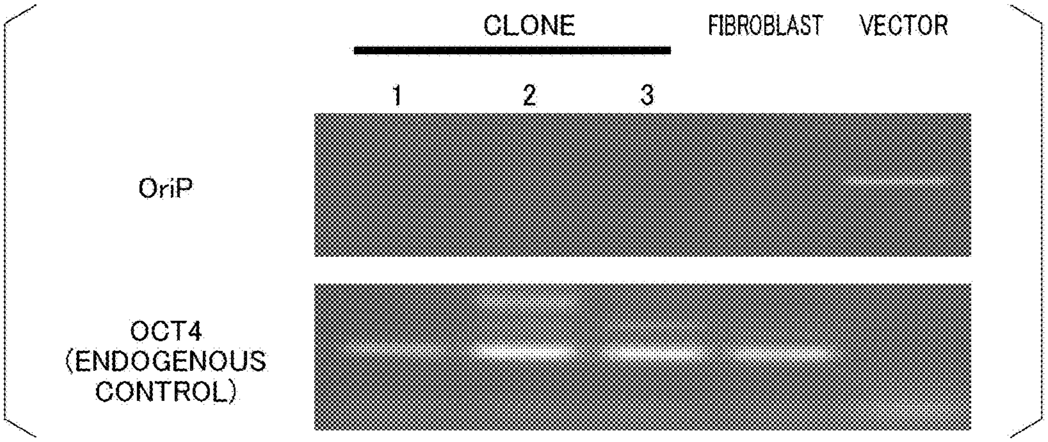
FIG. 52 shows diagrams showing the results of analyzing whether or not a vector remains in canine iPS cells in Experimental Example 8.

Whether or not the vector introduced into the obtained canine iPS cells remained was analyzed by a PCR method. FIG. 52 shows the results. As a result, it was confirmed that the expression vector did not remain in the canine iPS cells.

Experimental Example 9

Establishment of Porcine iPS Cells

The EP-B vector set was introduced into porcine fibroblasts to establish porcine iNSL cells and porcine iPS cells.

Figure 53:
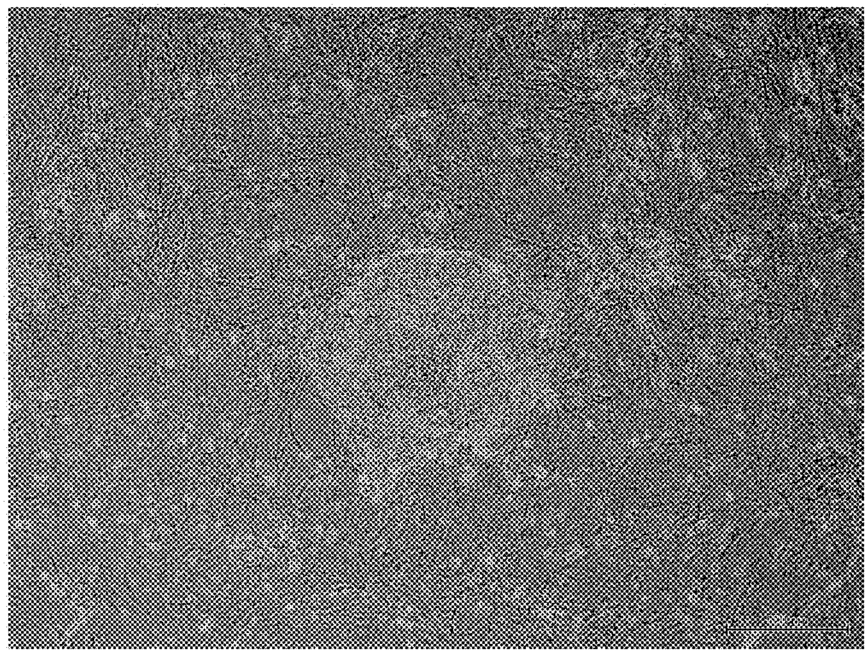
FIG. 53 is a photograph of a colony of porcine iPS cells in Experimental Example 9.

FIG. 53 is a photograph of a colony of porcine iPS cells. It became clear that the porcine iPS cells form colonies similar to the colonies formed by ES cells.

Figure 54:
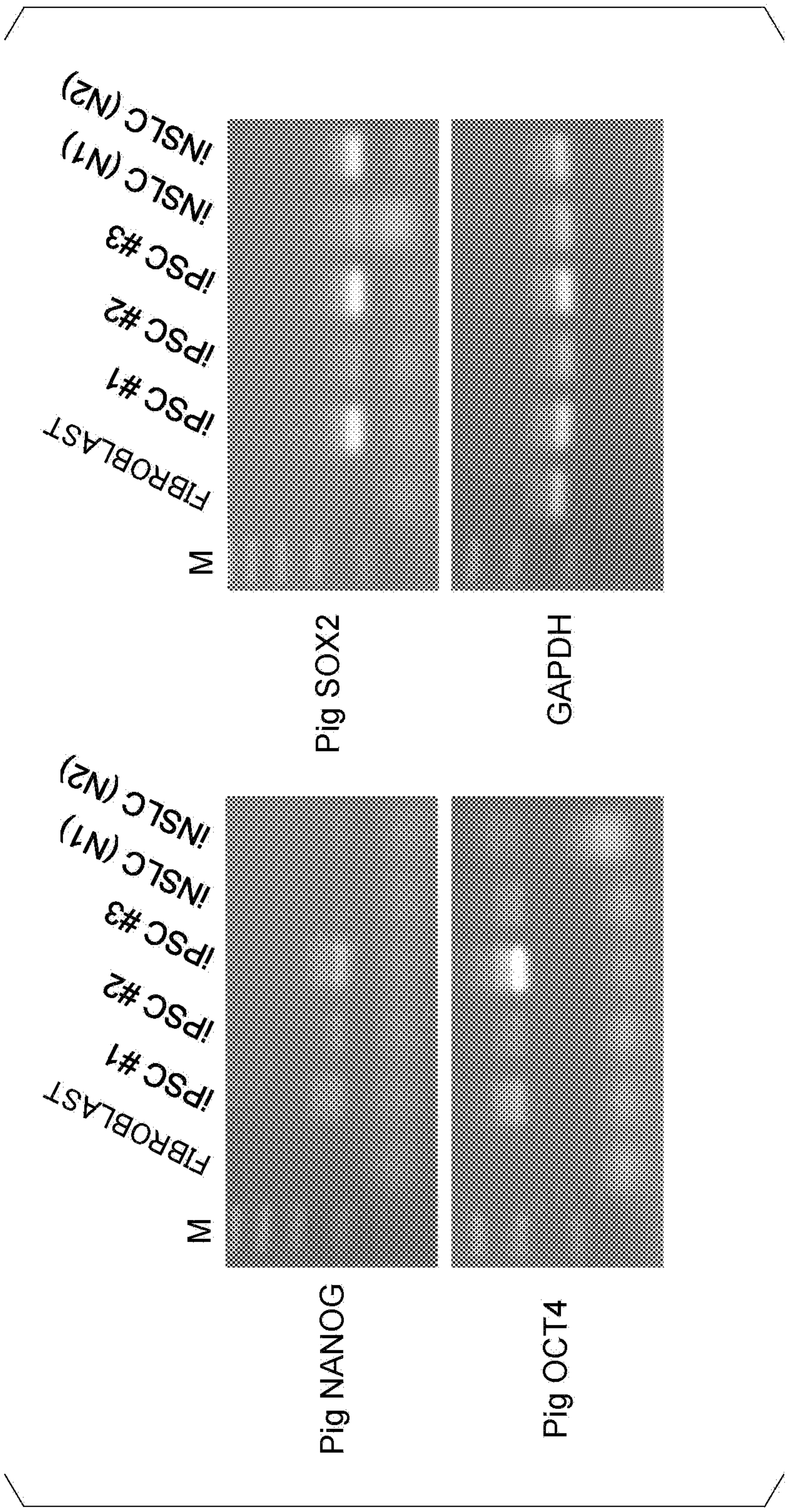
FIG. 54 shows diagrams showing the results of analyzing the expression of OCT4, SOX2, and NANOG in porcine iNSL cells and porcine iPS cells in Experimental Example 9.

Subsequently, the expression of markers of ES cells in the porcine iPS cells and porcine iNSL cells was analyzed by RT-PCR. FIG. 54 shows diagrams showing the results of analyzing the expression of OCT4, SOX2, and NANOG in porcine iNSL cells and porcine iPS cells.

As a result, it became clear that the porcine iPS cells express OCT4, SOX2, and NANOG. Furthermore, it also became clear that the porcine iNSL cells express SOX2.

Experimental Example 10

Establishment of Ferret iPS Cells

The EP-B vector set was introduced into ferret fibroblasts to establish ferret iNSL cells and ferret iPS cells.

Figure 55:
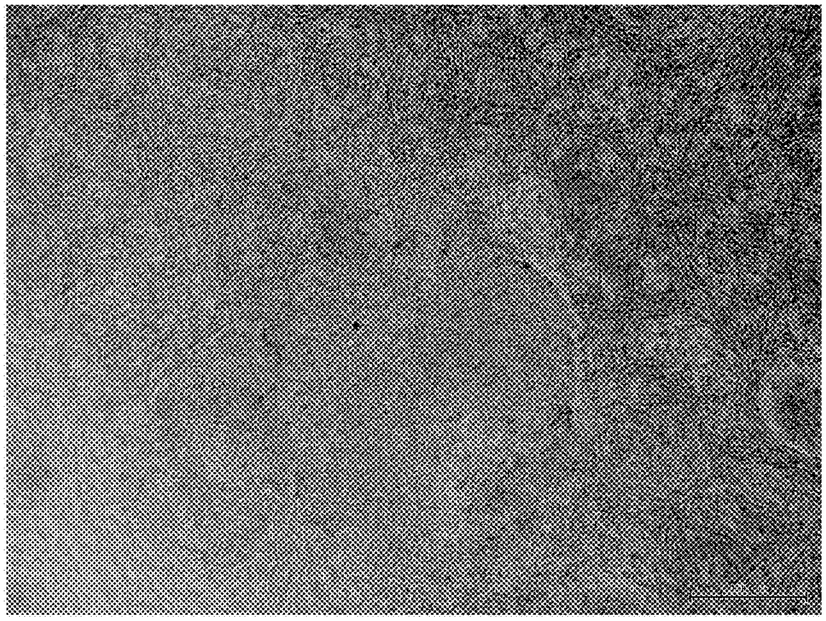
FIG. 55 is a photograph of a colony of ferret iPS cells in Experimental Example 10.

FIG. 55 is a photograph of a colony of the obtained ferret iPS cells. It became clear that the ferret iPS cells form colonies similar to the colonies formed by ES cells.

Subsequently, the expression of markers of ES cells in the ferret iPS cells was analyzed. FIG. 56 shows diagrams showing the results of analyzing the expression of OCT4, SOX2, and NANOG in ferret iNSL cells and ferret iPS cells by RT-PCR.

As a result, it became clear that the ferret iPS cells express OCT4, SOX2, and NANOG. Furthermore, it also became clear that the ferret iNSL cells express SOX2.

INDUSTRIAL APPLICABILITY

According to the present invention, it is possible to provide a new technique for establishing iPS cells from mammalian somatic cells.

The invention claimed is:

1. A method of producing induced pluripotent stem cells, the method comprising:

a step (a) of introducing reprogramming factors into adult mammalian somatic cells isolated from an adult pluripotency induction-resistant non-human mammal and culturing the adult mammalian somatic cells in a neural stem cell culture medium to obtain induced neural stem cell-like cells; and a step (b) of culturing the induced neural stem cell-like cells obtained in step (a) in an ES cell culture medium to obtain induced pluripotent stem cells, wherein the induced neural stem cell-like cells endogenously express SOX2 and TERT, and do not endogenously express OCT4 and NANOG, wherein the reprogramming factors include at least one selected from Octamer-binding transcription factor family, at least one selected from SRY-related high motility group-box family, at least one selected from Krüppel-like factors family, at least one selected from MYC proto-oncogene family, at least one selected from RNA-binding protein LIN28 family, and at least one selected from Tumor protein P53 function-inhibiting substance, the reprogramming factors are introduced into the adult mammalian somatic cells in a form of a protein or a nucleic acid encoding the protein, wherein the adult pluripotency induction-resistant non-human mammal is a mammal that cannot establish iPS cells even when the reprogramming factors of at least one selected from Octamer-binding transcription factor family, at least one selected from SRY-related high motility group-box family, at least one selected from Krüppel-like factors family, and at least one selected from MYC proto-oncogene family are expressed in combination in somatic cells of the pluripotency induction-resistant animal, and wherein the neural stem cell culture medium contains a MAP kinase inhibitor, a Glycogen synthase kinase 3β inhibitor, and a Transforming growth factor β inhibitor, and the ES cell culture medium contains basic fibroblast growth factor.

2. The method of claim 1, wherein the reprogramming factors further includes one or more selected from the group consisting of each of the following groups: at least one of a Lysine demethylase family, at least one of a Gli-similar family, and a homeobox transcription factor NANOG.

3. A method of producing somatic cells, the method comprising: obtaining induced pluripotent stem cells by the method of claim 1, and differentiating the induced pluripotent stem cells into a somatic cell type selected from the group consisting of glandular epithelia cells, vascular cells, cartilage cells, fat cells, and nerve cells.

4. The method of claim 1, wherein the pluripotency induction-resistant animal is selected from the group consisting of canine, porcine, bovine, ovine, caprine, and marmoset.

5. The method of claim 1, wherein the pluripotency induction-resistant animal is canine.

6. The method of claim 3, wherein the pluripotency induction-resistant animal is marmoset.

7. The method of claim 3, wherein the pluripotency induction-resistant animal is porcine.

8. The method of claim 1, wherein the ES cell culture medium contains the basic fibroblast growth factor at a concentration of 4 to 10 ng/mL.

9. The method of claim 8, wherein the ES cell culture medium contains no MAP kinase inhibitor, no glycogen synthase kinase 3β inhibitor, and no transforming growth factor β inhibitor.

10. The method of claim 8, wherein the ES cell culture medium essentially consists of Dulbecco's modified Eagle's medium, a serum replacement, and the basic fibroblast growth factor.

11. The method of claim 8, wherein the ES cell culture medium consists of Dulbecco's modified Eagle's medium, a serum replacement, the basic fibroblast growth factor, non-essential amino acid, L-glutamine and 2-mercaptoethanol.

12. The method of claim 1, wherein the induced neural stem cell-like cells further endogenously express one or more neuronal stem cell markers selected from the group consisting of PAX6, SOX1, and ZFP521.

13. The method of claim 1, wherein the neural stem cell culture medium comprises DMEM/F12 medium and Neurobasal medium in a ratio of 1:1, an N2 supplement, and a B27 supplement.

14. The method of claim 1, wherein the reprogramming factors are expression constructs in which DNA encoding the reprogramming factor and a promoter are linked, and the expression constructs are incorporated into episomal plasmid vectors.

* * * * *